(12) United States Patent
Duffield et al.

(10) Patent No.: US 9,751,923 B2
(45) Date of Patent: Sep. 5, 2017

(54) ADMINISTRATION OF DKK1 MUTEINS TO TREAT FIBROSIS

(71) Applicants: University of Washington through its Center for Commercialization, Seattle, WA (US); Children's Hospital Medical Center, Cincinnati, OH (US)

(72) Inventors: Jeremy Duffield, Seattle, WA (US); Shuyu Ren, Shoreline, WA (US); Rashmi Hedge, Cincinnati, OH (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 0 days.

(21) Appl. No.: 14/438,860

(22) PCT Filed: Nov. 1, 2013

(86) PCT No.: PCT/US2013/068107
§ 371 (c)(1),
(2) Date: Apr. 27, 2015

(87) PCT Pub. No.: WO2014/071211
PCT Pub. Date: May 8, 2014

(65) Prior Publication Data
US 2015/0337021 A1 Nov. 26, 2015

Related U.S. Application Data

(60) Provisional application No. 61/721,447, filed on Nov. 1, 2012.

(51) Int. Cl.
| | | |
|---|---|---|
| *A61K 8/64* | (2006.01) | |
| *A61K 38/17* | (2006.01) | |
| *C07K 14/435* | (2006.01) | |
| *C07K 14/47* | (2006.01) | |

(52) U.S. Cl.
CPC ...... *C07K 14/4703* (2013.01); *A61K 38/1709* (2013.01)

(58) Field of Classification Search
None
See application file for complete search history.

(56) References Cited

FOREIGN PATENT DOCUMENTS

DE       EP 2098244 A1 * 9/2009 ......... A61K 38/1709

OTHER PUBLICATIONS

He, et al. (hereinafter 'He') 'Wnt/B-Catenin Signaling Promotes Renal Interstitial Fibrosis(Published online before print Aug. 27, 2009, doi:10.1681/ASN.2009070762JASN Sep. 1, 2009 vol. 20 No. 9 1864-1866'.*
Satoh et al., "Klotho protects against mouse renal fibrosis by inhibiting Wnt signaling", Am J Physiol Renal Physiol 303: F1641-F1651, 2012, First published Oct. 3, 2012; doi:10.1152/ajprenal.00460.2012.*
Ahn et al., "Structural Basis of Wnt Signaling Inhibition by Dickkopf Binding to LRP5/6" Developmental cell, 2011, DOI 10.1016/j.devcel.2011.09.003.*
Goritz, et al. A pericyte origin of spinal cord scar tissue.Science 2011 333:238.
Acharya, et al. The bHLH transcription factor Tcf21 is required for lineage-specific EMT of cardiac fibroblast progenitors. Development 2012 139:2139.
Kisseleva, et al. Myofibroblasts revert to an inactive phenotype during regression of liver fibrosis. PNAS 2012 109:9448.
Cheng, et al. Crystal structures of the extracellular domain of LRP6 and its complex with DKK1. Nature Structural & Molecular Biology, vol. 18, No. 1204-10. 2011.
Ren, et al. LRP-6 is a coreceptor for multiple fibrogenic signaling pathways in pericytes and myofibroblasts that are inhibited by DKK-1. PNAS 110: 1440-1445, 2013.
Higgins and Sharp (1989) CABIOS. 5:151-153.
Gao et al., (2004) J. Virology 78:6381-6388.
Srivastava et al., (1983) J. Virology 45:555.
Chiorini et al., (1998) J. Virology 71:6823.
Chiorini et al., (1999) J. Virology 73:1309.
Bantel-Schaal et al., (1999) J. Virology 73:939.
Xiao et al., (1999) J. Virology 73:3994.
Shade et al., (1986) J. Virol. 58:921.
Gao et al., (2002) Proc. Nat. Acad. Sci. USA 99:11854.
Ahn et al Dev. Cell 21:862-73, 2011.
Mercurio, S. et al., Connective-Tissue Growth Factor Modulates WNT Signaling and Interacts with the WNT Receptor Complex, Development, May 1, 2004, Vo. 31, No. 9, pp. 2137-2147.
Friedman, et al. Therapy for fibrotic diseases: nearing the starting line. Sci Trans Med 2013 5:167sr1.
Luper, M.L., et al., (2006) Regulation of fibrosis by the immune system Adv Immunol 89:245-288.

* cited by examiner

*Primary Examiner* — Michael Pak
(74) *Attorney, Agent, or Firm* — K&L Gates LLP; Louis C. Cullman; Michelle Glasky Bergman

(57) ABSTRACT

The present disclosure provides molecules, compositions and methods for treating scarring in organs. The molecules, compositions and methods treat scarring by modulating the WNT, platelet-derived growth factor receptor (PDGFR), transforming growth factor-beta (TGF3) and/or connective-tissue growth factor (CTGF) signaling pathways.

9 Claims, 34 Drawing Sheets

Fig. 3.
A
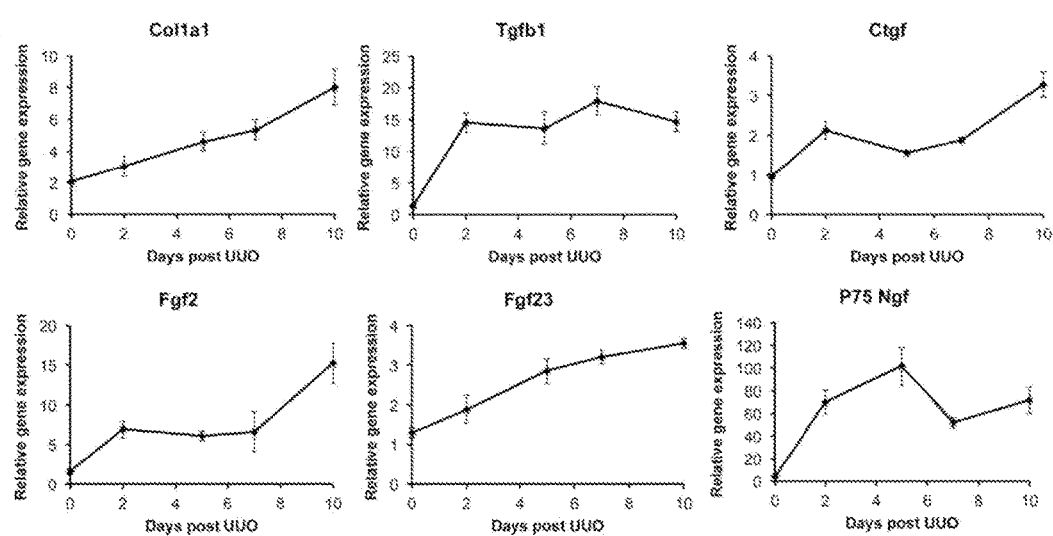
B
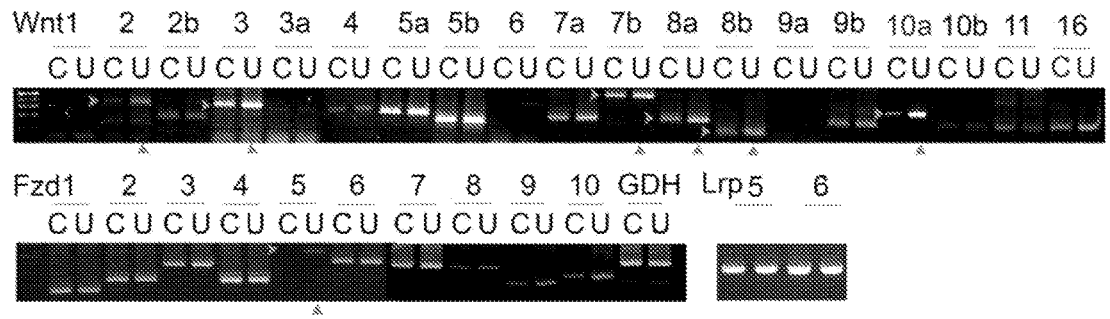

Fig. 4.
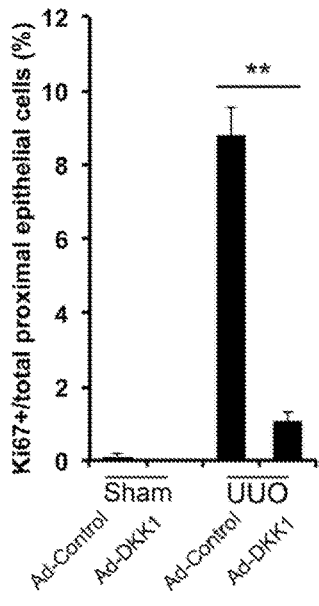
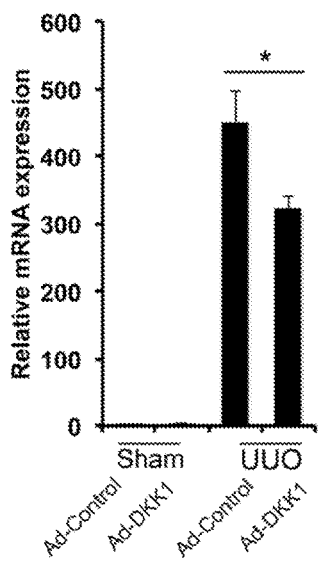
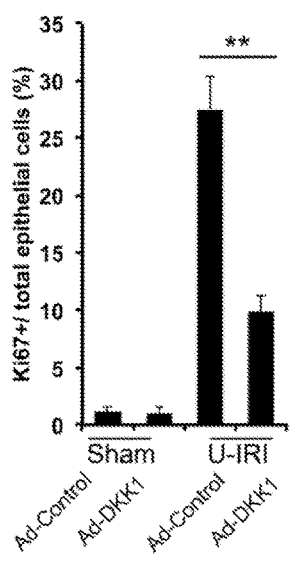
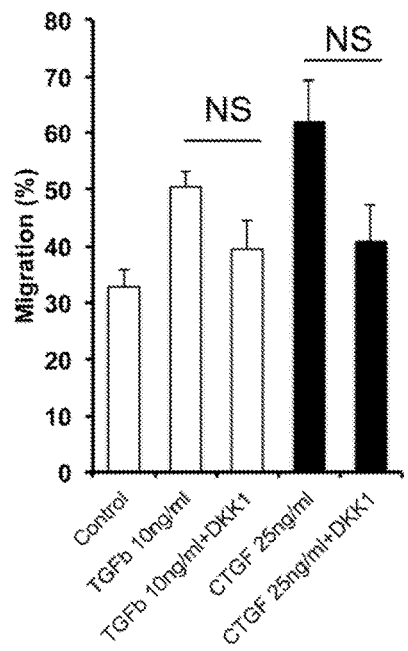

Fig. 6.
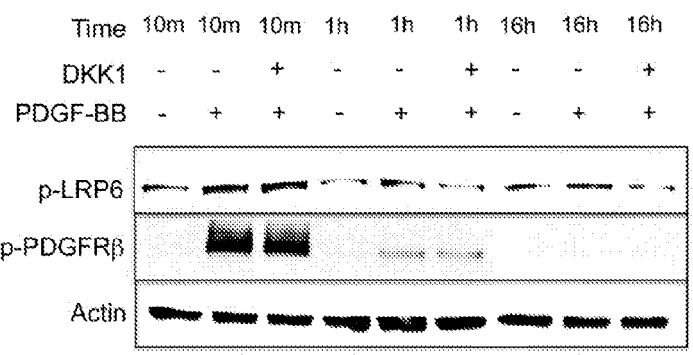
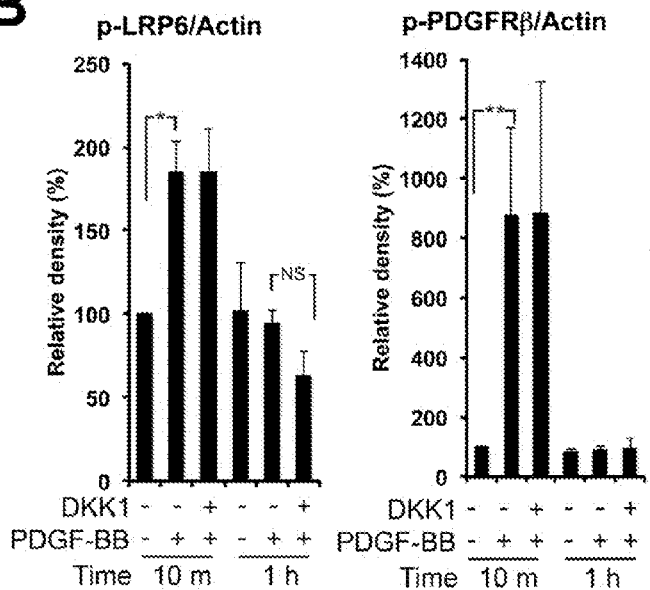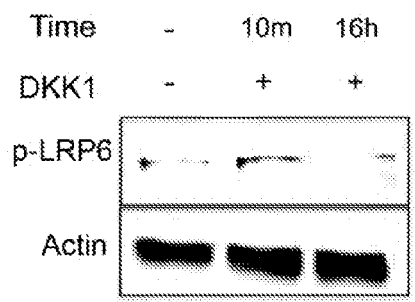

Fig. 6 Continued.
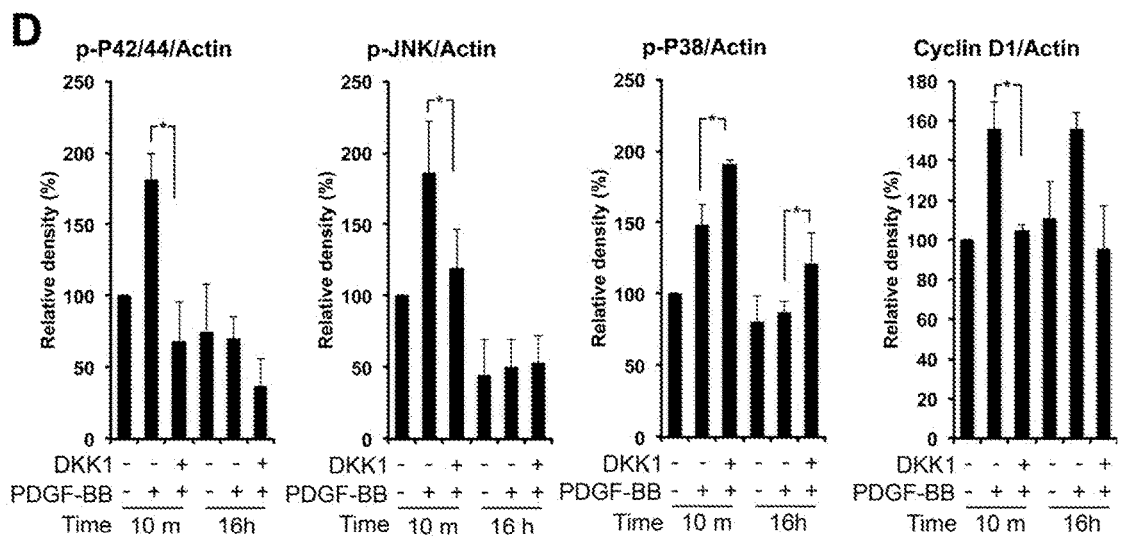
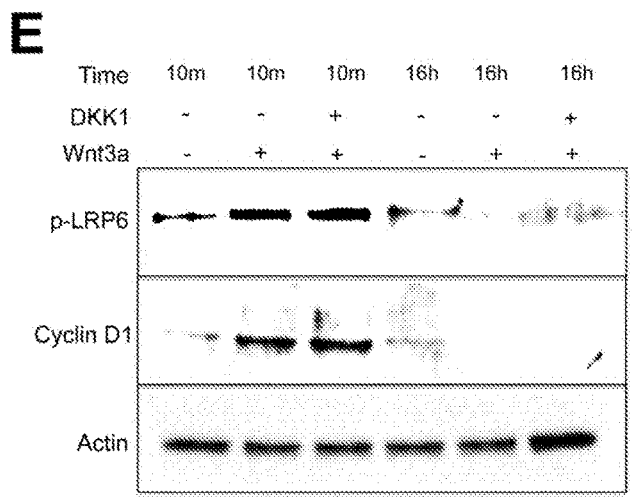

Fig. 9.
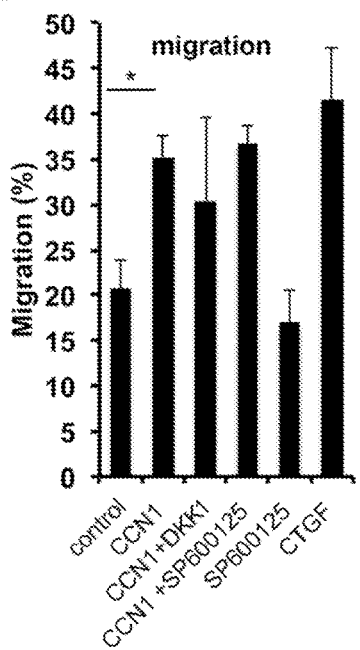
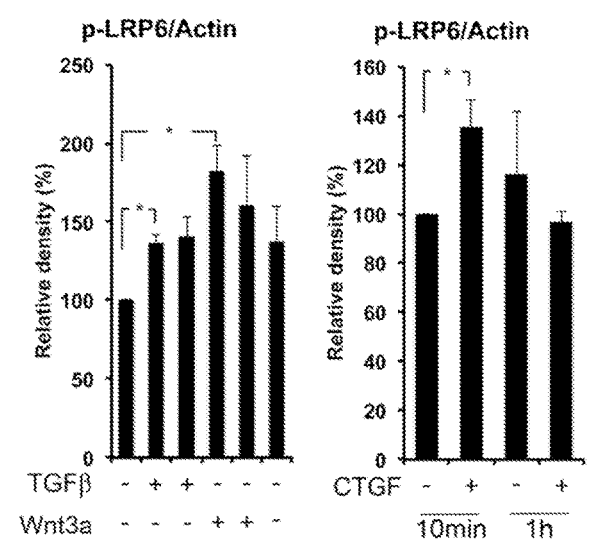
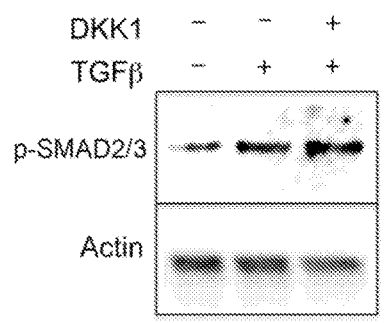

Fig. 10 Continued.
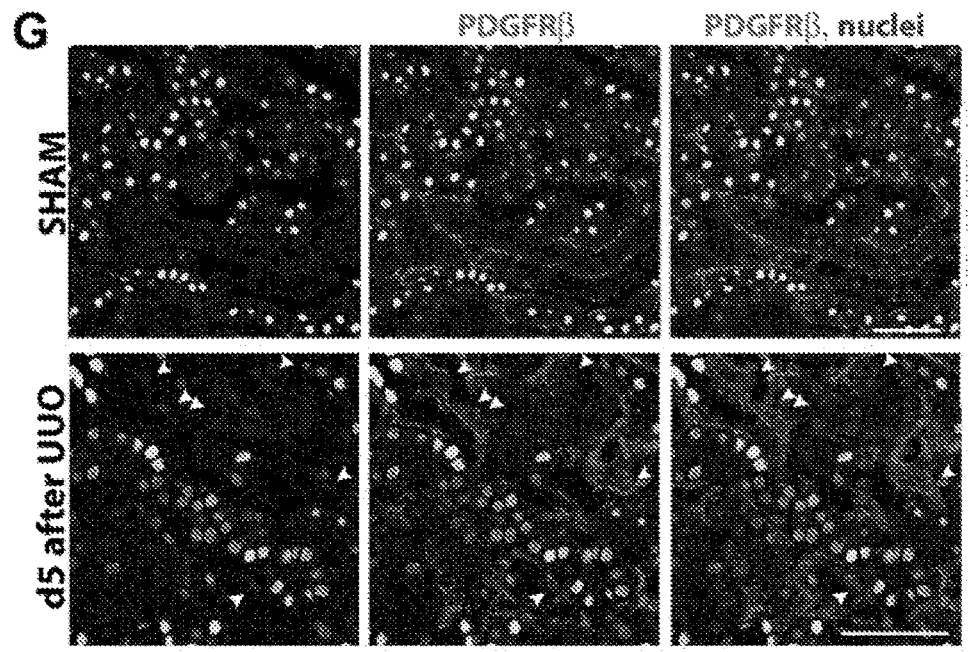
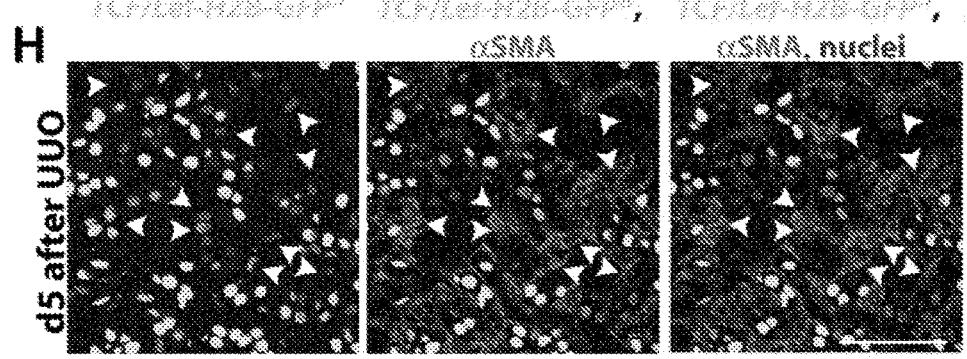
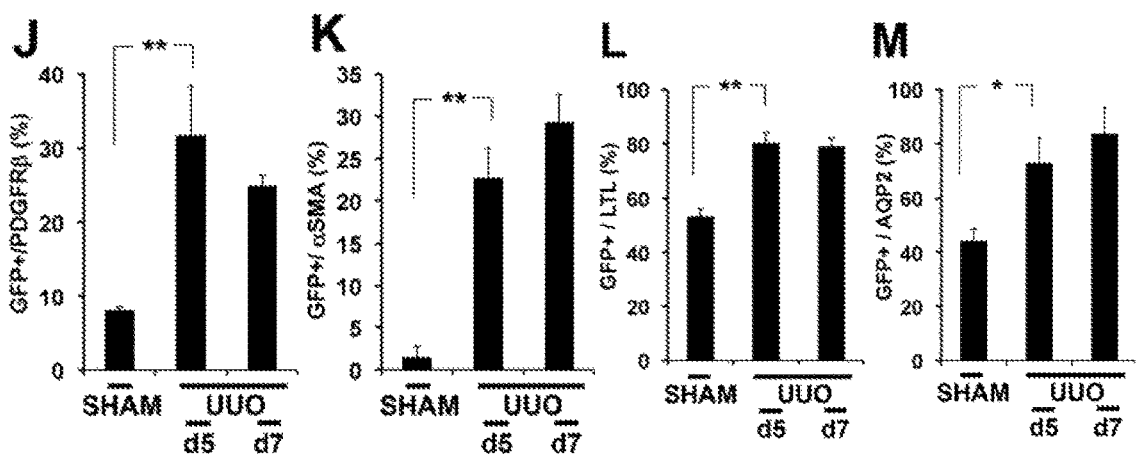

Fig. 16.

Human LRP5 LOCUS with binding domains underlined.

MEAAPPGPPW<u>PLLLLLLLLLALCGCPAPAAASPLLLFANRRDVRLVDA</u>
<u>GGVKLESTIVVSGLEDAAAVDFQFSKGAVYWTDVSEEAIKQTYLNQT</u>
<u>GAAVQNVVISGLVSPDGLACDWVGKKLYWTDSETNRIEVANLNGTSR</u>
<u>KVLFWQDLDQPRAIALDPAHGYMYWTDWGETPRIERAGMDGSTRKI</u>
<u>IVDSDIYWPNGLTIDLEEQKLYWADAKLSFIHRANLDGSFRQKVVEGS</u>
<u>LTHPFALTLSGDTLYWTDWQTRSIHACNKRTGGKRKEILSALYSPMDI</u>
<u>QVLSQERQPFFHTRCEEDNGGCSHLCLLSPSEPFYTCACPTGVQLQ</u>
<u>DNGRTCKAGAE</u>EVLLLARRTDLRRISLDTPDFTDIVLQVDDIRHAIAID
YDPLEGYVYWTDDEVRAIRRAYLDGSGAQTLVNTEINDPDGIAVDWV
ARNLYWTDTGTDRIEVTRLNGTSRKILVSEDLDEPRAIALHPVMGLMY
WTDWGENPKIECANLDGQERRVLVNASLGWPNGLALDLQEGKLYW
GDAKTDKIEVINVDGTKRRTLLEDKLPHIFGFTLLGDFIYWTDWQRRSI
ERVHKVKASRDVIIDQLPDLMGLKAVNVAKVVGTNPCADRNGGCSHL
CFFTPHATRCGCPIGLELLSDMKTCIV<u>PEAFLVFTSRAAIHRISLETNN</u>
<u>NDVAIPLTGVKEASALDFDVSNNHIYWTDVSLKTISRAFMNGSSVEHV</u>
<u>VEFGLDYPEGMAVDWMGKNLYWADTGTNRIEVARLDGQFRQVLVW</u>
<u>RDLDNPRSLALDPTKGYIYWTEWGGKPRIVRAFMDGTNCMTLVDKV</u>
<u>GRANDLTIDYADQRLYWTDLDTNMIESSNMLGQERVVIADDLPHPFG</u>
<u>LTQYSDYIYWTDWNLHSIERADKTSGRNRTLIQGHLDFVMDILVFHSS</u>
<u>RQDGLNDCMHNNGQCGQLCLAIPGGHRCGCASHYTLDPSSRNCSP</u>
<u>P</u>TTFLLFSQKSAISRMIPDDQHSPDLILPLHGLRNVKAIDYDPLDKFIY
WVDGRQNIKRAKDDGTQPFVLTSLSQGQNPDRQPHDLSIDIYSRTLF
WTCEATNTINVHRLSGEAMGVVLRGDRDKPRAIVVNAERGYLYFTN
MQDRAAKIERAALDGTEREVLFTTGLIRPVALVVDNTLGKLFWVDADL
KRIESCDLSGANRLTLEDANIVQPLGLTILGKHLYWIDRQQQMIERVEK
TTGDKRTRIQGRVAHLTGIHAVEEVSLEEFSAHPCARDNGGCSHICIA
KGDGTPRCSCPVHLVLLQNLLTCGEPPTCSPDQFACATGEIDCIPGA
WRCDGFPECDDQSDEEGCPVCSAAQFPCARGQCVDLRLRCDGEA
DCQDRSDEADCDAICLPNQFRCASGQCVLIKQQCDSFPDCIDGSDE
LMCEITKPPSDDSPAHSSAIGPVIGIILSLFVMGGVYFVCQRVVCQRYA
GANGPFPHEYVSGTPHVPLNFIAPGGSQHGPFTGIACGKSMMSSVS
LMGGRGGVPLYDRNHVTGASSSSSSSTKATLYPPILNPPPSPATDPS
LYNMDMFYSSNIPATARPYRPYIIRGMAPPTTPCSTDVCDSDYSASR
WKASKYYLDLNSDSDPYPPPPTPHSQYLSAEDSCPPSPATERSYFH
LFPPPPSPCTDSS

Fig. 17.

Human LRP6 LOCUS (Accession No. AAI43726) with binding domains underlined.

MGAVLRSLLACSFCVLLRAA<u>PLLLYANRRDLRLVDATNGKENATIVVGGLE
DAAAVDFVFSHGLIYWSDVSEEAIKRTEFNKTESVQNVVSGLLSPDGLA
CDWLGEKLYWTDSETNRIEVSNLDGSLRKVLFWQELDQPRAIALDPSSG
FMYWTDWGEVPKIERAGMDGSSRFIIINSEIYWPNGLTLDYEEQKLYWAD
AKLNFIHKSNLDGTNRQAVVKGSLPHPFALTLFEDILYWTDWSTHSILACN
KYTGEGLREIHSDIFSPMDIHAFSQQRQPNATNPCGIDNGGCSHLCLMSP
VKPFYQCACPTGVKLLENGKTCKDGATE</u>LLLLARRTDLRRISLDTPDFTDI
VLQLEDIRHAIAIDYDPVEGYIYWTDDEVRAIRRSFIDGSGSQFVVTAQIAH
PDGIAVDWVARNLYWTDTGTDRIEVTRLNGTMRKILISEDLEEPRAIVLDP
MVGYMYWTDWGEIPKIERAALDGSDRVVLVNTSLGWPNGLALDYDEGKI
YWGDAKTDKIEVMNTDGTGRRVLVEDKIPHIFGFTLLGDYVYWTDWQRR
SIERVHKRSAEREVIIDQLPDLMGLKATNVHRVIGSNPCAEENGGCSHLC
LYRPQGLRCACPIGFELISDMKTCIV<u>PEAFLLFSRRADIRRISLETNNNNVA
IPLTGVKEASALDFDVTDNRIYWTDISLKTISRAFMNGSALEHVVEFGLDY
PEGMAVDWLGKNLYWADTGTNRIEVSKLDGQHRQVLVWKDLDSPRALA
LDPAEGFMYWTEWGGKPKIDRAAMDGSERTTLVPNVGRANGLTIDYAKR
RLYWTDLDTNLIESSNMLGLNREVIADDLPHPFGLTQYQDYIYWTDWSRR
SIERANKTSGQNRTIIQGHLDYVMDILVFHSSRQSGWNECASSNGHCSH
LCLAVPVGGFVCGCPAHYSLNADNRTCSAP</u>TTFLLFSQKSAINRMVIDEQ
QSPDIILPIHSLRNVRAIDYDPLDKQLYWIDSRQNMIRKAQEDGSQGFTVV
VSSVPSQNLEIQPYDLSIDIYSRYIYWTCEATNVINVTRLDGRSVGVVLKG
EQDRPRAIVVNPEKGYMYFTNLQERSPKIERAALDGTEREVLFFSGLSKP
IALALDSRLGKLFWADSDLRRIESSDLSGANRIVLEDSNILQPVGLTVFEN
WLYWIDKQQQMIEKIDMTGREGRTKVQARIAQLSDIHAVKELNLQEYRQH
PCAQDNGGCSHICLVKGDGTTRCSCPMHLVLLQDELSCGESQFQCASG
QCIDGALRCNGDANCQDKSDEKNCEVLCLIDQFRCANGQCIGKHKKCD
HNVDCSDKSDELDCYPTEEPAPQATNTVGSVIGVIVTIFVSGTVYFICQRM
LCPRMKGDGETMTNDYVVHGPASVPLGYVPHPSSLSGSLPGMSRGKS
MISSLSIMGGSSGPPYDRAHVTGASSSSSSTKGTYFPAILNPPPSPATE
RSHYTMEFGYSSNSPSTHRSYSYRPYSYRHFAPPTTPCSTDVCDSDYAP
SRMTSVATAKGYTSDLNYDSEPVPPPPTPRSQYLSAEENYESCPPSPYT
ERSYSHHLYPPPPSPCTDSS

Fig. 18.

Human LRP5 open reading frame with regions coding the binding domains underlined.

atggaggcagcgccgcccgggccgccgtgg<u>ccgctgctgctgctgctgctgctgctggcgctgtgcggctgcccggccccgccgcggcct</u>
<u>cgccgctcctgctatttgccaaccgccgggacgtacggctggtggacgccggcggagtcaagctggagtccaccatcgtggtcagcggcctgga</u>
<u>ggatgcggccgcagtggacttccagttttccaaggggagccgtgtactggacagacgtgagcgaggaggccatcaagcagacctacctgaacca</u>
<u>gacgggggccgccgtgcagaacgtggtcatctccggcctggtctctcccgacggcctcgcctgcgactggatgggcaagaagctgtactggacg</u>
<u>gactcagagaccaaccgcatcgaggtggccaacctcaatggcacatccggaaggtgctcttctggcaggaccttgaccagccgagggccatc</u>
<u>gccttggaccccgctcacgggtacatgtactggacagactggggtgagacgccccggattgagcgggcagggatggatggcagcaccccggaa</u>
<u>gatcattgtggactcggacatttactggcccaatggactgaccatcgacctggaggagcagaagctctactgggctgacgccaagctcagcttcat</u>
<u>ccaccgtgccaacctggacggctcgttccggcagaaggtggtggagggcagcctgacgcacccccttcgccctgacgctctccggggacactctg</u>
<u>tactggacagactggcagaccccgctccatccatgcctgcaacaagcgcactgggggggaagaggaaggagatcctgagtgccctctactcaccc</u>
<u>atggacatccaggtgctgagccaggagcggcagcctttcttccacactcgctgtgaggaggacaatggcggctgctccacctgtgcctgctgtcc</u>
<u>ccaagcgagcctttctacacatgcgcctgccccacgggtgtgcagctgcaggacaacggcaggacgtgtaaggcaggagccgaggaggtgct</u>
gctgctggcccggcggacggacctacggaggatctcgctggacacgccggacttcaccgacatcgtgctgcaggtggacgacatccggcacgc
cattgccatcgactacgacccgctagagggctatgtctactggacagatgacgaggtgcgggccatccgcagggcgtacctggacgggtctggg
gcgcagacgctggtcaacaccgagatcaacgaccccgatggcatcgcggtcgactgggtggcccgaaacctctactggaccgacacgggcac
ggaccgcatcgaggtgacgcgcctcaacggcacctcccgcaagatcctggtgtcggaggacctggacgagccccgagccatcgcactgcacc
ccgtgatgggcctcatgtactggacagactggggagagaaccctaaaatcgagtgtgccaacttggatgggcaggagcggcgtgtgctggtcaa
tgcctcctcgggtggcccaacggcctggccctggacctgcaggaggggaagctctactggggagacgccaagacagacaagatcgaggtg
atcaatgttgatgggacgaagaggcggaccctcctggaggacaagctcccgcacattttcgggttcacgctgctgggggacttcatctactggact
gactggcagcgccgcagcatcgagcgggtgcacaaggtcaaggccagccgggacgtcatcattgaccagctgcccgacctgatgggctcaa
agctgtgaatgtggccaaggtcgtcggaaccaacccgtgtgcggacaggaacggggggtgcagccacctgtgcttcttcacaccccacgcaac
ccggtgtggctgcccatcggcctggagctgctgagtgacatgaagacctgcatcgt<u>gcctgaggccttcttggtcttcaccagcagagccgccatc</u>
<u>cacaggatctccctcgagaccaataacaacgacgtggccatcccgctcacgggcgtcaaggaggcctcagccctggactttgatgtgtccaaca</u>
<u>accacatttactggacagacgtcagcctgaagaccatcagccgcgccttcatgaacgggagctcggtggagcacgtggtggaatttggccttgac</u>
<u>taccccgagggcatggccgttgactggatgggcaagaacctctactggccgacactggaccaatagaatcgaagtggcgcggctggacgg</u>
<u>gcagttccggcaagtcctcgtgtggagggacttggacaacccgaggtcgctggccctggatccaccaagggctacatctactggaccgagtgg</u>
<u>ggcggcaagccgaggatcatgcggccttcatggacgggaccaactgcatgacgctggtggacaaggtggccggccaacgacctcacca</u>
<u>ttgactacgctgaccagcgcctctactggaccgacctggacaccaacatgatcgagtcgtccaacatgctggtcaggagcgggtcgtgattgcc</u>
<u>gacgatctccgcacccgttcggtctgacgcagtacagcgattatatctactggacagactggaatctgcacagcattgagcgggccgacaagac</u>
<u>tagcggccggaaccgcaccctcatccagggccacctggacttcgtgatggacatcctggtgttccactcctcccgccaggatggcctcaatgactg</u>
<u>tatgcacaacaacgggcagtgtgggcagctgtgccttgccatcccggcggccaccgctgcggctgcgcctcacactacaccctggaccccagc</u>
<u>agcccgcaactgcagcccgccc</u>accaccttcttgctgttcagccagaaatctgccatcagtcggatgatcccggacgaccagcacagcccggatct
catcctgccctgcatggactgaggaacgtcaaagccatcgactatgacccactggacaagttcatctactgggtggatgggcgccagaacatca
agcgagccaaggacgacgggacccagcccctttgtttgacctctctgagccaaggccaaaacccagacaggcagccccacgacctcagcatc
gacatctacagccggacactgttctggacgtgcgaggccaccaataccatcaacgtccacaggctgagcggggaagccatgggggtggtgctg
cgtggggaccgcgacaagcccagggccatcgtcgtcaacgcggagcgagggtacctgtacttcaccaacatgcaggacccgggcagccaaga
tcgaacgcgcagccctggacggcaccgagcgcgaggtcctcttcaccaccggcctcatccgccctgtggccctggtggtggacaacacactgg
gcaagctgttctgggtggacgcggacctgaagcgcattgagagctgtgacctgtcaggggccaaccgcctgaccctggaggacgccaacatcg
tgcagcctctgggcctgaccatccttggcaagcatctctactggatcgaccgccagcagcagatgatcgagcgtgtggagaagaccaccgggga
caagcggactcgcatccagggccgtgtcgcccacctcactggcatccatgcagtggaggaagtcagcctggaggagttctcagcccacccatgt
gcccgtgacaatggtggctgctcccacatctgtattgccaagggtgatgggacaccacggtgctcatgccagtccacctcgtgctcctgcagaac
ctgctgacctgtgagagccgcccacctgctccccggaccagtttgcatgccacaggggagatcgactgtatcccggggcctggcgctgtga
cggctttcccgagtgcgatgaccagagcgacgaggagggctgccccgtgtgctccgccgcccagttccctgcgcgcggggtcagtgtggac
ctgcgcctgcgctgcgacggcgaggcagactgtcaggaccgctcagacgaggtggactgtgacgccatctgcctgcccaaccagttccggtgtg
cgagcggccagtgtgtcctcatcaaacagcagtgcgactcctccccgactgtatcgacggctccgacgagctcatgtgtgaaatcaccaagccg
ccctcagacgacagcccggcccacagcagtgccatcgggcccgtcattggcatcatcctctctctcttcgtcatgggtggtgtctattttgtgtgccag
cgcgtggtgtgccagcgctatgcgggggccaacgggcccttcccgcacgagtatgtcagcgggaccccgcacgtgccccctcaatttcatagccc
cgggcggttcccagcatggcccccttcacaggcatcgcatgcggaaagtccatgatgagctccgtgagcctgatggggggccggggcgggtgc
ccctctacgaccggaaccacgtcacaggggcctcgtccagcagctcgtcagcacgaaggccacgctgtacccgccgatcctgaacccgccgc
cctccccggccacggacccctccctgtacaacatggacatgttctactcttcaaacattccggccactgcgagaccgtacaggcctacatcattcg
aggaatggcgccccgacgacgccctgcagcaccgacgtgtgtgacagcgactacagcgccagccgctggaaggccagcaagtactacctg
gatttgaactcggactcagaccccctatccacccccacccacgccccacagccagtacctgtcggcggaggacagctgcccgccctcgcccgcc
accgagaggagctacttccatctcttcccgccccctccgtcccctgcacggactcatcctga

Fig. 19.

Human LRP6 open reading frame with regions coding the binding domains underlined.

atggggggccgtcctgaggagcctcctggcctgcagcttctgtgtgctcctgagagcggcc<u>cctttgttgctttatgcaaacagacgggacttgcgattggtt</u>
<u>gatgctacaaatggcaaagagaatgctacgattgtagttggaggcttggaggatgcagctgcggtggactttgtgtttagtcatggcttgatatactggag</u>
<u>tgatgtcagcgaagaagccattaaacgaacagaatttaacaaaactgagagtgtgcagaatgttgttgtttctggattattgtcccccgatgggctggca</u>
<u>tgtgattggcttggagaaaaattgtactggacagattctgaaactaatcggattgaagtttctaatttagatggatctttacgaaaagttttatttggcaaga</u>
<u>gttggatcaacccagagctattgccttagatccttcaagtggttcatgtactggacagactggggagaagtgccaaagatagaacgtgctggaatgg</u>
<u>atggttcaagtcgcttcattataataaacagtgaaatttactggccaaatggactgactttggattatgaagaacaaaagctttattgggcagatgcaaaa</u>
<u>cttaatttcatccacaaatcaaatctggatggaacaaatcggcaggcagtggttaaaggttcccttccacatccttttgccttgacgttatttgaggacatatt</u>
<u>gtactggactgactggagcacacactccattttggcttgcaacaagtatactggtgaggtctgcgtgaaatccattctgacatcttctctcccatggatat</u>
<u>acatgccttcagccaacagaggcagccaaatgccacaaatccatgtggaattgacaatgggggttgttcccatttgtgtttgatgtctccagtcaagcctt</u>
<u>tttatcagtgtgcttgccccactggggtcaaactcctggagaatggaaaaacctgcaaagatggtgccacag</u>aattattgcttttagctcgaaggacag
acttgagacgcatttctttggatacaccagattttacagacattgttctgcagttagaagacatccgtcatgccattgccatagattacgatcctgtggaagg
ctacatctactggactgatgatgaagtgagggccatacgccgttcatttatagatggatctggcagtcagtttgtggtcactgctcaaattgcccatcctgat
ggtattgctgtggactgggttgcacgaaatctttattggacagacactggcactgatcgaatagaagtgacaaggctcaatggaccatgaggaagat
cttgatttcagaggacttagaggaaccccgggctattgtgttagatccatggttgggtacatgtattggactgactggggagaaattccgaaaattgag
cgagcagctctggatggttctgaccgtgtagtattggttaacacttctcttggttggccaaatggtttagccttggattatgatgaaggcaaaatatactggg
gagatgccaaaacagacaagattgaggttatgaatactgatggcactgggagacgagtactagtggaagacaaaattcctcacatatttggatttactt
tgttgggtgactatgtttactggactgactggcagaggcgtagcattgaaagagttcataaacgaagtgcagagagggaagtgatcatagatcagctg
cctgacctcatgggcctaaaggctacaaatgttcatcgagtgattggttccaacccctgtgctgaggaaaacgggggatgtagccatctctgcctctata
gacctcagggccttcgctgtgcttgccctattggctttgaactcatcagtgacatgaagacctgcattgtc<u>ccagaggctttccttttgttttcacggagagca</u>
<u>gatatcagacgaatttctctggaaacaaacaataataatgtggctattccactcactggtgtcaaagaagcttctgctttggattttgatgtgacagacaac</u>
<u>cgaatttattggactgatatatcactcaagaccatcagcagagcctttatgaatggcagtgcactggaacatgtggtagaattcggcttagattatccaga</u>
<u>aggcatggcagtagactggcttgggaagaacttgtactgggcagacacaggaacgaatcgaattgaggtgtcaaagttggatgggcagccaccgac</u>
<u>aagttttggtgtggaaagacctagataagtcccagagctctcgcgttggaccctgccgaaggattatgtattggactgaatggggtggaaaacctaaga</u>
<u>tagacagagctgcaatggatggaagtgaacgtactaccttagttccaaatgtgggcgggcaaacggcctaactattgattatgctaaaaggagggctt</u>
<u>tattggacagaccctggacaccaacttaatagaatcttcaaatatgcttgggctcaaccgtgaagttatagcagatgacttgcctcatcctttggcttaactc</u>
<u>agtaccaagattatatctactggacggactggagccgacgcagcattgagcgtgccaacaaaaccagtggccaaaaccgcaccatcattcaggc</u>
<u>catttggattatgtgatggacatcctcgtctttcactcatctcgacagtcagggtggaatgaatgtgcttccagcaatgggcactgctcccacctctgcttgg</u>
<u>ctgtgccagttgggggttttgtttgtggatgccctgcccactactctcttaatgctgacaacaggacttgtagtgctcct</u>acgactttcctgctcttcagtcaaa
agagtgccatcaaccgcatggtgattgatgaacaacagagccccgacatcatccttccatccacagccttcggaatgtccgggccattgactatgac
ccactggacaagcaactctattggattgactcacgacaaaacatgatccgaaaggcacaagaagatggcagccagggctttactgtggttgtgagct
cagttccgagtcagaacctggaaatacaaccctatgacctcagcattgatatttacagccgctacatctactggacttgtgaggctaccaatgtcattaat
gtgacaagattagatgggagatcagttggagtggtgctgaaaggcgagcaggacagacctcgagccgttgtggtaaacccagagaaagggtatat
gtattttaccaatcttcaggaaaggtctcctaaaattgaacgggctgctttggatgggacagaacgggaggtcctcttttcagtggcttaagtaaaccaat
tgcttttagcccttgatagcaggctgggcaagctctttggggctgattcagatctccggcgaattgaaagcagtgatctctcaggtgctaaccggatagtatt
agaagactccaatatcttgcagcctgtgggacttactgtgtttgaaaactggctctattggattgataaacagcagcaaatgattgaaaaaattgacatg
acaggtcgagagggtagaaccaaagtccaagctcgaattgcccagcttagtgacattcatgcagtaaaggagctgaaccttcaagaatacagaca
gcaccctgtgctcaggataatggtggctgttcacatatttgtcttgtaaaggggggatggtactacaaggtgttcttgccccatgcacctggttcacttcaag
atgagctatcatgtggagaacctccaacatgttctcctcagcagtttacttgtttcacgggggaaattgactgtatccctgtggcttggcggtgcgatgggtt
actgaatgtgaagaccacagtgatgaactcaattgtcctgtatgctcagagtcccagttccagtgtgccagtgggcagtgtattgatggtgccctccgatg
caatggagatgcaaactgccaggacaaatcagatgagaagaactgtgaagtgctttgtttaattgatcagttccgctgtgccaatggtcagtgcattgg
aaagcacaagaagtgtgatcataatgtggattgcagtgacaagtcagatgaactggattgttatccgactgaagaaccagcaccacaggccaccaa
tacagttggttctgttattggcgtaattgtcaccattttgtgtctggaactgtataactttatctgccagaggatgttgtgtccacgtatgaagggagatgggga
aactatgactaatgactatgtagttcatggaccagcttctgtgcctcttggttatgtgccacacccaagttctttgtcaggatctcttccaggaatgtctcgag
gtaaatcaatgatcagctccctcagtatcatgggggggaagcagtggaccccctatgaccgagcccatgttacaggagcatcatcaagtagttcttca
agcaccaaaggcacttacttccctgcaattttgaaccctccaccatcccagccacagagcgatcacattacactatggaattttggatattcttcaaaca
gtccttccactcataggtcatacagctacaggccatatagctaccggcactttgcacccccccaccctgcagcacagatgtttgtgacagtgact
atgctcctagtcggagaatgacctcagtggcaacagccaagggctataccagtgacttgaactatgattcagaacctgtgcccccacctcccacaccc
cgaagccaatacttgtcagcagaggagaactatgaaagctgcccaccttctccatacacagagaggagctattctcatcacctctacccaccgccac
cctctccctgtacagactcctcctga

Fig. 20.

A. MGN1004: Human DKK1 with rat serum albumin secretion leader sequence (underlined), a HIS tag (bold and in italics), and a DAPzyme cleavage site (boxed).
<u>MKWVTFLLLLFISGSAFS</u>*HHHHHHHH* [Q] TLNSVLNSNAIKNLPPPLGGA
AGHPGSAVSAAPGILYPGGNKYQTIDNYQPYPCAEDEECGTDEYCASPT
RGGDAGVQICLACRKRRKRCMRHAMCCPGNYCKNGICVSSDQNHFRG
EIEETITESFGNDHSTLDGYSRRTTLSSKMYHTKGQEGSVCLRSSDCAS
GLCCARHFWSKICKPVLKEGQVCTKHRRKGSHGLEIFQRCYCGEGLSC
RIQKDHHQASNSSRLHTCQRH

B. MGN1005: Human DKK1C variant with rat serum albumin secretion leader sequence (underlined), a HIS tag (bold and in italics) and a DAPzyme cleavage site (boxed).
<u>MKWVTFLLLLFISGSAFS</u>*HHHHHHHH* [Q] MYHTKGQEGSVCLRSSDCAS
GLCCARHFWSKICKPVLKEGQVCTKHRRKGSHGLEIFQRCYCGEGLSC
RIQKDHHQASNSSRLHTCQRH

C. MGN1006: Mouse DKK1 with rat serum albumin secretion leader sequence (underlined), a HIS tag (bold and in italics), and a DAPzyme cleavage site (boxed).
<u>MKWVTFLLLLFISGSAFS</u>*HHHHHHHH* [Q] TLNSVLINSNAIKNLPPPLGGA
GGQPGSAVSVAPGVLYEGGNKYQTLDNYQPYPCAEDEECGSDEYCSSP
SRGAAGVGGVQICLACRKRRKRCMRHAMCCPGNYCKNGICMPSDHSH
FPRGEIEESIIENLGNDHNAAAGDGYPRRTTLTSKIYHTKGQEGSVCLRSS
DCAAGLCCARHFWSKICKPVLKEGQVCTKHKRKGSHGLEIFQRCYCGE
GLACRIQKDHHQASNSSRLHTCQRH

D. MGN1007: Mouse DKK1C variant with rat serum albumin secretion leader sequence (underlined), a HIS tag (bold and in italics) and a DAPzyme cleavage site (boxed).
<u>MKWVTFLLLLFISGSAFS</u>*HHHHHHHH* [Q] IYHTKGQEGSVCLRSSDCAAG
LCCARHFWSKICKPVLKEGQVCTKHKRKGSHGLEIFQRCYCGEGLACRI
QKDHHQASNSSRLHTCQRH

Fig. 21.

Native Human DKK1 with signal peptide for secretion boxed, binding domains underlined, and areas of particular relevance inside the binding domains bold and in italics.

`MMALGAAGATRVFVAMVAAALGGHPLLGVSA`TLNSVL*NSN AIKN*LPPPLGGAAGHPGSAVSAAPGILYPGGNKYQTIDNYQP YPCAEDEECGTDEYCASPTRGGDAGVQICLACRKRRKRCM RHAMCCPGNYCKNGICVSSDQNHFRGEIEETITESFGNDHS TLDGYSRRTTLSSK<u>MYHTKGQEGSVCLRSSDCASGLCCAR*H FWSKICK*PVLKEGQVC*TKHRRKGSHGLEIFQR*CYCGEGLSC RIQKDHHQASNSSRLHTCQRH</u>

Native Mouse DKK1 with signal peptide for secretion underlined.
<u>MMVVCAAAAVRFLAVFTMMALCSLPLLGASA</u>TLNSVLINSNAI KNLPPPLGGAGGQPGSAVSVAPGVLYEGGNKYQTLDNYQP YPCAEDEECGSDEYCSSPSRGAAGVGGVQICLACRKRRKR CMRHAMCCPGNYCKNGICMPSDHSHFPRGEIEESIIENLGN DHNAAAGDGYPRRTTLTSKIYHTKGQEGSVCLRSSDCAAGL CCARHFWSKICKPVLKEGQVCTKHKRKGSHGLEIFQRCYCG EGLACRIQKDHHQASNSSRLHTCQRH

Fig. 22.

A. MGN1004 Nucleotide Sequence:
ATGAAATGGGTGACCTTTCTCCTGCTGCTGTTCATCAGCGGCTCCG
CTTTTAGCCACCATCACCATCACCACCACCACCAGACCCTGAACTC
CGTCCTCAACAGCAACGCCATCAAGAATCTCCCTCCTCCTCTCGGA
GGCGCTGCTGGACATCCTGGATCCGCTGTGTCCGCCGCTCCTGGA
ATCCTGTACCCCGGCGGCAACAAGTACCAGACCATTGACAACTACC
AGCCCTACCCTTGCGCCGAGGACGAGGAATGCGGCACCGATGAGT
ACTGCGCCTCCCCTACAAGGGGAGGAGATGCCGGCGTGCAAATCT
GCCTGGCCTGCAGGAAGAGGAGGAAGAGGTGCATGAGGCACGCC
ATGTGCTGCCCCGGCAACTACTGCAAGAACGGCATCTGCGTCAGC
TCCGATCAGAACCATTTCAGGGGCGAGATCGAGGAGACCATCACC
GAGAGCTTCGGCAACGACCACAGCACCCTGGACGGCTACTCCAG
GAGGACCACCCTCAGCAGCAAGATGTACCACACAAAGGGCCAGGA
GGGCAGCGTGTGTCTGAGGAGCTCCGACTGTGCCAGCGGCCTCT
GTTGTGCCAGGCACTTTTGGAGCAAGATCTGCAAGCCCGTGCTCA
AGGAGGGCCAGGTGTGCACCAAGCACAGGAGGAAAGGCAGCCAC
GGCCTCGAGATCTTCCAGAGGTGCTACTGCGGAGAGGGCCTCTCC
TGCAGGATCCAGAAAGACCACCACCAGGCTAGCAACAGCAGCAGG
CTGCACCTGTCAGAGGCACTGA

B. MGN1005 Nucleotide Sequence:
ATGAAGTGGGTGACCTTCCTCCTGCTGCTCTTCATCTCCGGCAGCG
CTTTCTCCCACCACCACCATCACCACCACCACCAGATGTACCACAC
AAAGGGCCAGGAGGGCAGCGTGTGTCTGAGGAGCTCCGACTGTG
CCAGCGGCCTCTGTTGTGCCAGGCACTTTTGGAGCAAGATCTGCA
AGCCCGTGCTCAAGGAGGGCCAGGTGTGCACCAAGCACAGGAGG
AAAGGCAGCCACGGCCTCGAGATCTTCCAGAGGTGCTACTGCGGA
GAGGGCCTCTCCTGCAGGATCCAGAAAGACCACCACCAGGCTAGC
AACAGCAGCAGGCTGCACCTGTCAGAGGCACTGA

Fig. 22 Continued.

C. MGN1006 Nucleotide Sequence:
ATGAAATGGGTCACCTTCCTGCTGCTCCTCTTCATCTCCGGCTCCG
CTTTTAGCCACCATCACCATCACCACCACCACCAGACCCTGAACAG
CGTCCTCATCAACAGCAACGCTATCAAGAATCTCCCTCCTCCTCTG
GGAGGAGCTGGCGGACAACCTGGAAGCGCTGTGAGCGTGGCTCC
CGGAGTGCTCTACGAAGGCGGCAACAAGTACCAGACCCTGGACAA
CTACCAGCCCTACCCTTGTGCCGAGGACGAAGAGTGCGGCTCCGA
CGAGTATTGCAGCAGCCCTTCCAGAGGAGCTGCCGGAGTCGGAG
GAGTGCAGATCTGTCTCGCCTGCAGAAAGAGGAGGAAGAGGTGCA
TGAGGCACGCCATGTGTTGCCCCGGCAACTACTGCAAAAATGGCAT
CTGCATGCCCTCCGATCACAGCCATTTCCCCAGGGGCGAGATCGA
GGAGAGCATCATCGAGAACCTGGGCAACGACCATAATGCCGCCGC
TGGAGACGGATACCCTAGGAGGACCACCCTCACCAGCAAGATCTA
CCACACCAAGGGACAGGAGGGCAGCGTCTGCCTCAGGAGCAGCG
ATTGCGCTGCTGGCCTCTGCTGTGCCAGGCATTTCTGGAGCAAGAT
CTGCAAGCCCGTCCTGAAGGAGGGCCAGGTCTGCACCAAGCATAA
GAGGAAGGGCAGCCACGGCCTGGAGATCTTCCAGAGATGCTACTG
TGGCGAGGGCCTGGCCTGCAGGATCCAGAAAGACCACCACCAGG
CCAGCAACAGCAGCAGGCTGCACACCTGCCAGAGACACTGA

D. MGN1007 Nucleotide Sequence:
ATGAAGTGGGTGACCTTCCTCCTGCTGCTCTTCATCTCCGGCAGCG
CTTTCTCCCACCACCACCATCACCACCACCACCAGATCTACCACAC
CAAGGGCCAGGAGGGCAGCGTGTGCCTCAGGAGCAGCGATTGCG
CTGCTGGCCTCTGCTGTGCCAGGCATTTCTGGAGCAAGATCTGCA
AGCCCGTCCTGAAGGAGGGCCAGGTCTGCACCAAGCATAAGAGGA
AGGGCAGCCACGGCCTGGAGATCTTCCAGAGATGCTACTGTGGCG
AGGGCCTGGCCTGCAGGATCCAGAAAGACCACCACCAGGCCAGC
AACAGCAGCAGGCTGCACACCTGCCAGAGACACTGA

Fig. 22 Continued.

E. Human DKK1 Nucleotide Sequence:
ATGATGGCTCTGGGCGCAGCGGGAGCTACCCGGGTCTTTGTCGCG
ATGGTAGCGGCGGCTCTCGGCGGCCACCCTCTGCTGGGAGTGAGC
GCCACCTTGAACTCGGTTCTCAATTCCAACGCTATCAAGAACCTGCC
CCCACCGCTGGGCGGCGCTGCGGGGCACCCAGGCTCTGCAGTCA
GCGCCGCCGGGAATCCTGTACCCGGGCGGGAATAAGTACCAGA
CCATTGACAACTACCAGCCGTACCGTGCGCAGAGGACGAGGAGT
GCGGCACTGATGAGTACTGCGCTAGTCCCACCCGCGGAGGGGACG
CAGGCGTGCAAATCTGTCTCGCCTGCAGGAAGCGCCGAAAACGCT
GCATGCGTCACGCTATGTGCTGCCCCGGGAATTACTGCAAAAATGG
AATATGTGTGTCTTCTGATCAAAATCATTTCCGAGGAGAAATTGAGGA
AACCATCACTGAAAGCTTTGGTAATGATCATAGCACCTTGGATGGGTA
TTCCAGAAGAACCACCTTGTCTTCAAAAATGTATCACACCAAAGGAC
AAGAAGGTTCTGTTTGTCTCCGGTCATCAGACTGTGCCTCAGGATTG
TGTTGTGCTAGACACTTCTGGTCCAAGATCTGTAAACCTGTCCTGAA
AGAAGGTCAAGTGTGTACCAAGCATAGGAGAAAAGGCTCTCATGGA
CTAGAAATATTCCAGCGTTGTTACTGTGGAGAAGGTCTGTCTTGCCG
GATACAGAAAGATCACCATCAAGCCAGTAATTCTTCTAGGCTTCACAC
TTGTCAGAGACACTAA

Fig. 23.
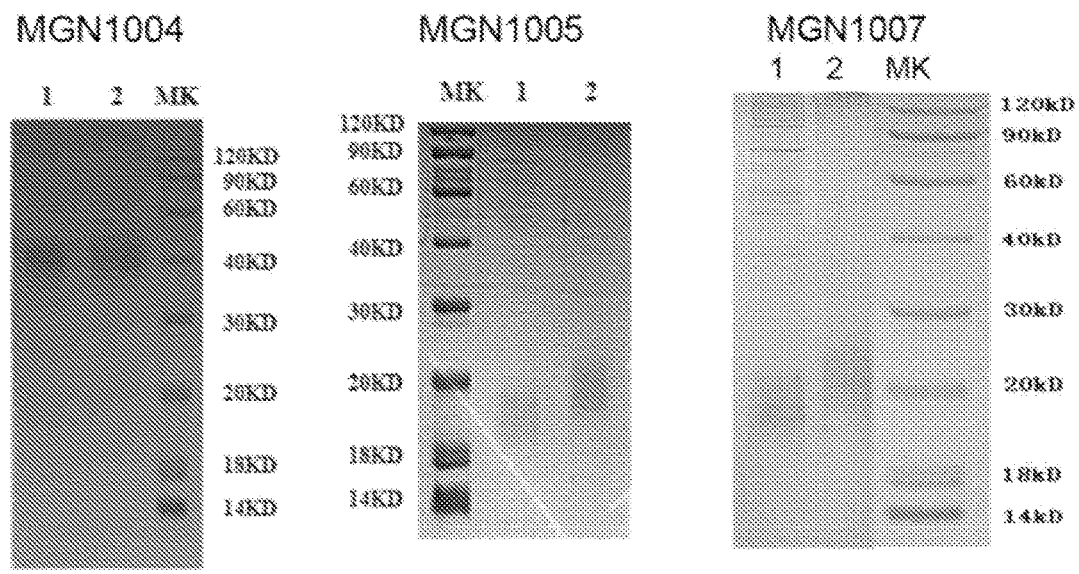
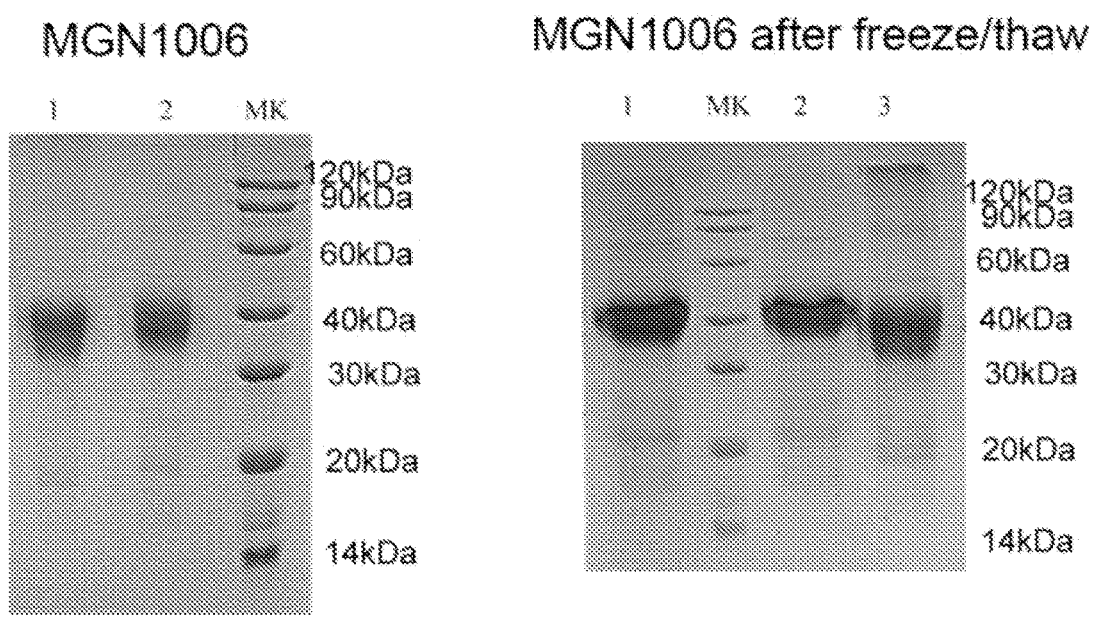

Fig. 25 Continued.
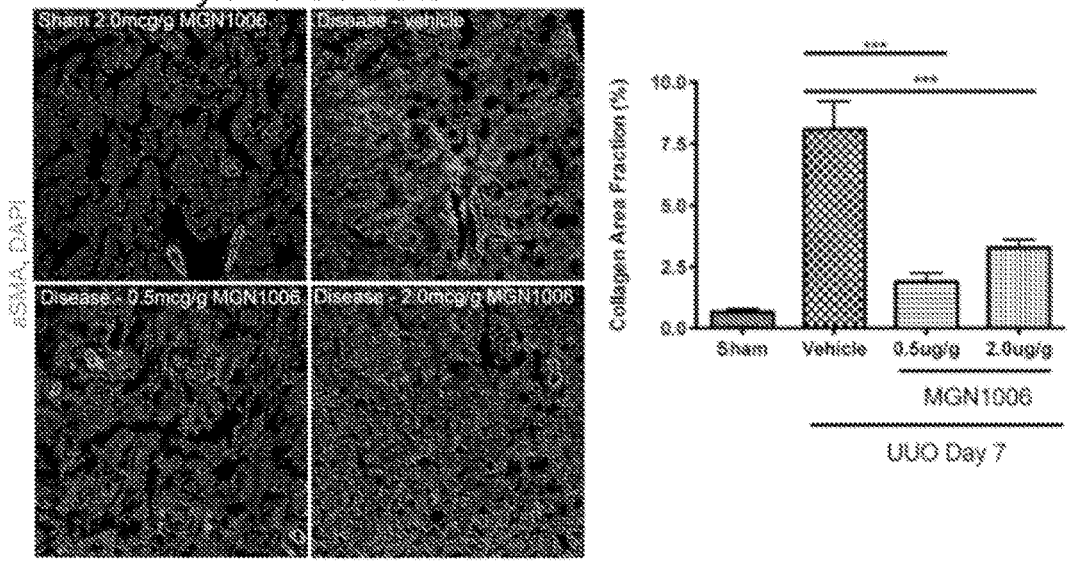
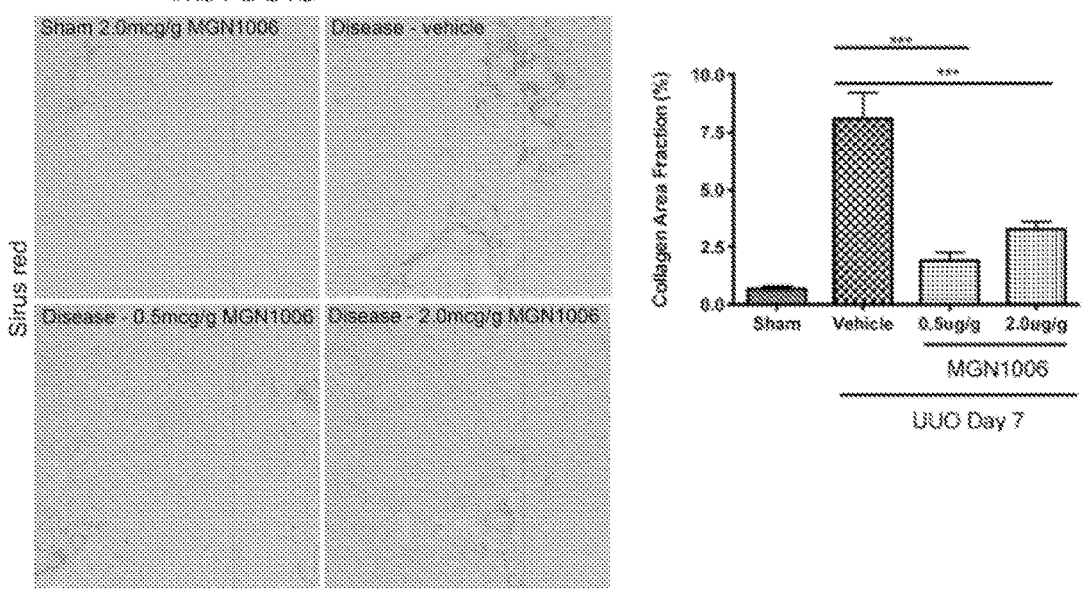

SEQUENCE LISTING

```
<160> NUMBER OF SEQ ID NOS: 56

<210> SEQ ID NO 1
<211> LENGTH: 1615
<212> TYPE: PRT
<213> ORGANISM: Homo sapiens

<400> SEQUENCE: 1

Met Glu Ala Ala Pro Gly Pro Pro Trp Pro Leu Leu Leu Leu
1               5                   10                  15

Leu Leu Leu Leu Ala Leu Cys Gly Cys Pro Ala Pro Ala Ala Ala Ser
                20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Ser Gly Leu Glu Asp
        50                  55                  60

Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
                100                 105                 110

Leu Ala Cys Asp Trp Val Gly Lys Lys Leu Tyr Trp Thr Asp Ser Glu
            115                 120                 125

Thr Asn Arg Ile Glu Val Ala Asn Leu Asn Gly Thr Ser Arg Lys Val
        130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
                180                 185                 190

Asp Ile Tyr Trp Pro Asn Gly Leu Thr Ile Asp Leu Glu Glu Gln Lys
            195                 200                 205

Leu Tyr Trp Ala Asp Ala Lys Leu Ser Phe Ile His Arg Ala Asn Leu
        210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
                260                 265                 270

Glu Ile Leu Ser Ala Leu Tyr Ser Pro Met Asp Ile Gln Val Leu Ser
            275                 280                 285

Gln Glu Arg Gln Pro Phe Phe His Thr Arg Cys Glu Glu Asp Asn Gly
        290                 295                 300
```

-continued

```
Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
                420                 425                 430

Thr Asp Thr Gly Thr Asp Arg Ile Glu Val Thr Arg Leu Asn Gly Thr
            435                 440                 445

Ser Arg Lys Ile Leu Val Ser Glu Asp Leu Asp Glu Pro Arg Ala Ile
        450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
        595                 600                 605

Asn Gly Gly Cys Ser His Leu Cys Phe Phe Thr Pro His Ala Thr Arg
    610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
        675                 680                 685

Ile Tyr Trp Thr Asp Val Ser Leu Lys Thr Ile Ser Arg Ala Phe Met
    690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
```

-continued

```
            725                 730                 735
Thr Gly Thr Asn Arg Ile Glu Val Ala Arg Leu Asp Gly Gln Phe Arg
                740                 745                 750
Gln Val Leu Val Trp Arg Asp Leu Asp Asn Pro Arg Ser Leu Ala Leu
                755                 760                 765
Asp Pro Thr Lys Gly Tyr Ile Tyr Trp Thr Glu Trp Gly Gly Lys Pro
        770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
                805                 810                 815
Arg Leu Tyr Trp Thr Asp Leu Asp Thr Asn Met Ile Glu Ser Ser Asn
                820                 825                 830
Met Leu Gly Gln Glu Arg Val Val Ile Ala Asp Asp Leu Pro His Pro
                835                 840                 845
Phe Gly Leu Thr Gln Tyr Ser Asp Tyr Ile Tyr Trp Thr Asp Trp Asn
        850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
                885                 890                 895
Ser Ser Arg Gln Asp Gly Leu Asn Asp Cys Met His Asn Asn Gly Gln
                900                 905                 910
Cys Gly Gln Leu Cys Leu Ala Ile Pro Gly Gly His Arg Cys Gly Cys
            915                 920                 925
Ala Ser His Tyr Thr Leu Asp Pro Ser Ser Arg Asn Cys Ser Pro Pro
930                 935                 940
Thr Thr Phe Leu Leu Phe Ser Gln Lys Ser Ala Ile Ser Arg Met Ile
945                 950                 955                 960
Pro Asp Asp Gln His Ser Pro Asp Leu Ile Leu Pro Leu His Gly Leu
                965                 970                 975
Arg Asn Val Lys Ala Ile Asp Tyr Asp Pro Leu Asp Lys Phe Ile Tyr
            980                 985                 990
Trp Val Asp Gly Arg Gln Asn Ile Lys Arg Ala Lys Asp Asp Gly Thr
        995                 1000                1005
Gln Pro Phe Val Leu Thr Ser Leu Ser Gln Gly Gln Asn Pro Asp
        1010                1015                1020
Arg Gln Pro His Asp Leu Ser Ile Asp Ile Tyr Ser Arg Thr Leu
        1025                1030                1035
Phe Trp Thr Cys Glu Ala Thr Asn Thr Ile Asn Val His Arg Leu
        1040                1045                1050
Ser Gly Glu Ala Met Gly Val Val Leu Arg Gly Asp Arg Asp Lys
        1055                1060                1065
Pro Arg Ala Ile Val Val Asn Ala Glu Arg Gly Tyr Leu Tyr Phe
        1070                1075                1080
Thr Asn Met Gln Asp Arg Ala Ala Lys Ile Glu Arg Ala Ala Leu
        1085                1090                1095
Asp Gly Thr Glu Arg Glu Val Leu Phe Thr Thr Gly Leu Ile Arg
        1100                1105                1110
Pro Val Ala Leu Val Val Asp Asn Thr Leu Gly Lys Leu Phe Trp
        1115                1120                1125
Val Asp Ala Asp Leu Lys Arg Ile Glu Ser Cys Asp Leu Ser Gly
        1130                1135                1140
```

-continued

```
Ala Asn Arg Leu Thr Leu Glu Asp Ala Asn Ile Val Gln Pro Leu
1145                1150                1155

Gly Leu Thr Ile Leu Gly Lys His Leu Tyr Trp Ile Asp Arg Gln
1160                1165                1170

Gln Gln Met Ile Glu Arg Val Glu Lys Thr Thr Gly Asp Lys Arg
1175                1180                1185

Thr Arg Ile Gln Gly Arg Val Ala His Leu Thr Gly Ile His Ala
1190                1195                1200

Val Glu Glu Val Ser Leu Glu Glu Phe Ser Ala His Pro Cys Ala
1205                1210                1215

Arg Asp Asn Gly Gly Cys Ser His Ile Cys Ile Ala Lys Gly Asp
1220                1225                1230

Gly Thr Pro Arg Cys Ser Cys Pro Val His Leu Val Leu Leu Gln
1235                1240                1245

Asn Leu Leu Thr Cys Gly Glu Pro Pro Thr Cys Ser Pro Asp Gln
1250                1255                1260

Phe Ala Cys Ala Thr Gly Glu Ile Asp Cys Ile Pro Gly Ala Trp
1265                1270                1275

Arg Cys Asp Gly Phe Pro Glu Cys Asp Asp Gln Ser Asp Glu Glu
1280                1285                1290

Gly Cys Pro Val Cys Ser Ala Ala Gln Phe Pro Cys Ala Arg Gly
1295                1300                1305

Gln Cys Val Asp Leu Arg Leu Arg Cys Asp Gly Glu Ala Asp Cys
1310                1315                1320

Gln Asp Arg Ser Asp Glu Ala Asp Cys Asp Ala Ile Cys Leu Pro
1325                1330                1335

Asn Gln Phe Arg Cys Ala Ser Gly Gln Cys Val Leu Ile Lys Gln
1340                1345                1350

Gln Cys Asp Ser Phe Pro Asp Cys Ile Asp Gly Ser Asp Glu Leu
1355                1360                1365

Met Cys Glu Ile Thr Lys Pro Pro Ser Asp Ser Pro Ala His
1370                1375                1380

Ser Ser Ala Ile Gly Pro Val Ile Gly Ile Ile Leu Ser Leu Phe
1385                1390                1395

Val Met Gly Gly Val Tyr Phe Val Cys Gln Arg Val Val Cys Gln
1400                1405                1410

Arg Tyr Ala Gly Ala Asn Gly Pro Phe Pro His Glu Tyr Val Ser
1415                1420                1425

Gly Thr Pro His Val Pro Leu Asn Phe Ile Ala Pro Gly Gly Ser
1430                1435                1440

Gln His Gly Pro Phe Thr Gly Ile Ala Cys Gly Lys Ser Met Met
1445                1450                1455

Ser Ser Val Ser Leu Met Gly Gly Arg Gly Gly Val Pro Leu Tyr
1460                1465                1470

Asp Arg Asn His Val Thr Gly Ala Ser Ser Ser Ser Ser Ser Ser
1475                1480                1485

Thr Lys Ala Thr Leu Tyr Pro Pro Ile Leu Asn Pro Pro Pro Ser
1490                1495                1500

Pro Ala Thr Asp Pro Ser Leu Tyr Asn Met Asp Met Phe Tyr Ser
1505                1510                1515

Ser Asn Ile Pro Ala Thr Ala Arg Pro Tyr Arg Pro Tyr Ile Ile
1520                1525                1530
```

```
Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 2
<211> LENGTH: 1567
<212> TYPE: PRT
<213> ORGANISM: Homo sapiens

<400> SEQUENCE: 2

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285
```

-continued

```
Asp Asn Gly Gly Cys Ser His Leu Cys Leu Met Ser Pro Val Lys Pro
        290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
                340                 345                 350

Val Leu Gln Leu Glu Asp Ile Arg His Ala Ile Ala Ile Asp Tyr Asp
                355                 360                 365

Pro Val Glu Gly Tyr Ile Tyr Trp Thr Asp Glu Val Arg Ala Ile
        370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
        420                 425                 430

Asn Gly Thr Met Arg Lys Ile Leu Ile Ser Glu Asp Leu Glu Glu Pro
                435                 440                 445

Arg Ala Ile Val Leu Asp Pro Met Val Gly Tyr Met Tyr Trp Thr Asp
        450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
                500                 505                 510

Lys Ile Glu Val Met Asn Thr Asp Gly Thr Gly Arg Arg Val Leu Val
                515                 520                 525

Glu Asp Lys Ile Pro His Ile Phe Gly Phe Thr Leu Leu Gly Asp Tyr
        530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
                580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
        610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
        690                 695                 700
```

```
Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
    770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
```

```
            1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Ser Gln Phe
    1235                1240                1245

Gln Cys Ala Ser Gly Gln Cys Ile Asp Gly Ala Leu Arg Cys Asn
    1250                1255                1260

Gly Asp Ala Asn Cys Gln Asp Lys Ser Asp Glu Lys Asn Cys Glu
    1265                1270                1275

Val Leu Cys Leu Ile Asp Gln Phe Arg Cys Ala Asn Gly Gln Cys
    1280                1285                1290

Ile Gly Lys His Lys Lys Cys Asp His Asn Val Asp Cys Ser Asp
    1295                1300                1305

Lys Ser Asp Glu Leu Asp Cys Tyr Pro Thr Glu Glu Pro Ala Pro
    1310                1315                1320

Gln Ala Thr Asn Thr Val Gly Ser Val Ile Gly Val Ile Val Thr
    1325                1330                1335

Ile Phe Val Ser Gly Thr Val Tyr Phe Ile Cys Gln Arg Met Leu
    1340                1345                1350

Cys Pro Arg Met Lys Gly Asp Gly Glu Thr Met Thr Asn Asp Tyr
    1355                1360                1365

Val Val His Gly Pro Ala Ser Val Pro Leu Gly Tyr Val Pro His
    1370                1375                1380

Pro Ser Ser Leu Ser Gly Ser Leu Pro Gly Met Ser Arg Gly Lys
    1385                1390                1395

Ser Met Ile Ser Ser Leu Ser Ile Met Gly Gly Ser Ser Gly Pro
    1400                1405                1410

Pro Tyr Asp Arg Ala His Val Thr Gly Ala Ser Ser Ser Ser Ser
    1415                1420                1425

Ser Ser Thr Lys Gly Thr Tyr Phe Pro Ala Ile Leu Asn Pro Pro
    1430                1435                1440

Pro Ser Pro Ala Thr Glu Arg Ser His Tyr Thr Met Glu Phe Gly
    1445                1450                1455

Tyr Ser Ser Asn Ser Pro Ser Thr His Arg Ser Tyr Ser Tyr Arg
    1460                1465                1470

Pro Tyr Ser Tyr Arg His Phe Ala Pro Pro Thr Thr Pro Cys Ser
    1475                1480                1485

Thr Asp Val Cys Asp Ser Asp Tyr Ala Pro Ser Arg Met Thr Ser
    1490                1495                1500

Val Ala Thr Ala Lys Gly Tyr Thr Ser Asp Leu Asn Tyr Asp Ser
    1505                1510                1515
```

```
Glu Pro Val Pro Pro Pro Thr Pro Arg Ser Gln Tyr Leu Ser
    1520            1525                1530

Ala Glu Glu Asn Tyr Glu Ser Cys Pro Pro Ser Pro Tyr Thr Glu
    1535                1540                1545

Arg Ser Tyr Ser His His Leu Tyr Pro Pro Pro Ser Pro Cys
    1550                1555                1560

Thr Asp Ser Ser
    1565

<210> SEQ ID NO 3
<211> LENGTH: 4848
<212> TYPE: DNA
<213> ORGANISM: Homo sapiens

<400> SEQUENCE: 3
```

| | |
|---|---|
| atggaggcag cgccgcccgg gccgccgtgg ccgctgctgc tgctgctgct gctgctgctg | 60 |
| gcgctgtgcg gctgcccggc ccccgccgcg gcctcgccgc tcctgctatt tgccaaccgc | 120 |
| cgggacgtac ggctggtgga cgccggcgga gtcaagctgg agtccaccat cgtggtcagc | 180 |
| ggcctggagg atgcggccgc agtggacttc cagttttcca agggagccgt gtactggaca | 240 |
| gacgtgagcg aggaggccat caagcagacc tacctgaacc agacggggc cgccgtgcag | 300 |
| aacgtggtca tctccggcct ggtctctccc gacggcctcg cctgcgactg ggtgggcaag | 360 |
| aagctgtact ggacggactc agagaccaac cgcatcgagg tggccaacct caatggcaca | 420 |
| tcccggaagg tgctcttctg gcaggacctt gaccagccga ggccatcgc cttggacccc | 480 |
| gctcacgggt acatgtactg gacagactgg ggtgagacgc ccggattga gcgggcaggg | 540 |
| atggatggca gcacccggaa gatcattgtg gactcggaca tttactggcc aatggactg | 600 |
| accatcgacc tggaggagca gaagctctac tgggctgacg ccaagctcag cttcatccac | 660 |
| cgtgccaacc tggacggctc gttccggcag aaggtggtgg agggcagcct gacgcacccc | 720 |
| ttcgccctga cgctctccgg ggacactctg tactggacag actggcagac ccgctccatc | 780 |
| catgcctgca caagcgcac tgggggaag aggaaggaga tcctgagtgc cctctactca | 840 |
| cccatggaca tccaggtgct gagccaggag cggcagcctt tcttccacac tcgctgtgag | 900 |
| gaggacaatg gcggctgctc ccacctgtgc ctgctgtccc aagcgagcc tttctacaca | 960 |
| tgcgcctgcc ccacgggtgt gcagctgcag gacaacggca ggacgtgtaa ggcaggagcc | 1020 |
| gaggaggtgc tgctgctggc ccggcggacg gacctacgga ggatctcgct ggacacgccg | 1080 |
| gacttcaccg acatcgtgct gcaggtggac gacatccggc acgccattgc catcgactac | 1140 |
| gacccgctag agggctatgt ctactggaca gatgacgagg tgcgggccat ccgcagggcg | 1200 |
| tacctggacg ggtctgggc gcagacgctg gtcaacaccg agatcaacga ccccgatggc | 1260 |
| atcgcggtcg actgggtggc ccgaaacctc tactggaccg acacgggcac ggaccgcatc | 1320 |
| gaggtgacgc gcctcaacgg cacctcccgc aagatcctgg tgtcggagga cctgacgag | 1380 |
| ccccgagcca tcgcactgca ccccgtgatg ggcctcatgt actggacaga ctggggagag | 1440 |
| aaccctaaaa tcgagtgtgc caacttggat gggcaggagc ggcgtgtgct ggtcaatgcc | 1500 |
| tccctcgggt ggcccaacgg cctggccctg acctgcagg aggggaagct ctactgggga | 1560 |
| gacgccaaga cagacaagat cgaggtgatc aatgttgatg ggacgaagag gcggaccctc | 1620 |
| ctggaggaca agtcccgca catttcggg ttcacgctgc tggggactt catctactgg | 1680 |
| actgactggc agcgccgcag catcgagcgg gtgcacaagg tcaaggccag ccgggacgtc | 1740 |

```
atcattgacc agctgcccga cctgatgggg ctcaaagctg tgaatgtggc caaggtcgtc    1800
ggaaccaacc cgtgtgcgga caggaacggg gggtgcagcc acctgtgctt cttcacaccc    1860
cacgcaaccc ggtgtggctg ccccatcggc ctggagctgc tgagtgacat gaagacctgc    1920
atcgtgcctg aggccttctt ggtcttcacc agcagagccg ccatccacag gatctccctc    1980
gagaccaata caacgacgt ggccatcccg ctcacgggcg tcaaggaggc ctcagccctg     2040
gactttgatg tgtccaacaa ccacatttac tggacagacg tcagcctgaa gaccatcagc    2100
cgcgccttca tgaacgggag ctcggtggag cacgtggtgg agtttggcct tgactacccc    2160
gagggcatgg ccgttgactg gatgggcaag aacctctact gggccgacac tgggaccaat    2220
agaatcgaag tggcgcggct ggacgggcag ttccggcaag tcctcgtgtg gagggacttg    2280
gacaacccga ggtcgctggc cctggatccc accaagggct acatctactg gaccgagtgg    2340
ggcggcaagc cgaggatcgt gcgggccttc atggacggga ccaactgcat gacgctggtg    2400
gacaaggtgg gccgggccaa cgacctcacc attgactacg ctgaccagcg cctctactgg    2460
accgacctgg acaccaacat gatcgagtcg tccaacatgc tgggtcagga gcgggtcgtg    2520
attgccgacg atctcccgca cccgttcggt ctgacgcagt acagcgatta tatctactgg    2580
acagactgga atctgcacag cattgagcgg ccgacaagaa ctagcggccg gaaccgcacc    2640
ctcatccagg gccacctgga cttcgtgatg acatcctgg tgttccactc ctcccgccag     2700
gatggcctca atgactgtat gcacaacaac gggcagtgtg ggcagctgtg ccttgccatc    2760
cccggcggcc accgctgcgg ctgcgcctca cactacaccc tggacccag cagccgcaac    2820 tgcagcccgc ccaccacctt cttgctgttc agccagaaat ctgccatcag tcggatgatc   2880
ccggacgacc agcacagccc ggatctcatc ctgcccctgc atggactgag gaacgtcaaa   2940
gccatcgact atgaccccact ggacaagttc atctactggg tggatgggcg ccagaacatc   3000
aagcgagcca aggacgacgg gacccagccc tttgttttga cctctctgag ccaaggccaa   3060
aacccagaca ggcagcccca cgacctcagc atcgacatct acagccggac actgttctgg   3120
acgtgcgagg ccaccaatac catcaacgtc acaggctga gcggggaagc catggggtg    3180 gtgctgcgtg gggaccgcga caagcccagg gccatcgtcg tcaacgcgga gcagggtac   3240 ctgtacttca ccaacatgca ggaccgggca gccaagatcg aacgcgcagc cctggacggc   3300
accgagcgcg aggtcctctt caccaccggc ctcatccgcc ctgtggccct ggtggtggac   3360
aacacactgg gcaagctgtt ctgggtggac gcggacctga gcgcattga gagctgtgac    3420 ctgtcagggg ccaaccgcct gaccctggag gacgccaaca tcgtgcagcc tctgggcctg   3480
accatccttg gcaagcatct ctactggatc gaccgccagc agcagatgat cgagcgtgtg   3540
gagaagacca ccggggacaa gcggactcgc atccagggcc gtgtcgccca cctcactggc   3600
atccatgcag tggaggaagt cagcctggag gagttctcag cccacccatg tgcccgtgac   3660
aatggtggct gctcccacat ctgtattgcc aagggtgatg ggacaccacg gtgctcatgc   3720
ccagtccacc tcgtgctcct gcagaacctg ctgacctgtg agagccgcc cacctgctcc    3780 ccggaccagt ttgcatgtgc cacaggggag atcgactgta tcccccgggc ctggcgctgt   3840
gacggctttc ccgagtgcga tgaccagagc gacgaggagg gctgccccgt gtgctccgcc   3900
gcccagttcc cctgcgcgcg gggtcagtgt gtggacctgc gcctgcgctg cgacggcgag   3960
gcagactgtc aggaccgctc agacgaggtg gactgtgacg ccatctgcct gcccaaccag   4020
ttccggtgtg cgagcggcca gtgtgtcctc atcaaacagc agtgcgactc cttccccgac   4080
tgtatcgacg gctccgacga gctcatgtgt gaaatcacca agccgccctc agacgacagc   4140
```

-continued

| | |
|---|---|
| ccggcccaca gcagtgccat cgggcccgtc attggcatca tcctctctct cttcgtcatg | 4200 |
| ggtggtgtct attttgtgtg ccagcgcgtg gtgtgccagc gctatgcggg ggccaacggg | 4260 |
| cccttcccgc acgagtatgt cagcgggacc ccgcacgtgc ccctcaattt catagccccg | 4320 |
| ggcggttccc agcatggccc cttcacaggc atcgcatgcg gaaagtccat gatgagctcc | 4380 |
| gtgagcctga tgggggccg gggcggggtg cccctctacg accggaacca cgtcacaggg | 4440 |
| gcctcgtcca gcagctcgtc cagcacgaag gccacgctgt acccgccgat cctgaacccg | 4500 |
| ccgccctccc cggccacgga cccctccctg tacaacatgg acatgttcta ctcttcaaac | 4560 |
| attccggcca ctgcgagacc gtacaggccc tacatcattc gaggaatggc gcccccgacg | 4620 |
| acgccctgca gcaccgacgt gtgtgacagc gactacagcg ccagccgctg gaaggccagc | 4680 |
| aagtactacc tggatttgaa ctcggactca gaccccatc caccccacc cacgcccac | 4740 |
| agccagtacc tgtcggcgga ggacagctgc ccgcctcgc ccgccaccga gaggagctac | 4800 |
| ttccatctct cccgccccc tccgtccccc tgcacggact catcctga | 4848 |

<210> SEQ ID NO 4
<211> LENGTH: 4842
<212> TYPE: DNA
<213> ORGANISM: Homo sapiens

<400> SEQUENCE: 4

| | |
|---|---|
| atgggggccg tcctgaggag cctcctggcc tgcagcttct gtgtgctcct gagagcggcc | 60 |
| cctttgttgc tttatgcaaa cagacgggac ttgcgattgg ttgatgctac aaatggcaaa | 120 |
| gagaatgcta cgattgtagt tggaggcttg gaggatgcag ctgcggtgga ctttgtgttt | 180 |
| agtcatggct tgatatactg gagtgatgtc agcgaagaag ccattaaacg aacagaattt | 240 |
| aacaaaactg agagtgtgca gaatgttgtt gtttctggat tattgtcccc cgatgggctg | 300 |
| gcatgtgatt ggcttggaga aaaattgtac tggacagatt ctgaaactaa tcggattgaa | 360 |
| gtttctaatt tagatggatc tttacgaaaa gtttttatttt ggcaagagtt ggatcaaccc | 420 |
| agagctattg ccttagatcc ttcaagtggg ttcatgtact ggacagactg gggagaagtg | 480 |
| ccaaagatag aacgtgctgg aatggatggt tcaagtcgct tcattataat aaacagtgaa | 540 |
| atttactggc caaatggact gactttggat tatgaagaac aaaagcttta ttgggcagat | 600 |
| gcaaaactta atttcatcca caatcaaat ctggatggaa caaatcggca ggcagtggtt | 660 |
| aaaggttccc ttccacatcc ttttgccttg acgttatttg aggacatatt gtactggact | 720 |
| gactggagca cacactccat tttggcttgc aacaagtata ctggtgaggg tctgcgtgaa | 780 |
| atccattctg acatcttctc tcccatggat atacatgcct tcagccaaca gaggcagcca | 840 |
| aatgccacaa atccatgtgg aattgacaat ggggttgtt cccatttgtg tttgatgtct | 900 |
| ccagtcaagc ttttttatca gtgtgcttgc cccactgggg tcaaactcct ggagaatgga | 960 |
| aaacctgca agatggtgc cacagaatta ttgcttttag ctcgaaggac agacttgaga | 1020 |
| cgcatttctt tggatacacc agattttaca gacattgttc tgcagttaga agacatccgt | 1080 |
| catgccattg ccatagatta cgatcctgtg aaggctaca tctactggac tgatgatgaa | 1140 |
| gtgagggcca tacgccgttc atttatagat ggatctggca gtcagtttgt ggtcactgct | 1200 |
| caaattgccc atcctgatgg tattgctgtg gactgggttg cacgaaatct ttattggaca | 1260 |
| gacactggca ctgatcgaat agaagtgaca aggctcaatg ggaccatgag gaagatcttg | 1320 |
| atttcagagg acttagagga accccgggct attgtgttag atcccatggt tgggtacatg | 1380 |

```
tattggactg actggggaga aattccgaaa attgagcgag cagctctgga tggttctgac   1440
cgtgtagtat tggttaacac ttctcttggt tggccaaatg gtttagcctt ggattatgat   1500
gaaggcaaaa tatactgggg agatgccaaa acagacaaga ttgaggttat gaatactgat   1560
ggcactggga gacagagtact agtggaagac aaaattcctc acatatttgg atttactttg   1620
ttgggtgact atgtttactg gactgactgg cagaggcgta gcattgaaag agttcataaa   1680
cgaagtgcag agagggaagt gatcatagat cagctgcctg acctcatggg cctaaaggct   1740
acaaatgttc atcgagtgat tggttccaac ccctgtgctg aggaaaacgg gggatgtagc   1800
catctctgcc tctatagacc tcagggcctt cgctgtgctt gccctattgg ctttgaactc   1860
atcagtgaca tgaagacctg cattgtccca gaggctttcc ttttgttttc acggagagca   1920
gatatcagac gaatttctct ggaaacaaac aataataatg tggctattcc actcactggt   1980
gtcaaagaag cttctgcttt ggattttgat gtgacagaca accgaattta ttggactgat   2040
atatcactca agaccatcag cagagccttt atgaatggca gtgcactgga acatgtggta   2100
gaattcggct tagattatcc agaaggcatg gcagtagact ggcttgggaa gaacttgtac   2160
tgggcagaca caggaacgaa tcgaattgag gtgtcaaagt tggatgggca gcaccgacaa   2220
gttttggtgt ggaaagacct agatagtccc agagctctcg cgttggaccc tgccgaagga   2280
tttatgtatt ggactgaatg gggtggaaaa cctaagatag acagagctgc aatggatgga   2340
agtgaacgta ctaccttagt tccaaatgtg gggcgggcaa acggcctaac tattgattat   2400
gctaaaagga ggctttattg gacagacctg gacaccaact taatagaatc ttcaaatatg   2460
cttgggctca accgtgaagt tatagcagat gacttgcctc atccttttgg cttaactcag   2520
taccaagatt atatctactg gacggactgg agccgacgca gcattgagcg tgccaacaaa   2580
accagtggcc aaaaccgcac catcattcag ggccatttgg attatgtgat ggacatcctc   2640
gtctttcact catctcgaca gtcagggtgg aatgaatgtg cttccagcaa tgggcactgc   2700
tcccacctct gcttggctgt gccagttggg ggttttgttt gtggatgccc tgcccactac   2760
tctcttaatg ctgacaacag gacttgtagt gctcctacga cttttcctgct cttcagtcaa   2820
aagagtgcca tcaaccgcat ggtgattgat gaacaacaga gccccgacat catccttccc   2880
atccacagcc ttcggaatgt ccgggccatt gactatgacc cactggacaa gcaactctat   2940
tggattgact cacgacaaaa catgatccga aaggcacaag aagatggcag ccagggcttt   3000
actgtggttg tgagctcagt tccgagtcag aacctggaaa tacaacccta tgacctcagc   3060
attgatattt acagccgcta catctactgg acttgtgagg ctaccaatgt cattaatgtg   3120
acaagattag atgggagatc agttggagtg gtgctgaaag gcgagcagga cagacctcga   3180
gccgttgtgg taaacccaga gaagggtat atgtatttta ccaatcttca ggaaaggtct   3240
cctaaaattg aacgggctgc tttggatggg acagaacggg aggtcctctt tttcagtggc   3300
ttaagtaaac caattgcttt agcccttgat agcaggctgg gcaagctctt tgggctgat   3360
tcagatctcc ggcgaattga aagcagtgat ctctcaggtg ctaaccggat agtattagaa   3420
gactccaata tcttgcagcc tgtgggactt actgtgtttg aaaactggct ctattggatt   3480
gataaacagc agcaaatgat tgaaaaaatt gacatgacag tcgagaggg tagaaccaaa   3540
gtccaagctc gaattgccca gcttagtgac attcatgcag taaggagct gaaccttcaa   3600
gaatacagac agcacccttg tgctcaggat aatggtggct gttcacatat ttgtcttgta   3660
aagggggatg gtactacaag gtgttcttgc cccatgcacc tggttctact tcaagatgag   3720
ctatcatgtg gagaacctcc aacatgttct cctcagcagt ttacttgttt cacggggaa   3780
```

```
attgactgta tccctgtggc ttggcggtgc gatgggttta ctgaatgtga agaccacagt    3840
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgctttgttt aattgatcag ttccgctgtg ccaatggtca gtgcattgga    4020
aagcacaaga gtgtgatca taatgtggat tgcagtgaca agtcagatga actggattgt    4080
tatccgactg aagaaccagc accacaggcc accaatacag ttggttctgt tattggcgta    4140
attgtcacca tttttgtgtc tggaactgta tactttatct gccagaggat gttgtgtcca    4200
cgtatgaagg gagatgggga aactatgact aatgactatg tagttcatgg accagcttct    4260
gtgcctcttg gttatgtgcc acacccaagt tctttgtcag gatctcttcc aggaatgtct    4320
cgaggtaaat caatgatcag ctccctcagt atcatggggg gaagcagtgg accccccctat   4380
gaccgagccc atgttacagg agcatcatca gtagttctt caagcaccaa aggcacttac     4440
ttccctgcaa ttttgaaccc tccaccatcc ccagccacag agcgatcaca ttacactatg    4500
gaatttggat attcttcaaa cagtccttcc actcataggt catacagcta caggccatat    4560
agctaccggc actttgcacc ccccaccaca ccctgcagca cagatgtttg tgacagtgac    4620
tatgctccta gtcggagaat gacctcagtg gcaacagcca agggctatac cagtgacttg    4680
aactatgatt cagaacctgt gccccccacct cccacacccc gaagccaata cttgtcagca   4740
gaggagaact atgaaagctg cccaccttct ccatacacag agaggagcta ttctcatcac    4800
ctctacccac cgccaccctc tccctgtaca gactcctcct ga                      4842
```

<210> SEQ ID NO 5  
<211> LENGTH: 262  
<212> TYPE: PRT  
<213> ORGANISM: Artificial Sequence  
<220> FEATURE:  
<223> OTHER INFORMATION: MGN 1004

<400> SEQUENCE: 5

Met Lys Trp Val Thr Phe Leu Leu Leu Phe Ile Ser Gly Ser Ala
1               5                   10                  15

Phe Ser His His His His His His His Gln Thr Leu Asn Ser Val
                20                  25                  30

Leu Asn Ser Asn Ala Ile Lys Asn Leu Pro Pro Leu Gly Gly Ala
            35                  40                  45

Ala Gly His Pro Gly Ser Ala Val Ser Ala Pro Gly Ile Leu Tyr
        50                  55                  60

Pro Gly Gly Asn Lys Tyr Gln Thr Ile Asp Asn Tyr Gln Pro Tyr
65                  70                  75                  80

Cys Ala Glu Asp Glu Glu Cys Gly Thr Asp Glu Tyr Cys Ala Ser Pro
                85                  90                  95

Thr Arg Gly Gly Asp Ala Gly Val Gln Ile Cys Leu Ala Cys Arg Lys
                100                 105                 110

Arg Arg Lys Arg Cys Met Arg His Ala Met Cys Cys Pro Gly Asn Tyr
            115                 120                 125

Cys Lys Asn Gly Ile Cys Val Ser Ser Asp Gln Asn His Phe Arg Gly
        130                 135                 140

Glu Ile Glu Glu Thr Ile Thr Glu Ser Phe Gly Asn Asp His Ser Thr
145                 150                 155                 160

Leu Asp Gly Tyr Ser Arg Arg Thr Thr Leu Ser Ser Lys Met Tyr His
                165                 170                 175

```
Thr Lys Gly Gln Glu Gly Ser Val Cys Leu Arg Ser Ser Asp Cys Ala
            180                 185                 190

Ser Gly Leu Cys Cys Ala Arg His Phe Trp Ser Lys Ile Cys Lys Pro
        195                 200                 205

Val Leu Lys Glu Gly Gln Val Cys Thr Lys His Arg Arg Lys Gly Ser
    210                 215                 220

His Gly Leu Glu Ile Phe Gln Arg Cys Tyr Cys Gly Glu Gly Leu Ser
225                 230                 235                 240

Cys Arg Ile Gln Lys Asp His His Gln Ala Ser Asn Ser Ser Arg Leu
                245                 250                 255

His Thr Cys Gln Arg His
            260

<210> SEQ ID NO 6
<211> LENGTH: 116
<212> TYPE: PRT
<213> ORGANISM: Artificial Sequence
<220> FEATURE:
<223> OTHER INFORMATION: MGN 1005

<400> SEQUENCE: 6

Met Lys Trp Val Thr Phe Leu Leu Leu Phe Ile Ser Gly Ser Ala
1               5                   10                  15

Phe Ser His His His His His His His Gln Met Tyr His Thr Lys
                20                  25                  30

Gly Gln Glu Gly Ser Val Cys Leu Arg Ser Ser Asp Cys Ala Ser Gly
            35                  40                  45

Leu Cys Cys Ala Arg His Phe Trp Ser Lys Ile Cys Lys Pro Val Leu
50                  55                  60

Lys Glu Gly Gln Val Cys Thr Lys His Arg Arg Lys Gly Ser His Gly
65                  70                  75                  80

Leu Glu Ile Phe Gln Arg Cys Tyr Cys Gly Glu Gly Leu Ser Cys Arg
                85                  90                  95

Ile Gln Lys Asp His His Gln Ala Ser Asn Ser Ser Arg Leu His Thr
            100                 105                 110

Cys Gln Arg His
        115

<210> SEQ ID NO 7
<211> LENGTH: 268
<212> TYPE: PRT
<213> ORGANISM: Artificial Sequence
<220> FEATURE:
<223> OTHER INFORMATION: MGN 1006

<400> SEQUENCE: 7

Met Lys Trp Val Thr Phe Leu Leu Leu Phe Ile Ser Gly Ser Ala
1               5                   10                  15

Phe Ser His His His His His His His Gln Thr Leu Asn Ser Val
                20                  25                  30

Leu Ile Asn Ser Asn Ala Ile Lys Asn Leu Pro Pro Leu Gly Gly
            35                  40                  45

Ala Gly Gly Gln Pro Gly Ser Ala Val Ser Val Ala Pro Gly Val Leu
50                  55                  60

Tyr Glu Gly Gly Asn Lys Tyr Gln Thr Leu Asp Asn Tyr Gln Pro Tyr
65                  70                  75                  80

Pro Cys Ala Glu Asp Glu Glu Cys Gly Ser Asp Glu Tyr Cys Ser Ser
```

```
                    85                  90                  95

Pro Ser Arg Gly Ala Ala Gly Val Gly Val Gln Ile Cys Leu Ala
            100                 105                 110

Cys Arg Lys Arg Lys Arg Cys Met Arg His Ala Met Cys Cys Pro
        115                 120                 125

Gly Asn Tyr Cys Lys Asn Gly Ile Cys Met Pro Ser Asp His Ser His
    130                 135                 140

Phe Pro Arg Gly Glu Ile Glu Glu Ser Ile Ile Glu Asn Leu Gly Asn
145                 150                 155                 160

Asp His Asn Ala Ala Ala Gly Asp Gly Tyr Pro Arg Arg Thr Thr Leu
                165                 170                 175

Thr Ser Lys Ile Tyr His Thr Lys Gly Gln Glu Gly Ser Val Cys Leu
            180                 185                 190

Arg Ser Ser Asp Cys Ala Ala Gly Leu Cys Cys Ala Arg His Phe Trp
        195                 200                 205

Ser Lys Ile Cys Lys Pro Val Leu Lys Glu Gly Gln Val Cys Thr Lys
    210                 215                 220

His Lys Arg Lys Gly Ser His Gly Leu Glu Ile Phe Gln Arg Cys Tyr
225                 230                 235                 240

Cys Gly Glu Gly Leu Ala Cys Arg Ile Gln Lys Asp His His Gln Ala
                245                 250                 255

Ser Asn Ser Ser Arg Leu His Thr Cys Gln Arg His
                260                 265

<210> SEQ ID NO 8
<211> LENGTH: 116
<212> TYPE: PRT
<213> ORGANISM: Artificial Sequence
<220> FEATURE:
<223> OTHER INFORMATION: MGN 1007

<400> SEQUENCE: 8

Met Lys Trp Val Thr Phe Leu Leu Leu Leu Phe Ile Ser Gly Ser Ala
1               5                   10                  15

Phe Ser His His His His His His His Gln Ile Tyr His Thr Lys
            20                  25                  30

Gly Gln Glu Gly Ser Val Cys Leu Arg Ser Ser Asp Cys Ala Ala Gly
        35                  40                  45

Leu Cys Cys Ala Arg His Phe Trp Ser Lys Ile Cys Lys Pro Val Leu
    50                  55                  60

Lys Glu Gly Gln Val Cys Thr Lys His Lys Arg Lys Gly Ser His Gly
65                  70                  75                  80

Leu Glu Ile Phe Gln Arg Cys Tyr Cys Gly Glu Gly Leu Ala Cys Arg
                85                  90                  95

Ile Gln Lys Asp His His Gln Ala Ser Asn Ser Ser Arg Leu His Thr
            100                 105                 110

Cys Gln Arg His
        115

<210> SEQ ID NO 9
<211> LENGTH: 266
<212> TYPE: PRT
<213> ORGANISM: Homo sapiens

<400> SEQUENCE: 9

Met Met Ala Leu Gly Ala Ala Gly Ala Thr Arg Val Phe Val Ala Met
1               5                   10                  15
```

```
Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 10
<211> LENGTH: 272
<212> TYPE: PRT
<213> ORGANISM: Mus musculus

<400> SEQUENCE: 10

Met Met Val Val Cys Ala Ala Ala Val Arg Phe Leu Ala Val Phe
1               5                   10                  15

Thr Met Met Ala Leu Cys Ser Leu Pro Leu Leu Gly Ala Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95

Tyr Cys Ser Ser Pro Ser Arg Gly Ala Ala Gly Val Gly Gly Val Gln
            100                 105                 110

Ile Cys Leu Ala Cys Arg Lys Arg Arg Lys Arg Cys Met Arg His Ala
```

|  | 115 |  |  | 120 |  |  | 125 |  |  |  |  |
|---|---|---|---|---|---|---|---|---|---|---|---|
| Met | Cys | Cys | Pro | Gly | Asn | Tyr | Cys | Lys | Asn | Gly | Ile | Cys | Met | Pro | Ser |
|  |  | 130 |  |  |  | 135 |  |  |  | 140 |  |  |  |  |  |

Met Cys Cys Pro Gly Asn Tyr Cys Lys Asn Gly Ile Cys Met Pro Ser
            130                 135                 140

Asp His Ser His Phe Pro Arg Gly Glu Ile Glu Ser Ile Ile Glu
145                 150                 155                 160

Asn Leu Gly Asn Asp His Asn Ala Ala Gly Asp Gly Tyr Pro Arg
                165                 170                 175

Arg Thr Thr Leu Thr Ser Lys Ile Tyr His Thr Lys Gly Gln Glu Gly
                180                 185                 190

Ser Val Cys Leu Arg Ser Ser Asp Cys Ala Ala Gly Leu Cys Cys Ala
                195                 200                 205

Arg His Phe Trp Ser Lys Ile Cys Lys Pro Val Leu Lys Glu Gly Gln
            210                 215                 220

Val Cys Thr Lys His Lys Arg Lys Gly Ser His Gly Leu Glu Ile Phe
225                 230                 235                 240

Gln Arg Cys Tyr Cys Gly Glu Gly Leu Ala Cys Arg Ile Gln Lys Asp
                245                 250                 255

His His Gln Ala Ser Asn Ser Ser Arg Leu His Thr Cys Gln Arg His
            260                 265                 270

<210> SEQ ID NO 11
<211> LENGTH: 789
<212> TYPE: DNA
<213> ORGANISM: Artificial Sequence
<220> FEATURE:
<223> OTHER INFORMATION: MGN 1004

<400> SEQUENCE: 11

```
atgaaatggg tgacctttct cctgctgctg ttcatcagcg ctccgctttt agccaccat     60
caccatcacc accaccacca gaccctgaac tccgtcctca acagcaacgc catcaagaat   120
ctccctcctc ctctcggagg cgctgctgga catcctggat ccgctgtgtc cgccgctcct   180
ggaatcctgt accccggcgg caacaagtac cagaccattg acaactacca gcctaccct   240
tgcgccgagg acgaggaatg cggcaccgat gagtactgcg cctcccctac aaggggagga   300
gatgccggcg tgcaaatctg cctggcctgc aggaagagga ggaagaggtg catgaggcac   360
gccatgtgct gccccggcaa ctactgcaag aacggcatct cgtcagctc cgatcagaac   420
catttcaggg gcgagatcga ggagaccatc accgagagct cggcaacga ccacagcacc   480
ctggacggct actccaggag gaccaccctc agcagcaaga tgtaccacac aaagggccag   540
gagggcagcg tgtgtctgag gagctccgac tgtgccagcg gcctctgttg tgccaggcac   600
ttttggagca agatctgcaa gcccgtgctc aaggagggcc aggtgtgcac caagcacagg   660
aggaaaggca gccacggcct cgagatcttc cagaggtgct actgcggaga gggcctctcc   720
tgcaggatcc agaaagacca ccaccaggct agcaacagca gcaggctgca cacctgtcag   780
aggcactga                                                           789
```

<210> SEQ ID NO 12
<211> LENGTH: 351
<212> TYPE: DNA
<213> ORGANISM: Artificial Sequence
<220> FEATURE:
<223> OTHER INFORMATION: MGN 1005

<400> SEQUENCE: 12

```
atgaagtggg tgaccttcct cctgctgctc ttcatctccg gcagcgcttt ctcccaccac     60
```

| | |
|---|---|
| caccatcacc accaccacca gatgtaccac acaaagggcc aggagggcag cgtgtgtctg | 120 |
| aggagctccg actgtgccag cggcctctgt tgtgccaggc acttttggag caagatctgc | 180 |
| aagcccgtgc tcaaggaggg ccaggtgtgc accaagcaca ggaggaaagg cagccacggc | 240 |
| ctcgagatct tccagaggtg ctactgcgga gagggcctct cctgcaggat ccagaaagac | 300 |
| caccaccagg ctagcaacag cagcaggctg cacacctgtc agaggcactg a | 351 |

<210> SEQ ID NO 13
<211> LENGTH: 807
<212> TYPE: DNA
<213> ORGANISM: Artificial Sequence
<220> FEATURE:
<223> OTHER INFORMATION: MGN 1006

<400> SEQUENCE: 13

| | |
|---|---|
| atgaaatggg tcaccttcct gctgctcctc ttcatctccg gctccgcttt tagccaccat | 60 |
| caccatcacc accaccacca gaccctgaac agcgtcctca tcaacagcaa cgctatcaag | 120 |
| aatctccctc ctcctctggg aggagctggc ggacaacctg gaagcgctgt gagcgtggct | 180 |
| cccggagtgc tctacgaagg cggcaacaag taccagaccc tggacaacta ccagccctac | 240 |
| ccttgtgccg aggacgaaga gtgcggctcc gacgagtatt gcagcagccc ttccagagga | 300 |
| gctgccggag tcggaggagt gcagatctgt ctcgcctgca gaaagaggag gaagaggtgc | 360 |
| atgaggcacg ccatgtgttg ccccggcaac tactgcaaaa atggcatctg catgccctcc | 420 |
| gatcacagcc atttccccag gggcgagatc gaggagagca tcatcgagaa cctgggcaac | 480 |
| gaccataatg ccgccgctgg agacggatac cctaggagga ccaccctcac cagcaagatc | 540 |
| taccacacca agggacagga gggcagcgtc tgcctcagga gcagcgattg cgctgctggc | 600 |
| ctctgctgtg ccaggcattt ctggagcaag atctgcaagc ccgtcctgaa ggagggccag | 660 |
| gtctgcacca agcataagag gaagggcagc cacggcctgg agatcttcca gagatgctac | 720 |
| tgtggcgagg gcctggcctg caggatccag aaagaccacc accaggccag caacagcagc | 780 |
| aggctgcaca cctgccagag acactga | 807 |

<210> SEQ ID NO 14
<211> LENGTH: 351
<212> TYPE: DNA
<213> ORGANISM: Artificial Sequence
<220> FEATURE:
<223> OTHER INFORMATION: MGN 1007

<400> SEQUENCE: 14

| | |
|---|---|
| atgaagtggg tgaccttcct cctgctgctc ttcatctccg gcagcgcttt ctcccaccac | 60 |
| caccatcacc accaccacca gatctaccac accaagggcc aggagggcag cgtgtgcctc | 120 |
| aggagcagcg attgcgctgc tggcctctgc tgtgccaggc atttctggag caagatctgc | 180 |
| aagcccgtcc tgaaggaggg ccaggtctgc accaagcata agaggaaggg cagccacggc | 240 |
| ctggagatct tccagagatg ctactgtggc gagggcctgg cctgcaggat ccagaaagac | 300 |
| caccaccagg ccagcaacag cagcaggctg cacacctgcc agagacactg a | 351 |

<210> SEQ ID NO 15
<211> LENGTH: 801
<212> TYPE: DNA
<213> ORGANISM: Homo sapiens

<400> SEQUENCE: 15

| | |
|---|---|
| atgatggctc tgggcgcagc gggagctacc cgggtctttg tcgcgatggt agcggcggct | 60 |

```
ctcggcggcc accctctgct gggagtgagc gccaccttga actcggttct caattccaac      120
gctatcaaga acctgccccc accgctgggc ggcgctgcgg ggcacccagg ctctgcagtc      180
agcgccgcgc cgggaatcct gtacccgggc gggaataagt accagaccat tgacaactac      240
cagccgtacc cgtgcgcaga ggacgaggag tgcggcactg atgagtactg cgctagtccc      300
acccgcggag gggacgcagg cgtgcaaatc tgtctcgcct gcaggaagcg ccgaaaacgc      360
tgcatgcgtc acgctatgtg ctgccccggg aattactgca aaatggaat atgtgtgtct      420 tctgatcaaa atcatttccg aggagaaatt gaggaaacca tcactgaaag ctttggtaat      480
gatcatagca ccttggatgg gtattccaga gaaccacct tgtcttcaaa aatgtatcac      540
accaaaggac aagaaggttc tgtttgtctc cggtcatcag actgtgcctc aggattgtgt      600
tgtgctagac acttctggtc caagatctgt aaacctgtcc tgaaagaagg tcaagtgtgt      660
accaagcata ggagaaaagg ctctcatgga ctagaaatat ccagcgttg ttactgtgga      720 gaaggtctgt cttgccggat acagaaagat caccatcaag ccagtaattc ttctaggctt      780
cacacttgtc agagacacta a                                                801

<210> SEQ ID NO 16
<211> LENGTH: 331
<212> TYPE: PRT
<213> ORGANISM: Homo sapiens

<400> SEQUENCE: 16

Pro Leu Leu Leu Leu Leu Leu Leu Ala Leu Cys Gly Cys Pro
1               5                   10                  15

Ala Pro Ala Ala Ala Ser Pro Leu Leu Leu Phe Ala Asn Arg Arg Asp
                20                  25                  30

Val Arg Leu Val Asp Ala Gly Gly Val Lys Leu Glu Ser Thr Ile Val
            35                  40                  45

Val Ser Gly Leu Glu Asp Ala Ala Ala Val Asp Phe Gln Phe Ser Lys
        50                  55                  60

Gly Ala Val Tyr Trp Thr Asp Val Ser Glu Glu Ala Ile Lys Gln Thr
65                  70                  75                  80

Tyr Leu Asn Gln Thr Gly Ala Ala Val Gln Asn Val Val Ile Ser Gly
                85                  90                  95

Leu Val Ser Pro Asp Gly Leu Ala Cys Asp Trp Val Gly Lys Lys Leu
            100                 105                 110

Tyr Trp Thr Asp Ser Glu Thr Asn Arg Ile Glu Val Ala Asn Leu Asn
        115                 120                 125

Gly Thr Ser Arg Lys Val Leu Phe Trp Gln Asp Leu Asp Gln Pro Arg
    130                 135                 140

Ala Ile Ala Leu Asp Pro Ala His Gly Tyr Met Tyr Trp Thr Asp Trp
145                 150                 155                 160

Gly Glu Thr Pro Arg Ile Glu Arg Ala Gly Met Asp Gly Ser Thr Arg
                165                 170                 175

Lys Ile Ile Val Asp Ser Asp Ile Tyr Trp Pro Asn Gly Leu Thr Ile
            180                 185                 190

Asp Leu Glu Glu Gln Lys Leu Tyr Trp Ala Asp Ala Lys Leu Ser Phe
        195                 200                 205

Ile His Arg Ala Asn Leu Asp Gly Ser Phe Arg Gln Lys Val Val Glu
    210                 215                 220

Gly Ser Leu Thr His Pro Phe Ala Leu Thr Leu Ser Gly Asp Thr Leu
225                 230                 235                 240
```

```
Tyr Trp Thr Asp Trp Gln Thr Arg Ser Ile His Ala Cys Asn Lys Arg
                245                 250                 255

Thr Gly Gly Lys Arg Lys Glu Ile Leu Ser Ala Leu Tyr Ser Pro Met
            260                 265                 270

Asp Ile Gln Val Leu Ser Gln Glu Arg Gln Pro Phe Phe His Thr Arg
        275                 280                 285

Cys Glu Glu Asp Asn Gly Gly Cys Ser His Leu Cys Leu Leu Ser Pro
    290                 295                 300

Ser Glu Pro Phe Tyr Thr Cys Ala Cys Pro Thr Gly Val Gln Leu Gln
305                 310                 315                 320

Asp Asn Gly Arg Thr Cys Lys Ala Gly Ala Glu
                325                 330

<210> SEQ ID NO 17
<211> LENGTH: 302
<212> TYPE: PRT
<213> ORGANISM: Homo sapiens

<400> SEQUENCE: 17

Pro Glu Ala Phe Leu Val Phe Thr Ser Arg Ala Ala Ile His Arg Ile
1               5                   10                  15

Ser Leu Glu Thr Asn Asn Asp Val Ala Ile Pro Leu Thr Gly Val
            20                  25                  30

Lys Glu Ala Ser Ala Leu Asp Phe Asp Val Ser Asn His Ile Tyr
            35                  40                  45

Trp Thr Asp Val Ser Leu Lys Thr Ile Ser Arg Ala Phe Met Asn Gly
50                  55                  60

Ser Ser Val Glu His Val Val Glu Phe Gly Leu Asp Tyr Pro Glu Gly
65                  70                  75                  80

Met Ala Val Asp Trp Met Gly Lys Asn Leu Tyr Trp Ala Asp Thr Gly
                85                  90                  95

Thr Asn Arg Ile Glu Val Ala Arg Leu Asp Gly Gln Phe Arg Gln Val
                100                 105                 110

Leu Val Trp Arg Asp Leu Asp Asn Pro Arg Ser Leu Ala Leu Asp Pro
            115                 120                 125

Thr Lys Gly Tyr Ile Tyr Trp Thr Glu Trp Gly Gly Lys Pro Arg Ile
    130                 135                 140

Val Arg Ala Phe Met Asp Gly Thr Asn Cys Met Thr Leu Val Asp Lys
145                 150                 155                 160

Val Gly Arg Ala Asn Asp Leu Thr Ile Asp Tyr Ala Asp Gln Arg Leu
                165                 170                 175

Tyr Trp Thr Asp Leu Asp Thr Asn Met Ile Glu Ser Ser Asn Met Leu
                180                 185                 190

Gly Gln Glu Arg Val Val Ile Ala Asp Asp Leu Pro His Pro Phe Gly
            195                 200                 205

Leu Thr Gln Tyr Ser Asp Tyr Ile Tyr Trp Thr Asp Trp Asn Leu His
    210                 215                 220

Ser Ile Glu Arg Ala Asp Lys Thr Ser Gly Arg Asn Arg Thr Leu Ile
225                 230                 235                 240

Gln Gly His Leu Asp Phe Val Met Asp Ile Leu Val Phe His Ser Ser
                245                 250                 255

Arg Gln Asp Gly Leu Asn Asp Cys Met His Asn Asn Gly Gln Cys Gly
            260                 265                 270

Gln Leu Cys Leu Ala Ile Pro Gly Gly His Arg Cys Gly Cys Ala Ser
```

```
                    275                 280                 285
His Tyr Thr Leu Asp Pro Ser Ser Arg Asn Cys Ser Pro Pro
    290                 295                 300

<210> SEQ ID NO 18
<211> LENGTH: 308
<212> TYPE: PRT
<213> ORGANISM: Homo sapiens

<400> SEQUENCE: 18

Pro Leu Leu Leu Tyr Ala Asn Arg Arg Asp Leu Arg Leu Val Asp Ala
1               5                   10                  15

Thr Asn Gly Lys Glu Asn Ala Thr Ile Val Val Gly Gly Leu Glu Asp
            20                  25                  30

Ala Ala Ala Val Asp Phe Val Phe Ser His Gly Leu Ile Tyr Trp Ser
        35                  40                  45

Asp Val Ser Glu Glu Ala Ile Lys Arg Thr Glu Phe Asn Lys Thr Glu
    50                  55                  60

Ser Val Gln Asn Val Val Val Ser Gly Leu Leu Ser Pro Asp Gly Leu
65                  70                  75                  80

Ala Cys Asp Trp Leu Gly Glu Lys Leu Tyr Trp Thr Asp Ser Glu Thr
                85                  90                  95

Asn Arg Ile Glu Val Ser Asn Leu Asp Gly Ser Leu Arg Lys Val Leu
            100                 105                 110

Phe Trp Gln Glu Leu Asp Gln Pro Arg Ala Ile Ala Leu Asp Pro Ser
        115                 120                 125

Ser Gly Phe Met Tyr Trp Thr Asp Trp Gly Glu Val Pro Lys Ile Glu
    130                 135                 140

Arg Ala Gly Met Asp Gly Ser Ser Arg Phe Ile Ile Ile Asn Ser Glu
145                 150                 155                 160

Ile Tyr Trp Pro Asn Gly Leu Thr Leu Asp Tyr Glu Glu Gln Lys Leu
                165                 170                 175

Tyr Trp Ala Asp Ala Lys Leu Asn Phe Ile His Lys Ser Asn Leu Asp
            180                 185                 190

Gly Thr Asn Arg Gln Ala Val Val Lys Gly Ser Leu Pro His Pro Phe
        195                 200                 205

Ala Leu Thr Leu Phe Glu Asp Ile Leu Tyr Trp Thr Asp Trp Ser Thr
    210                 215                 220

His Ser Ile Leu Ala Cys Asn Lys Tyr Thr Gly Glu Gly Leu Arg Glu
225                 230                 235                 240

Ile His Ser Asp Ile Phe Ser Pro Met Asp Ile His Ala Phe Ser Gln
                245                 250                 255

Gln Arg Gln Pro Asn Ala Thr Asn Pro Cys Gly Ile Asp Asn Gly Gly
            260                 265                 270

Cys Ser His Leu Cys Leu Met Ser Pro Val Lys Pro Phe Tyr Gln Cys
        275                 280                 285

Ala Cys Pro Thr Gly Val Lys Leu Leu Glu Asn Gly Lys Thr Cys Lys
    290                 295                 300

Asp Gly Ala Thr
305

<210> SEQ ID NO 19
<211> LENGTH: 303
<212> TYPE: PRT
<213> ORGANISM: Homo sapiens
```

<400> SEQUENCE: 19

```
Pro Glu Ala Phe Leu Leu Phe Ser Arg Arg Ala Asp Ile Arg Ile
1               5                   10                  15

Ser Leu Glu Thr Asn Asn Asn Val Ala Ile Pro Leu Thr Gly Val
            20                  25                  30

Lys Glu Ala Ser Ala Leu Asp Phe Asp Val Thr Asp Asn Arg Ile Tyr
            35                  40                  45

Trp Thr Asp Ile Ser Leu Lys Thr Ile Ser Arg Ala Phe Met Asn Gly
    50                  55                  60

Ser Ala Leu Glu His Val Val Glu Phe Gly Leu Asp Tyr Pro Glu Gly
65              70                  75                  80

Met Ala Val Asp Trp Leu Gly Lys Asn Leu Tyr Trp Ala Asp Thr Gly
                85                  90                  95

Thr Asn Arg Ile Glu Val Ser Lys Leu Asp Gly Gln His Arg Gln Val
                100                 105                 110

Leu Val Trp Lys Asp Leu Asp Ser Pro Arg Ala Leu Ala Leu Asp Pro
                115                 120                 125

Ala Glu Gly Phe Met Tyr Trp Thr Glu Trp Gly Gly Lys Pro Lys Ile
    130                 135                 140

Asp Arg Ala Ala Met Asp Gly Ser Glu Arg Thr Thr Leu Val Pro Asn
145                 150                 155                 160

Val Gly Arg Ala Asn Gly Leu Thr Ile Asp Tyr Ala Lys Arg Arg Leu
                165                 170                 175

Tyr Trp Thr Asp Leu Asp Thr Asn Leu Ile Glu Ser Ser Asn Met Leu
                180                 185                 190

Gly Leu Asn Arg Glu Val Ile Ala Asp Asp Leu Pro His Pro Phe Gly
            195                 200                 205

Leu Thr Gln Tyr Gln Asp Tyr Ile Tyr Trp Thr Asp Trp Ser Arg Arg
    210                 215                 220

Ser Ile Glu Arg Ala Asn Lys Thr Ser Gly Gln Asn Arg Thr Ile Ile
225                 230                 235                 240

Gln Gly His Leu Asp Tyr Val Met Asp Ile Leu Val Phe His Ser Ser
                245                 250                 255

Arg Gln Ser Gly Trp Asn Glu Cys Ala Ser Ser Asn Gly His Cys Ser
            260                 265                 270

His Leu Cys Leu Ala Val Pro Val Gly Gly Phe Val Cys Gly Cys Pro
            275                 280                 285

Ala His Tyr Ser Leu Asn Ala Asp Asn Arg Thr Cys Ser Ala Pro
    290                 295                 300
```

<210> SEQ ID NO 20
<211> LENGTH: 20
<212> TYPE: DNA
<213> ORGANISM: Artificial Sequence
<220> FEATURE:
<223> OTHER INFORMATION: Forward Primer - Acta2

<400> SEQUENCE: 20
ctgacagagg caccactgaa        20

<210> SEQ ID NO 21
<211> LENGTH: 20
<212> TYPE: DNA
<213> ORGANISM: Artificial Sequence
<220> FEATURE:
<223> OTHER INFORMATION: Reverse Primer - Acta2

```
<400> SEQUENCE: 21
catctccaga gtccagcaca                                              20

<210> SEQ ID NO 22
<211> LENGTH: 20
<212> TYPE: DNA
<213> ORGANISM: Artificial Sequence
<220> FEATURE:
<223> OTHER INFORMATION: Forward Primer - Axin2

<400> SEQUENCE: 22
taggcggaat gaagatggac                                              20

<210> SEQ ID NO 23
<211> LENGTH: 20
<212> TYPE: DNA
<213> ORGANISM: Artificial Sequence
<220> FEATURE:
<223> OTHER INFORMATION: Reverse Primer - Axin2

<400> SEQUENCE: 23
ctggtcaccc aacaaggagt                                              20

<210> SEQ ID NO 24
<211> LENGTH: 20
<212> TYPE: DNA
<213> ORGANISM: Artificial Sequence
<220> FEATURE:
<223> OTHER INFORMATION: Forward Primer - Col1a1

<400> SEQUENCE: 24
gagcggagag tactggatcg                                              20

<210> SEQ ID NO 25
<211> LENGTH: 20
<212> TYPE: DNA
<213> ORGANISM: Artificial Sequence
<220> FEATURE:
<223> OTHER INFORMATION: Reverse Primer - Col1a1

<400> SEQUENCE: 25
gttcgggctg atgtaccagt                                              20

<210> SEQ ID NO 26
<211> LENGTH: 20
<212> TYPE: DNA
<213> ORGANISM: Artificial Sequence
<220> FEATURE:
<223> OTHER INFORMATION: Forward Primer - Cspg4

<400> SEQUENCE: 26
agctgatgct ggaggtgtct                                              20

<210> SEQ ID NO 27
<211> LENGTH: 20
<212> TYPE: DNA
<213> ORGANISM: Artificial Sequence
<220> FEATURE:
<223> OTHER INFORMATION: Reverse Primer - Cspg4

<400> SEQUENCE: 27
gaagatgatg cgaggtggat                                              20

<210> SEQ ID NO 28
<211> LENGTH: 20
```

```
<212> TYPE: DNA
<213> ORGANISM: Artificial Sequence
<220> FEATURE:
<223> OTHER INFORMATION: Forward Primer - Ctgf

<400> SEQUENCE: 28
agcagctggg agaactgtgt                                                 20

<210> SEQ ID NO 29
<211> LENGTH: 20
<212> TYPE: DNA
<213> ORGANISM: Artificial Sequence
<220> FEATURE:
<223> OTHER INFORMATION: Reverse Primer - Ctgf

<400> SEQUENCE: 29
gctgctttgg aaggactcac                                                 20

<210> SEQ ID NO 30
<211> LENGTH: 20
<212> TYPE: DNA
<213> ORGANISM: Artificial Sequence
<220> FEATURE:
<223> OTHER INFORMATION: Forward Primer - Dkk1

<400> SEQUENCE: 30 gagggggaaat tgaggaaagc                                                20

<210> SEQ ID NO 31
<211> LENGTH: 20
<212> TYPE: DNA
<213> ORGANISM: Artificial Sequence
<220> FEATURE:
<223> OTHER INFORMATION: Reverse Primer - Dkk1

<400> SEQUENCE: 31
acggagcctt cttgtccttt                                                 20

<210> SEQ ID NO 32
<211> LENGTH: 20
<212> TYPE: DNA
<213> ORGANISM: Artificial Sequence
<220> FEATURE:
<223> OTHER INFORMATION: Forward Primer - Dkk2

<400> SEQUENCE: 32 caggggggaag tctgtaccaa                                                20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer - Dkk2

<400> SEQUENCE: 33
ggtggcatct ttccacactt                                                 20

<210> SEQ ID NO 34
<211> LENGTH: 20
<212> TYPE: DNA
<213> ORGANISM: Artificial Sequence
<220> FEATURE:
<223> OTHER INFORMATION: Forward Primer - Dkk3

<400> SEQUENCE: 34
```
accagagtgg acaggtggtc                                              20

<210> SEQ ID NO 35
<211> LENGTH: 20
<212> TYPE: DNA
<213> ORGANISM: Artificial Sequence
<220> FEATURE:
<223> OTHER INFORMATION: Reverse Primer - Dkk3

<400> SEQUENCE: 35
ggcggagact cttcatcaat                                              20

<210> SEQ ID NO 36
<211> LENGTH: 20
<212> TYPE: DNA
<213> ORGANISM: Artificial Sequence
<220> FEATURE:
<223> OTHER INFORMATION: Forward Primer - Fgf2

<400> SEQUENCE: 36
caccaactgc accaatgaac                                              20

<210> SEQ ID NO 37
<211> LENGTH: 20
<212> TYPE: DNA
<213> ORGANISM: Artificial Sequence
<220> FEATURE:
<223> OTHER INFORMATION: Reverse Primer - Fgf2

<400> SEQUENCE: 37
ggctgggtga gatccaagta                                              20

<210> SEQ ID NO 38
<211> LENGTH: 20
<212> TYPE: DNA
<213> ORGANISM: Artificial Sequence
<220> FEATURE:
<223> OTHER INFORMATION: Forward Primer - Fgf23

<400> SEQUENCE: 38
tgctagggac ctgccttaga                                              20

<210> SEQ ID NO 39
<211> LENGTH: 20
<212> TYPE: DNA
<213> ORGANISM: Artificial Sequence
<220> FEATURE:
<223> OTHER INFORMATION: Reverse Primer - Fgf23

<400> SEQUENCE: 39
gtacaggtgg gtcaggcttc                                              20

<210> SEQ ID NO 40
<211> LENGTH: 20
<212> TYPE: DNA
<213> ORGANISM: Artificial Sequence
<220> FEATURE:
<223> OTHER INFORMATION: Forward Primer - Kim1

<400> SEQUENCE: 40
aggaagaccc acggctattt                                              20

<210> SEQ ID NO 41
<211> LENGTH: 20
<212> TYPE: DNA
<213> ORGANISM: Artificial Sequence

```
<220> FEATURE:
<223> OTHER INFORMATION: Reverse Primer - Kim1

<400> SEQUENCE: 41
tgtcacagtg ccattccagt                                               20

<210> SEQ ID NO 42
<211> LENGTH: 19
<212> TYPE: DNA
<213> ORGANISM: Artificial Sequence
<220> FEATURE:
<223> OTHER INFORMATION: Forward Primer - Lngfr

<400> SEQUENCE: 42
caaggagaca tgttccaca                                                19

<210> SEQ ID NO 43
<211> LENGTH: 20
<212> TYPE: DNA
<213> ORGANISM: Artificial Sequence
<220> FEATURE:
<223> OTHER INFORMATION: Reverse Primer - Lngfr

<400> SEQUENCE: 43
accacgtcag agaacgtaac                                               20

<210> SEQ ID NO 44
<211> LENGTH: 20
<212> TYPE: DNA
<213> ORGANISM: Artificial Sequence
<220> FEATURE:
<223> OTHER INFORMATION: Forward Primer - Pdgfrb

<400> SEQUENCE: 44
caccttctcc agtgtgctga                                               20

<210> SEQ ID NO 45
<211> LENGTH: 20
<212> TYPE: DNA
<213> ORGANISM: Artificial Sequence
<220> FEATURE:
<223> OTHER INFORMATION: Reverse Primer - Pdgfrb

<400> SEQUENCE: 45
ggagtccata gggaggaagc                                               20

<210> SEQ ID NO 46
<211> LENGTH: 20
<212> TYPE: DNA
<213> ORGANISM: Artificial Sequence
<220> FEATURE:
<223> OTHER INFORMATION: Forward Primer - sFrp4

<400> SEQUENCE: 46
caccacagca ctcaggagaa                                               20

<210> SEQ ID NO 47
<211> LENGTH: 20
<212> TYPE: DNA
<213> ORGANISM: Artificial Sequence
<220> FEATURE:
<223> OTHER INFORMATION: Reverse Primer - sFrp4

<400> SEQUENCE: 47
acagacttgc agggcttgat                                               20
```

<210> SEQ ID NO 48
<211> LENGTH: 21
<212> TYPE: DNA
<213> ORGANISM: Artificial Sequence
<220> FEATURE:
<223> OTHER INFORMATION: Forward Primer - sFlt1

<400> SEQUENCE: 48
atgcgctgca gagccaggaa c                                              21

<210> SEQ ID NO 49
<211> LENGTH: 20
<212> TYPE: DNA
<213> ORGANISM: Artificial Sequence
<220> FEATURE:
<223> OTHER INFORMATION: Reverse Primer - sFlt1

<400> SEQUENCE: 49
ggtacaatca ttcctcctgc                                                20

<210> SEQ ID NO 50
<211> LENGTH: 22
<212> TYPE: DNA
<213> ORGANISM: Artificial Sequence
<220> FEATURE:
<223> OTHER INFORMATION: Forward Primer - Tgfb1

<400> SEQUENCE: 50
gaaggacctg ggttggaagt gg                                             22

<210> SEQ ID NO 51
<211> LENGTH: 22
<212> TYPE: DNA
<213> ORGANISM: Artificial Sequence
<220> FEATURE:
<223> OTHER INFORMATION: Reverse Primer - Tgfb1

<400> SEQUENCE: 51
cgtagtagac gatgggcagt gg                                             22

<210> SEQ ID NO 52
<211> LENGTH: 20
<212> TYPE: DNA
<213> ORGANISM: Artificial Sequence
<220> FEATURE:
<223> OTHER INFORMATION: Forward Primer - Wisp1

<400> SEQUENCE: 52
cccctacaag tccaagacca                                                20

<210> SEQ ID NO 53
<211> LENGTH: 20
<212> TYPE: DNA
<213> ORGANISM: Artificial Sequence
<220> FEATURE:
<223> OTHER INFORMATION: Reverse Primer - Wisp1

<400> SEQUENCE: 53
cgttaggatt cctgcagctc                                                20

<210> SEQ ID NO 54
<211> LENGTH: 19
<212> TYPE: DNA
<213> ORGANISM: Artificial Sequence
<220> FEATURE:
<223> OTHER INFORMATION: Primer -continued

```
<400> SEQUENCE: 54
aagttcatct gcaccaccg                                                    19

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tgctcaggta gtggttgtcg                                                   20

<210> SEQ ID NO 56
<211> LENGTH: 18
<212> TYPE: PRT
<213> ORGANISM: Rattus norvegicus

<400> SEQUENCE: 56

Met Lys Trp Val Thr Phe Leu Leu Leu Leu Phe Ile Ser Gly Ser Ala
1               5                   10                  15

Phe Ser
```

ADMINISTRATION OF DKK1 MUTEINS TO TREAT FIBROSIS

CROSS REFERENCE TO RELATED APPLICATION

This application is a national phase of PCT/US2013/068107 filed on Nov. 1, 2013 which claims priority to U.S. Provisional Patent Application No. 61/721,447 filed on Nov. 1, 2012 the entire contents of which are incorporated by reference herein.

STATEMENT OF GOVERNMENT INTEREST

This invention was made with government support under Grant Nos. RO1 DK084077 and DK087389, awarded by the National Institutes of Health. The government has certain rights in the invention.

FIELD OF THE DISCLOSURE

The present disclosure provides molecules, compositions and methods for treating scarring in organs. The molecules, compositions and methods treat scarring by modulating the WNT, platelet-derived growth factor receptor (PDGFR), transforming growth factor-beta (TGFβ) and/or connective-tissue growth factor (CTGF) signaling pathways.

BACKGROUND OF THE DISCLOSURE

Scarring of the organs is a major global health problem. Such scarring can be the consequence of subclinical injury to the organ over a period of time or the sequela of acute severe injury or inflammation.

All organs can be affected by scarring. Scarring provokes decline in organ function, inflammation and tissue ischemia. These effects may be directly due the deposition of fibrotic matrix which impairs organ function such as in contractility and relaxation of the heart and vasculature or impaired inflation and deflation of lungs, or by increasing the space between microvasculature and vital cells of the organ that are deprived of nutrients in a distorted tissue architecture. Currently there are few effective therapies that treat such scarring of organs.

SUMMARY OF THE DISCLOSURE

The current disclosure provides molecules, compositions and methods that treat scarring of organs. The molecules, compositions and methods treat scarring by modulating the WNT signaling pathway, including by down-regulating the WNT pathway. The compositions and methods can further treat scarring of organs by down-regulating pathways redundant to the WNT pathway including one or more of the platelet-derived growth factor receptor (PDGFR) pathway, the transforming growth factor-beta (TGFβ) pathway and/or the connective-tissue growth factor (CTGF) pathway. In particular embodiments, the composition and methods treat scarring by down-regulating the WNT, PDGFR, TGFβ and CTGF signaling pathways.

Modulation of the WNT, PDGFR, TGFβ and/or CTGF signaling pathways can occur based on the targeting of LRP5 and/or LRP6 receptors. Such targeting can occur through the administration of effective amounts of a molecule that targets LRP5 and/or LRP6 receptors directly or by the administration of nucleic acid sequences that express molecules that target LRP5 and/or LRP6 receptors. In particular embodiments, the LRP5 and/or LRP6 receptor targeting molecules include LRP5 and/or LRP6 receptor antibodies, molecules that alter the phosphorylation state of LRP5 and/or LRP6 receptors, and/or proteins that bind LRP5 and/or LRP6 receptors. Proteins that bind LRP5 and/or LRP6 receptors include, without limitation, Dickkopf-related proteins (DKKs), the WNT modulator in surface ectoderm (WISE) and sclerostin (SOST). The current disclosure focuses, but is not limited to the use of Dickkopf-related protein-1 (DKK1) and modified versions thereof. Each of the LRP5 and/or LRP6 receptor targeting molecules can be provided as individual targeting molecules or in combination with other LRP5 and/or LRP6 targeting molecules as part of a composition that includes pharmaceutically acceptable excipients.

BRIEF DESCRIPTION OF THE FIGURES

FIG. 4. Effect of DKK1 on kidney epithelial cell functions in vivo and in vitro. (A) Proliferating proximal kidney tubules, detected by co-expression of LTL and Ki67 in kidneys d4 after UUO surgery from mice treated with an adenovirus (Ad) which causes the liver to generate DKK1 and secrete it into the circulation (AdDKK1) or adenovirus which causes the liver to produce an inert protein, GFP (Adcontrol). (B) Expression of Kim1 transcripts in whole kidney RNA, d4 after UUO surgery from mice treated with AdDKK1 or Adcontrol. (C) Proliferating proximal tubules, detected by co-expression of LTL and Ki67 in kidneys d10 after U-IRI surgery from mice treated with AdDKK1 or Adcontrol. (D) Migration assay at 24 h on confluent primary mouse proximal tubule cells in the presence of cytokine combinations. (*P<0.05, **P<0.01, Experiments are from n=4-7/group).

FIG. 6. Western blots and normalized density graphs showing the effect of factors on low-density lipoprotein receptor LRP6 and other gene expression or phosphorylation in primary kidney pericyte cultures. (A) Time course of p-LRP6 or p-PDGFRβ in pericytes following PDGF-BB stimulation of PDGF-BB+DKK1 stimulation. (B) Graphs showing relative density of bands from 3 separate experiments performed as shown in FIG. 13F (C) The effect of DKK1 alone on p-LRP6, (D) Graphs showing relative density of bands from 3 separate experiments performed as shown in FIG. 13H. (E) The effect of WNT3a or WNT3a+DKK1 on p-LRP6 and CyclinD1 in kidney pericytes. ($*P<0.05$, $**P<0.01$, Experiments are from n=3-4/group).

FIG. 16. Protein sequence of LRP5 (SEQ ID NO. 1) with binding domains underlined.

FIG. 17. Protein sequence of LRP6 (SEQ ID NO. 2) with binding domains underlined.

FIG. 18. Nucleotide sequence encoding LRP5 (SEQ ID NO. 3) with portions coding for binding domains underlined.

FIG. 19. Nucleotide sequence encoding LRP6 (SEQ ID NO. 4) with portions coding for binding domains underlined.

FIG. 20. Sequences of engineered synthetic DKK1 constructs, MGN1004 (SEQ ID NO. 5; MGN1005 (SEQ ID NO. 6); MGN1006 (SEQ ID NO. 7); and MGN1007 (SEQ ID NO. 8).

FIG. 21. Sequences of native human (SEQ ID NO. 9) and mouse (SEQ ID NO.10) DKK1 gene transcripts.

FIG. 22. (A) Nucleotide sequence encoding MGN1004 (SEQ ID NO. 11); (B) Nucleotide sequence encoding MGN1005 (SEQ ID NO. 12); (C) Nucleotide sequence encoding MGN1006 (SEQ ID NO. 13); (D) Nucleotide sequence encoding MGN1007 (SEQ ID NO. 14) and (E) Nucleotide sequence encoding Human DKK1 (SEQ ID NO. 15).

FIG. 23. Coomassie stained gels loaded with Nickel column - - - purified, His - - - tag cleaved proteins, showing high levels of purity. Lane 1=reducing conditions and lane 2=non-reducing conditions (MGN1004; MGN1005; MGN1006; and MGN1007. For MGN1006 after freeze thaw Lane 1=prethaw reduced (lane1) compared with equal loading of post thaw reduced (lane 2) and unreduced (lane 3).

DETAILED DESCRIPTION

Fibrosis is the scarring process that occurs in organs, destroying the normal organ architecture, leading to loss of normal organ tissue and replacement with scar tissue. Fibrosis is a major pathological factor in many other diseases encompassing all major organ systems, and is strongly associated with as many as 45% of all natural deaths. Thus, therapies that counteract fibrosis, or the process of fibrogenesis, across different organs are urgently required as new treatments for diseases of liver, lung, heart, skin, pancreas, muscle, brain, intestine, eyes, bone marrow and large vessels.

Fibrosis can be the consequence of subclinical injury to an organ over a period of time or can result as the sequelae of acute severe injury or inflammation. All organs can be affected by fibrosis which matures into microscopic or macroscopic scarring within the tissue parenchyma. At present there are few therapies that specifically target the process of fibrogenesis, despite increasing evidence that suggests that fibrogenesis per se provokes further decline in organ function, inflammation and tissue ischemia (19-21).

Figure 1:
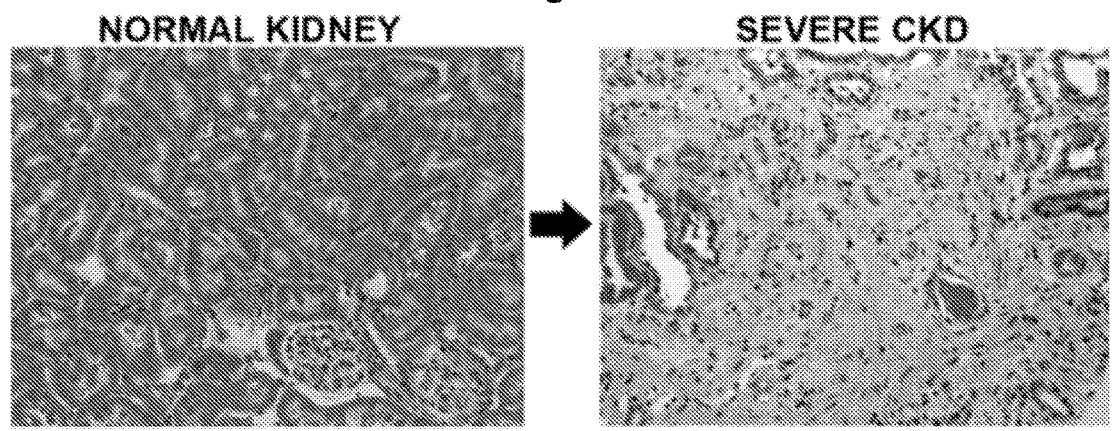
FIG. 1. Characteristic manifestations of chronic kidney disease (CKD). A stained image of kidney cortex from normal kidney and ischemic CKD showing marked expansion of interstitial fibrosis which has overtaken all of the tubules and microvasculature. Fibrotic material involves inflammatory cells and myofibroblasts. In CKD the remaining tubules all show tubular atrophy with intraluminal debris.

As an example, in the kidney, many diseases that trigger tissue damage lead ultimately to a progressive disease known as chronic kidney disease (CKD). (FIG. 1). CKD affects 26 million (1 in 12) US citizens and is a major cause of kidney failure. Other than supportive care, currently the only indicated treatment for CKD is angiotensin receptor blockade or angiotensin converting enzyme inhibitors. Their use, however has done little to stem the tide of patients progressing to kidney failure. Kidney failure requires dialysis or transplantation for survival. The dialysis program supports the survival of approximately 300,000 in the US but costs 20% of the entire Medicare budget. In addition CKD is now recognized as a major independent risk factor for cardiovascular events, including myocardial infarction and stroke, an effect amplified by increasing progression of CKD. There is, therefore, a massive unmet need for new therapeutics in this area.

Myofibroblasts are a cell type involved in the progression of organ scarring. Pericytes normally nurse, maintain and regulate the microvasculature (22, 23). Under certain physiological conditions, however, pericytes transition to myofibroblasts creating an unstable microvasculature leading to aberrant angiogenesis, or to rarefaction (23). These microvascular changes ultimately provoke tissue ischemia and scarring. Therefore myofibroblasts and the transition from pericytes to myofibroblasts present targets for therapeutics to counter the deleterious consequences of tissue injury.

One major regulatory pathway of myofibroblast activity is the WNT pathway. The current disclosure provides modulation of the WNT pathway as a mechanism to treat organ scarring. Recently, single nucleotide polymorphisms in LRP6, a transmembrane coreceptor for WNTs that bind to Frizzled receptors and thereby WNT/β-catenin signaling cascade have been identified as independent risk factors for the development of cardiovascular diseases. The WNT/β-catenin signaling pathway is a major regulator of cell function in both embryonic development and in adults. Both elevated and attenuated levels of signaling that fall outside of the normal homeostatic range of WNT signaling are linked to abnormal embryonic development and to diverse disease states (26). Increasing evidence indicates that WNT signaling plays critical roles in tissue regeneration and immune responses to injury and infection (27) However the signaling cascade and the cellular responses are complex and context specific. (28-30).

Because the WNT pathway shares several redundant intracellular signaling pathways, the current disclosure also provides modulation of one or more of these redundant pathways in addition to the WNT pathway. The current disclosure is further related to the discovery that the WNT co-receptors, low-density lipoprotein receptor (LRP)-5 and/or LRP6 are co-receptors for most cell signaling pathways involved in fibrosis, including the WNT, PDGF, TGFβ and CTGF pathways. Therefore, targeting LRP5 and/or LRP6 on cell surfaces is highly desirable because it leads to blockade of multiple myofibroblast activating pathways, avoiding the redundancy issues suffered by current individual pathway inhibitors. Such inhibition also blocks inflammatory cells (leukocyte) infiltration of the tissue.

Increasing evidence indicates that scarring mechanisms are similar across multiple organs. For example the cells that deposit fibrillar matrix that becomes scar tissue have been identified recently with more certainty. Similar (pericyte or fibroblast) cells across multiple organs including heart, skin muscle, brain, lung, liver and kidney have been shown to be the major cellular mechanism of fibrogenesis (54-61). In addition we have shown recently that the WNT pathway is highly activated in lung pericytes and fibroblasts and anticipate therefore that similar blockade of the WNT pathway in the equivalent cells will have beneficial consequences (58). Furthermore, there is increasing evidence for the role of recruited leukocytes, nearby epithelial cells and endothelial cells driving fibrogenesis by release of factors that will act on LRP5/6 receptors and the WNT pathway in local myofibroblasts and their progenitors.

Based on the foregoing, the molecules, compositions and methods to treat scarring are applicable across organ types. Particularly relevant organ types include the kidney liver, lung, heart, pericardium, skin, pancreas, muscle, brain/CNS, intestine, peritonieum, retroperitoneum, eye, bone marrow, joint, or large vessel.

Diseases or conditions that can be ameliorated by treating scarring according to the methods disclosed herein include, without limitation, CKD which can be based on, without limitation, diabetes mellitus, hypertension, arteriosclerosis, atherosclerosis, autoimmune diseases including, without limitation, lupus, anti-neutrophil cytoplasmic antibody (ANCA)-associated vasculitis, anti-glomerular basement membrane (GBM) disease, other glomerular diseases including focal segmental glomerular sclerosis (FSGS), IgA nephropathy, membranous nephropathy, genetic diseases including, without limitation, Alports Syndrome, polycystic kidney disease, kidney infections including urinary track infections (UTIs), viral or bacterial or parasite-related kidney disease, or CKD following xenobiotic exposure, sepsis or ischemic injuries; fibrosing lung diseases including, without limitation, idiopathic pulmonary fibrosis (IPF), chronic obstructive pulmonary disease (COPD), or asthma; fibrosing skin diseases including, without limitation, scleroderma; fibrosing heart diseases including, without limitation, ischemic cardiomyopathy and post myocardial infarction cardiac failure; fibrosing muscle diseases; fibrosing brain diseases including, without limitation, scarring of the brain following stroke; fibrosing gut diseases including, without limitation, associated with Crohns Colitis or other diseases with strictures; scarring of the peritoneum, as occurs in, without limitation, post surgical laparotomies; and scarring of the pancreas as occurs, without limitation, following pancreatitis.

A variety of molecules, compositions and methods can be used to modulate the WNT, PDGF, TGFβ and/or CTGF pathways and/or to target LRP5 and/or LRP6 receptors. For example, WNT signaling is regulated by various antagonists that include the Dickkopf-related proteins (DKKs), the WNT modulator in surface ectoderm (WISE) and sclerostrin (SOST). The current disclosure focuses, but is not limited to the use of Dickkopf-related protein-1 (DKK1). As will be understood by one of ordinary skill in the art, LRP5 and/or LRP6 receptor antibodies can also be used as well as other molecules that alter LRP5 and/or LRP6 receptor phosphorylation. DKK1 particularly and modified forms thereof act only on active signaling pathways, limiting potential side effects of its administration as a therapeutic to treat organ scarring in subjects. Modulation of the WNT PDGF, TGFβ and/or CTGF pathways can also be modulated by LRP5 and/or LRP6 targeting molecules that also bind to KREMEN receptors. Accordingly, KREMEN receptors and antibodies and molecules that bind KREMEN receptors are within the scope of the present disclosure.

As used herein, a "subject" includes, but is not limited to, an organism; a mammal, including, e.g., a human, non-human primate (e.g., baboon, orangutan, monkey), mouse, pig, cow, goat, cat, dog, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, "treat" or "treating" includes prophylactic treatments and therapeutic treatments.

As used herein, a "prophylactic treatment" includes a treatment administered to a subject who does not display signs or symptoms of a disease, pathology (such as scarring), or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder.

As used herein, a "therapeutic treatment" includes a treatment administered to a subject who displays symptoms or signs of a disease, pathology (such as scarring) or fibrogenesis or medical disorder, in which treatment is administered to the subject for the purpose of diminishing or eliminating those signs or symptoms of the disease, pathology or medical disorder.

As used herein, "scarring" is a term used interchangeably with fibrosis or sclerosis. It is the deposition of fibrillar matrix which undergoes contraction, between parenchymal structures and occurs in response to tissue injury. Fibrogenesis is a term which refers to the active cellular processes of depositing fibrotic or scar tissue.

The molecules and compositions disclosed herein are provided in effective amounts to treat scarring. The term "effective amount" means a dosage or amount sufficient to treat scarring. The desired result may comprise an objective or subjective improvement in the subject. Objective measurements of treating scarring or fibrogenesis include, without limitation, direct examination of a tissue biopsy specimen or by measured improvements in organ function, for example and without limitation, in the lung by improved spirometry; in the heart by improved left ventricular contractility or relaxation or increased exercise tolerance; in the liver by reduced stiffness as measured by elastography; and in the kidney by reduced echogenicity or characteristics on MRI scans. For skeletal muscle this might include increased exercise tolerance; for eye improved visual acuity; for peritoneum, improved gut motility and reduced intrabdominal symptoms and events; for bone marrow; improved hematopoiesis; for joints, improved function and mobility and for large vessel; improved diastolic blood flow and potentially reduction in blood pressure. In addition, functional outcomes for an organ may be evaluated: eg in the kidney by improved clearance of toxins such as measured by the glomerular filtration rate or tubular secretions of toxins such as indoxyl sulphate, or by the leakage of protein into the urine; in the liver measurements including improved blood platelets, INR, Albumin, Bilirubin levels or LFT levels. Furthermore, blood or secreted biomarkers may be sufficient measurements of fibrosis: e.g. in lung disease improvements in MMP7 and Lipocalin2; in kidney disease improvements in urine CTGF, MCP1, NGAL, KIM1 or Collagen fragments; in liver disease improvement of standard sets of blood biomarkers shown to be associated with improved fibrosis. An effective amount of a molecule or composition disclosed herein will modulate the WNT pathway. In particular embodiments, the modulation is down-regulation.

As used herein, "down-regulation" or "down-regulated" means a reduction in the activity of a signaling pathway or portion thereof. The reduction in activity lessens the physiological impact of the signaling pathway within a cell. The down-regulation can occur due to binding of a receptor, a decrease or increase in activity of an intracellular protein; elimination of an intracellular protein's activity, translation of an incomplete intracellular protein sequence; incorrect folding of an intracellular protein; reduced transcription of a gene; incomplete transcription of a gene, interference with an encoded RNA transcript, or any other activity resulting in reduced activity of the intracellular pathway, protein or gene.

A gene may be down-regulated for example by insertion of a foreign set of base pairs in a coding region, deletion of any portion of the gene, or by the presence of antisense sequences that interfere with transcription or translation of the gene. In another embodiment, down-regulation includes elimination of a gene's expression (i.e. gene knockout). In another embodiment, the disruption can occur by optionally inserting a nucleotide or polynucleotide molecule into the native gene sequence whereby the expression of the mutated gene is down-regulated (either partially or completely).

A down-regulation of a pathway may be caused by the up-regulation of relevant physiological parameters. For example, a down-regulation of the WNT pathway may be caused by up-regulation of DKK1 protein expression. Accordingly, as used herein, "up-regulation" or "up-regulated" means introducing or increasing an activity. The introduced or increased activity can be that of a protein or the intracellular result of receptor binding.

An up-regulation of a protein's activity may occur through one or more of increased presence of the protein, increased potency of the protein or increased expression of the protein. An increased presence of the protein can occur through administration of the protein or through reduced physiological degradation of the protein. Increased potency of the protein can occur through modifying naturally occurring proteins to show enhanced or extended receptor binding.

To cause an up-regulation through increased expression of a protein, the copy number of a gene or genes encoding the protein may be increased. Alternatively, a strong and/or inducible promoter may be used to direct the expression of the gene, the gene being expressed either as a transient expression vehicle or homologously or heterologously incorporated into the genome. In another embodiment, the promoter, regulatory region and/or the ribosome binding site upstream of the gene can be altered to achieve the overexpression. The expression may also be enhanced by increasing the relative half-life of the messenger or other forms of RNA.

As is understood by one of ordinary skill in the art, "down-regulation" and "up-regulation" can be measured against a relevant control condition.

Targeted Pathways

The canonical WNT signaling pathway involves the formation of a receptor complex involving a WNT ligand, a Frizzled receptor and an LRP5 or 6 co-receptor at the cell surface. This pathway triggers recruitment of a protein complex including AXIN and DSH, APC, GSK3, and the consequent release of β-catenin from this complex. The latter enters the nucleus where is regulates transcriptional activity. DKK1 binds to LRP5 and/or LRP6 and blocks the WNT interaction thereby inhibiting signaling. DKK1 is also stabilized by the KREMEN receptor. We have described that in fibrogenic cells the activation of this receptor complex also activated intracellular MAPK and JNK stress signaling pathways (which lead to a different set of gene activation from the canonical pathway), and that DKK1 blocks activation of these stress pathways.

The PDGFRβ signaling pathway is an important pathway in myofibroblast activation and migration. The ability of PDGFs to activate this receptor is dependent on the presence of LRP5 and/or LRP6, and DKK1 inhibits PDGF mediated signaling. This inhibition is dependent on the presence of the DKK1 receptor LRP5 and/or LRP6. Evidence indicates the PDGFRβ forms a complex at the cell surface with the LRP5 and/or LRP6 receptors when signaling occurs suggesting it is an essential component of the signaling complex. PDGFRs are phosphorylated and this is thought to be important in the intracellular signaling cascades. PDGFRs also activate the stress intracellular pathways including MAPK and JNK and these pathways are inhibited by that action of DKK1 on PDGFR signaling.

Many TGFβ signaling pathway responses are also blocked by administration of DKK1 in fibrogenic cells and this is at least partially dependent on the presence of LRP5 and/or LRP6. The TGFβ pathway is complex, but has both canonical and non-canonical intracellular pathways. The TAK (TGFβ-activated kinase) pathway is a major non-canonical pathway that is inhibited by the actions of DKK1. By contrast, the SMAD signaling pathway appears unaffected. TGFβR1 also interacts closely with LRP5 and/or LRP6 and this interaction is enhanced by activation of the TGFβ1 receptor by the ligand TGFβ. The studies suggest that DKK1 inhibits the TAK pathway (which includes MAPK and JNK) through binding to LRP5 and/or LRP6.

CTGF is a multi-functional protein extracellular matrix protein which binds multiple cytokines and receptors. These include the following ligands IGF1, IGF2, TGFβ, BMP4, WNT, VEGF, HSPG, and the following receptors: LRP5 and/or LRP6, Integrins including β1 integrins, αvβ3 and LRP1. The cell surface mechanism by which it activates fibrogenic cells is not entirely clear. Evidence is provided that in fibrogenic cells CTGF activates MAPK and JNK cells, and that its activating functions are dependent principally on the JNK pathway. Evidence is also provided that CTGF activates LRP5 and/or LRP6 and that DKK1 blocks CTGF mediated cell activation. Evidence is further provided that this activity is independent of activation of the TGFβR1. It is possible therefore that CTGF activation occurs through binding to LRP5 and/or LRP6 to activate fibrogenic cells and that DKK1 inhibits CTGF activity through blocking CTGF signaling via LRP5 and/or LRP6.

Targeted Receptors

LRP5 and LRP6 form a subfamily of the LDL receptor (LDLR) family, share 73% identity in their extracellular domains and are essential for WNT/β-catenin signaling. The LRP5/6 extracellular domains contain three types of subdomains: the YWTD-type β-propeller domain, an EGF-like domain and the LDLR type A (LA) domain. Based on crystal structures of the LDL receptor that contains a single propeller, the YWTD-type β-propeller domain has six YWTD repeats, which form a six-bladed β-propeller structure. The four propeller domains in LRP5/6 share a relatively low identity among them, indicating functional differences among the YWTD propellers. Each YWTD propeller domain is followed by a ~40 residue EGF-like domain that may cover the bottom face of the YWTD propeller, similar to LDLR. The small LA domains in the LRP5/6 seem to be dispensable for binding of extracellular ligands, WNT and DKK. (62).

Receptor Binding Molecules

Any molecule that binds to LRP5 and/or LRP6 receptors and down-regulates one or more of the WNT, PDGFR, TGFβ and/or CTGF signaling pathways can be used as a receptor targeting molecule as disclosed herein. Exemplary molecules include, without limitation, DKK proteins, the WNT modulator in surface ectoderm (WISE) and sclerostrin (SOST). Commercially available antibodies that bind to LRP5 and/or LRP6 receptors can also be used with embodiments disclosed herein. Non-limiting examples of LRP5 and/or LRP6 receptor antibodies are commercially available from, without limitation, Thermo Scientific, Abnova, Abcam, Santa Cruz Biotech, etc.

The protein sequences of LRP5 and LRP6 are provided in FIGS. 16 and 17 respectively (binding domains are underlined). In particular embodiments, the molecules that target LRP5 and/or LRP6 receptors include DKK proteins, including, without limitation, DKK1 (in certain embodiments comprising, consisting of or consisting essentially of SEQ ID NO. 9) or modified forms of DKK1 (in certain embodiments comprising, consisting of or consisting essentially of MGN1004 (SEQ ID NO. 5); MGN1005 (SEQ ID NO. 6); MGN1006 (SEQ ID NO. 7); and MGN1007 (SEQ ID NO. 8).

Proteins that share a % identity with the proteins explicitly disclosed herein are also within the scope of the present disclosure. The % identity is at least 85%, at least 86%, at least 87% at least 88%, at least 89%, at least 90%, at least 91%, at least 92%, at least 93%, at least 94%, at least 95%, at least 96%, at least 97%, at least 98% or at least 99%. As is known in the art, "% identity" refers to a relationship between two or more protein sequences, as determined by comparing the sequences. In the art, "identity" also means the degree of sequence relatedness between proteins as determined by the match between strings of such sequences. "Identity" (often referred to as "similarity") can be readily calculated by known methods, including (but not limited to) those described in: (67-71), each incorporated by reference herein for its teachings regarding the same. Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (73, incorporated by reference herein for its teaching regarding the same) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (72, incorporated by reference herein for its teaching regarding the same); DNASTAR (DNASTAR, Inc., Madison, Wis.); and the FASTA program incorporating the Smith-Waterman algorithm (74, incorporated by reference herein for its teaching regarding the same). Within the context of this disclosure it will be understood that where sequence analysis software is used for analysis, the results of the analysis are based on the "default values" of the program referenced. As used herein "default values" will mean any set of values or parameters which originally load with the software when first initialized.

In particular embodiments, proteins will have a higher % identity with the LRP5 and/or LRP6 receptor binding regions of SEQ ID NO. 1 or 2 than the non-binding regions of SEQ ID NO. 1 or 2. The binding regions of SEQ ID NO. 1 include SEQ ID NO. 16 and SEQ ID NO. 17. The binding regions of SEQ ID NO. 2 include SEQ ID NO. 18 and SEQ ID NO. 19. For example, a protein may have at least 95% identity with the binding regions of SEQ ID NO. 1 or 2 but only have 85% identity with the non-binding regions of SEQ ID NO. 1 or 2. In additional embodiments, a protein may have at least 98% or 99% identity with the binding regions of SEQ ID NO. 1 or 2 but only have 88% or 92% identity with the non-binding regions of SEQ ID NO. 1 or 2.

The binding regions of LRP5 and LRP6 are referred to as P1E1 (SEQ ID NO. 16 and SEQ ID NO. 18, respectively) and P3E3 (SEQ ID NO. 17 and SEQ ID NO. 19, respectively). In particular embodiments, targeting molecules can be designed to preferentially target the P1E1 or P3E3 binding regions of LRP5 and/or LRP6. In these embodiments, a higher sequence identity to the preferred binding region can be maintained as compared to the non-preferred binding region. Depending on the particular organ and condition being treated, the P1E1 or P3E3 binding region maybe preferentially targeted. In other additional embodiments, both binding regions are targeted.

Embodiments disclosed herein include derivatives of the proteins described herein. As used herein, the term "derivatives" refers to proteins having a % identity of at least 80% with the sequences disclosed herein as a result of, for example, a sequence substitution, addition, variation, modification, replacement, and/or deletion, of one (or more) amino acid residues. Any of the proteins described herein could have a derivative with an Xaa position included in any position, wherein Xaa may be a conservative substitution, deletion, addition, or stop position.

Each sequence disclosed herein may also include conservative substitutions, deletions, modifications, or additions at any position. Accordingly, in particular embodiments each amino acid position of each sequence can be an Xaa position wherein Xaa denotes a conservative substitution, a deletion, a modification, or an addition of one or more amino acids at the particular position. In particular embodiments, an Xaa position can be found at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265 and/or 266 of SEQ ID NO. 5, 6, 7, 8, or 9.

As used herein, a "conservative substitution" involves a substitution of one amino acid for another found in one of the following conservative substitutions groups: Group 1:

Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company which is incorporated by reference for its teachings regarding the same.

Prodrugs of the proteins described herein can also be used. As used herein, the term "prodrug" refers to a protein that can undergo biotransformation (e.g., either spontaneous or enzymatic) within the subject to release, or to convert (e.g., enzymatically, mechanically, electromagnetically, etc.) an active or more active form of the protein. Prodrugs can be used to overcome issues associated with stability, toxicity, lack of specificity, or limited bioavailability. Exemplary prodrugs comprise an active protein and a chemical masking group (e.g., a group that reversibly suppresses the activity of the protein). Some preferred prodrugs are variations or derivatives of proteins that have sequences that are cleavable under metabolic conditions. Exemplary prodrugs become active or more active in vivo or in vitro when they undergo a biochemical transformation (e.g., phosphorylation, hydrogenation, dehydrogenation, glycosylation, etc.). Prodrugs often offer advantages of solubility, tissue compatibility, or delayed release (See e.g., 75 and 76 both incorporated by reference for their teachings regarding the same).

Nucleotide molecules can be provided as genetic therapies to up-regulate the expression of proteins or modified forms thereof in subjects. To cause an up-regulation through increased expression of a protein, the copy number of a gene or genes encoding the protein may be increased. Alternatively, a strong and/or inducible promoter may be used to direct the expression of the gene, the gene being expressed either as a transient expression vehicle or homologously or heterologously incorporated into the genome. In another embodiment, the promoter, regulatory region and/or the ribosome binding site upstream of the gene can be altered to achieve the over-expression. The expression may also be enhanced by increasing the relative half-life of the messenger or other forms of RNA.

Standard methods may be used to administer expression constructs to a cell, tissue or organ for the purposes of modulating the expression of a target gene. Useful methods of administration include liposome-mediated transfection or transformation, transformation of cells with attenuated virus particles or bacterial cells, cell mating, transformation or transfection procedures known to those skilled in the art or described by Ausubel et al. (1992). For example, a nucleic acid molecule may be introduced as naked DNA or RNA, optionally encapsulated in a liposome, in a virus particle as attenuated virus or associated with a virus coat or a transport protein or inert carrier such as gold or as a recombinant viral vector or bacterial vector or as a genetic construct, amongst others.

In addition, hybrid viral systems may be of use. The choice of viral delivery system will depend on various parameters, such as efficiency of delivery into target tissues, transduction efficiency of the system, pathogenicity, immunological and toxicity concerns, and the like. Hybrid viral systems may also be used to combine useful properties of two or more viral systems. For example, the site-specific integration machinery of wild-type adeno-associated virus (AAV) may be coupled with the efficient internalization and nuclear targeting properties of adenovirus.

As relevant background, the Parvoviridae is a family of small single-stranded, nonenveloped DNA viruses with genomes approximately 5000 nucleotides long. Included among the family members are adenovirus (Ad) and adeno-associated virus (AAV). Adenovirus represents a group of viruses that infect the membranes of the respiratory tract, the eyes, the intestines, and the urinary tract. Adenoviruses represent the largest nonenveloped viruses, because they are the maximum size able to be transported through the endosome (i.e. envelope fusion is not necessary). The virion also has a unique "spike" or fibre associated with each penton base of the capsid that aids in attachment to the host cell. AAV is a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (63). Expression of the transgene can be exceptionally stable and in one study with AAV delivery of Factor IX, a dog model continues to express therapeutic levels of the protein 4.5 years after a single direct infusion with the virus. Because progeny virus is not produced from AAV infection in the absence of helper virus, the extent of transduction is restricted only to the initial cells that are infected with the virus. It is this feature which makes AAV a suitable gene therapy vector for the present disclosure. Furthermore, AAV appears to lack human pathogenicity and toxicity (64 and 65).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known. (See, e.g., 77 and including AAV serotypes and clades identified in, for example, 78 and 79 both of which are incorporated herein for their teachings regarding the same.

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank, including but not limited to, GenBank Accession Numbers NC002077, NC001401, NC001729, NC001863, NC001829, NC001862, NC000883, NC001701, NC001510, NC006152, NC006261, AF063497, U89790, AF043303, AF028705, AF028704, J02275, J01901, J02275, X01457, AF288061, AH009962, AY028226, AY028223, NC001358, NC001540, AF513851, AF513852, AY530579; the disclosures of which are incorporated by reference herein for teaching parvovirus and AAV nucleic acid and amino acid sequences. See also, e.g., (80-92) each incorporated by reference herein for their teachings regarding the same.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

A chosen expression construct or expression constructs can be packaged into viral particles. Any method known in the art may be used to produce infectious viral particles whose genome comprises a copy of the expression construct. The packaging cell line can be any cell line that is capable of expressing proteins, including but not limited to 293, HeLa, A549, PerC6, D17, MDCK, BHK, Cf2Th, or any other line known to or developed by those skilled in the art. One packaging cell line is described, for example, in (93) which is incorporated by reference herein for its teachings regarding the same. After production in a packaging cell line, the viral particles containing expression cassettes can be purified and quantified (titered). Purification strategies include, but are not limited to, density gradient centrifugation or column chromatographic methods.

In one embodiment, an expression cassette may be introduced into the target cells in vitro or ex vivo and then subsequently placed into a subject to affect therapy, or administered directly to a subject, organ or cell by in vivo administration. Delivery by viral infection may be one method of delivery. The vectors comprising the cassettes may be administered to a mammalian host using any convenient protocol, where a number of different such protocols are known in the art.

Proteins disclosed herein can also be recombinantly produced and formulated as therapeutic compounds. For example, the present disclosure includes recombinant constructs comprising one or more nucleic acid sequences encoding the disclosed DKK1 proteins (MGN1004, MGN1005, MGN1006, MGN1007). The constructs comprise a vector, such as, a plasmid, a cosmid, a phage, a virus, a bacterial artificial chromosome (BAC), a yeast artificial chromosome (YAC), and the like, into which a nucleic acid sequence encoding a DKK1 protein or modified DKK1 protein has been inserted, in a forward or reverse orientation. In some instances, the construct further comprises regulatory sequences, including, for example, a promoter, operably linked to the nucleic acid sequence. Large numbers of suitable vectors and promoters are known to those of skill in the art, and are commercially available.

General texts that describe molecular biological techniques useful herein, including the use of vectors, promoters and many other relevant topics, include (94). Examples of techniques sufficient to direct persons of skill through in vitro amplification methods, including the polymerase chain reaction (PCR) the ligase chain reaction (LCR), Q beta-replicase amplification and other RNA polymerase mediated techniques (e.g., NASBA), e.g., for the production of the homologous nucleic acids are found in (95-104). Improved methods of cloning in vitro amplified nucleic acids are described in (105). Improved methods of amplifying large nucleic acids by PCR are summarized in (106) and the references therein, in which PCR amplicons of up to 40 kilobases (kb) are generated. One of skill will appreciate that essentially any RNA can be converted into a double stranded DNA suitable for restriction digestion, PCR expansion and sequencing using reverse transcriptase and a polymerase.

The vector containing the appropriate DNA sequence encoding a DKK1 protein of the disclosure, as well as an appropriate promoter or control sequence, may be employed to transform an appropriate host to permit the host to express the DKK1 protein. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; plant cells; etc. The disclosure is not limited by the host cells employed.

DKK1 proteins can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any known tagging systems), hydroxylapatite chromatography, and lectin chromatography. High performance liquid chromatography (HPLC) can be employed in final purification steps. In addition to the references noted, supra, a variety of purification methods are well known in the art, including, e.g., those set forth in (107-114).

In particular embodiments, tagged and cleavable versions of the DKK1 molecules described herein can be formed using a codon-optimized human dCNA. In particular embodiments, mammalian Chinese hamster ovary (CHO) cells can be used as the protein production platform. In particular embodiments, CHO cells can be seeded in Ultra-CHO (Lonza) or CD-CHO (Life Technologies) medium containing 0.75%-1.25% v/v DMSO either in the presence or absence of 3 mM lithium acetate (LiOAc). Both DMSO and LiOAc have been shown to improve protein yields in transiently transfected CHO cells. Transfection using various ratios of DNA/PEI mixtures can be performed 3 hours after seeding and protein expression measured 7 days post-transfection.

Once protein production conditions are optimized, a fed-batch strategy for large-scale production in a Wave Bioreactor can be implemented. Briefly, transfection can be performed and the cultures fed (nutrient feeds including amino acids, vitamins, nucleosides, hydrolysates and glucose to 40 mM) every 2-4 days starting at 3 days post-transfection. This process has been shown to achieve higher cell densities and cell viability, and sustain transiently transfected CHO cultures up to 21 days. Key advantages of this protocol include the use of serum-free medium, rapidity of the procedure (relative to establishing and assessing stable cell lines), cost-effectiveness, high yields (typically 60-80 mg/L), and proper protein folding and posttranslational modifications.

With the goal of generating pure protein with no artificial sequences (affinity tags or residuals from the removal of affinity tags) the TAGZyme system (Qiagen) for DKK1 purification can be employed. In this protocol, His-tagged proteins are produced, purified with a Ni-NTA based, metal chelating strategy and the tag cleaved using the pGAPase enzyme and a subtractive IMAC protocol. If necessary, a final step of size-exclusion chromatography to obtain homogenous proteins in defined buffers can be used. Notably, Good Manufacturing Practice (GMP) quality TAGzyme enzymes are available for future use.

Nucleotide sequences are used within the context of the current disclosure as genetic therapies and as manufacturing tools for protein therapeutics. The current disclosure includes the particular nucleotide sequences disclosed herein and also includes sequences that hybridize with the disclosed sequences. In a particular embodiment, the sequences hybridize to the particularly disclosed sequences under high stringency hybridization conditions.

A nucleotide sequence "hybridizes" to another nucleotide sequence, such as a cDNA, genomic DNA, or RNA, when a single stranded form of the nucleotide sequence anneals to the other nucleotide sequence under the appropriate conditions of temperature and solution ionic strength. Hybridization and washing conditions are well known and exemplified in (115), particularly Chapter 11 and Table 11.1 therein (incorporated by reference herein for its teachings regarding the same). The conditions of temperature and ionic strength determine the "stringency" of the hybridization. Stringency conditions can be adjusted to screen for moderately similar fragments (such as homologous sequences from distantly related organisms) to highly similar fragments (such as genes that duplicate functional enzymes from closely related organisms). Post-hybridization washes determine stringency conditions. One set of hybridization conditions to demonstrate that sequences hybridize uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Stringent conditions use higher temperatures in which the washes are identical to those above except for the temperature of the final two 30 min washes in 0.2×SSC, 0.5% SDS is increased to 60° C. Highly stringent conditions use two final washes in 0.1 SSC, 0.1% SDS at 65° C. Those of ordinary skill in the art will recognize that these temperature and wash solution salt concentrations may be adjusted as necessary according to factors such as the length of the hybridizing sequences.

Administration of the molecules and compositions of the present disclosure can be performed in a variety of ways, including, but not limited to, subcutaneously, intravenously, transdermally, intraperitoneally, intramuscularly, intrapulmonary, intrathecally, vaginally, rectally, or in any other acceptable manner.

One example of a composition disclosed herein is a pharmaceutical composition in a solution designed for parenteral administration. Although in many cases pharmaceutical solution compositions are provided in liquid form, appropriate for immediate use, such parenteral compositions can also be provided in frozen or in lyophilized form. In the former case, the composition must be thawed prior to use. The latter form is often used to enhance the stability of the active molecule contained in the composition under a wider variety of storage conditions, as it is recognized by those or ordinary skill in the art that lyophilized preparations are generally more stable than their liquid counterparts. Such lyophilized preparations are reconstituted prior to use by the addition of one or more suitable pharmaceutically acceptable diluents such as, without limitation, sterile water for injection or sterile physiological saline solution.

Parenterals can be prepared for storage as lyophilized compositions or aqueous solutions by mixing, as appropriate, the composition having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives can be added to retard microbial growth, and are typically added in amounts of about 0.2%-1% (w/v). Suitable preservatives for use with the present disclosure include, without limitation, phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include, without limitation, polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the protein or helps to prevent denaturation or adherence to the container wall. Typical stabilizers can be polyhydric sugar alcohols; amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate;

low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active molecule weight.

Additional miscellaneous excipients include bulking agents or fillers (e.g., starch), chelating agents (e.g., EDTA), antioxidants (e.g., ascorbic acid, methionine, vitamin E) and cosolvents.

The active protein can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nano-particles and nanocapsules) or in macroemulsions. Such techniques are disclosed in (116) which is incorporated by reference for its teachings regarding the same.

Suitable examples of sustained-release preparations include semi-permeable matrices of solid hydrophobic polymers containing the composition, the matrices having a suitable form such as a film or microcapsules. Examples of sustained-release matrices include polyesters, hydrogels (for example, poly(2-hydroxyethyl-methacrylate) or poly(vinyl-alcohol)), polylactides, copolymers of L-glutamic acid and ethyl-L-glutamate, non-degradable ethylene-vinyl acetate, degradable lactic acid-glycolic acid copolymers such as the PROLEASE® (Alkermes, Inc., Waltham, Mass., USA; Alkermes Pharma Ireland Ltd., Althlone Co. Westmeath, Ireland) technology or LUPRON DEPOT® (Abbvie Endocrine, Inc., North Chicago, Ill., USA) (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for long periods such as up to or over 100 days, certain hydrogels release compounds for shorter time periods.

In solid dosage forms, the active molecule can be admixed with at least one inert diluent such as sucrose, lactose, or starch. Such dosage forms can also comprise, as is normal practice, additional substances, e.g., lubricating agents such as magnesium stearate.

The active molecules can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, *acacia*, gelatin, sodium alginate, polyvinylpyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Determining effective amounts of therapeutics is within the level of ordinary skill in the art. Determining an effective amount of the instant compositions can be done based on animal data using routine computational methods. For example, initially, effective amounts can be evaluated in animal models of scarring. Animal models specific to scarring can be assessed as well as animal models of diseases the reduction of scarring will ameliorate. For example, a reduction of scarring could be assessed by examining tissue biopsies or by observing increased kidney function.

Effective amounts will depend, among other factors, on the specifics of the composition chosen, on the route of administration, on the mammal being treated (e.g., human or non-human primate or other mammal), age, weight, and general condition of the subject to be treated, the severity of the scarring or potential scarring being treated, the location of the area within an organ being treated and the mode of administration. Thus, effective amounts may vary from subject to subject. An appropriate effective amount can be readily determined by one of skill in the art, and following regulatory approval of the molecules, compositions and methods disclosed herein for use in humans, will be determined by treating physicians.

Effective amounts are believed to be in the range of from about 20 to about 50 ml of saline solution containing concentrations of from about $10^{10}$ to $10^{14}$ functional molecules/ml solution. The dosage will be adjusted to balance the therapeutic benefit against any potential side effects, although significant adverse side effects are not anticipated. In another embodiment, pharmaceutically effective dose of the functional molecule is generally in the range of concentrations of from about $1 \times 10^5$ to $1 \times 10^{50}$ functional molecules, about $10^8$ to $10^2$. functional molecules, about $10^{10}$ to about $10^{16}$ functional molecules, or about $10^{11}$ to $10^{16}$ functional molecules. A human dosage may be about $1 \times 10^{13}$ functional molecules. Such concentrations may be delivered in about 0.001 ml to 100 ml, 0.05 to 50 ml, or 10 to 25 ml of a carrier solution. Other effective amounts can be readily established by one of ordinary skill in the art through routine trials establishing dose response curves.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Models of Kidney Disease. Unilateral ureteric obstruction (UUO) was performed in adult (8-12 wk) C57BL6 mice or transgenic mice (above) as previously described (1). Briefly, under anesthesia by ketamine/xylazine (100/10 mg/kg i.p), the left ureter was exposed through flank incision in the prone position. The ureter was ligated twice using 4-0 nylon surgical sutures at the level of the lower pole of kidney. In some experiments, sham operation was performed by flank incision only. Kidneys were analyzed at d1, d2, d7, d5, d7 and d10 after obstruction. In some experiments sham surgery was performed by opening skin and muscle layers but not performing surgery on the kidney. The unilateral IRI model was performed as previously described (2) using a 30-minute ischemic time at 36.8-37.3° C. core temperature. In brief, anesthetized male mice (8-12 weeks old) had both kidneys exposed through surgical flank incisions. A surgical clamp was placed across the renal arteries and veins. Kidneys were confirmed to become dusky, and replaced in the retroperitoneum for 30 min (unilateral injury). Clamps were removed and the return of perfusion to kidneys was confirmed before wound closure. Kidneys were analyzed after 10d or 14d. In some experiments purified adenovirus, either Adcontrol or AdDKK1 ($2.5 \times 10^8$ MOI) was given by tail vein on d−3, d−1 or d+4, relative to the date of surgery.

Cell Purification, culture and assays. Purification of cells from kidney. Cell purification from normal and diseased kidney as described previously (3). Briefly the kidney was decapsulated, diced, then incubated at 37° C. for 30 min with Liberase DL (0.5 mg/ml, Roche) and DNase (100 U/ml, Roche) in serum free DMEM. After centrifugation, cells were resuspended in 5 ml of PBS/1% BSA, and filtered (40 μm). Pericytes and myofibroblasts were purified from the single cell suspension isolating Coll-GFP+cells in Coll-GFP mice using FACSAria cell sorting using established methods (4), then total RNA was isolated from RLT buffer (Qiagen) (4). In normal mouse kidney Coll-GFP reports an extensive population of kidney pericytes, a smaller population of perivascular fibroblasts and podocytes. Podocytes and arterioles are separated from the remaining cells by the sieving methods. The primary cells have been characterized as described (3, 5-8).

Purification and culture of myofibroblasts Purification and culture of kidney myofibroblasts from kidney d7 after UUO was described previously (3). The primary cultured cells used in this study were between P4 and 6, cultured in DMEM/F12 with 10% FCS on gelatin 2 coated plates. For cell cycle synchronization, cells were incubated for 16 h in DMEM medium without serum.

Purification and culture of pericytes and epithelial cells. Kidney pericytes were purified from C57BL6 mice, Coll-GFP$^{Tr}$ or TCF/Lef:H2B-GFP$^{Tr}$ or Ctnnb1$^{fl/fl}$ mice, Lrp5fl/fl; Lrp6fl/fl mice or Wls$^{+/+}$ or Wls$^{fl/-}$ by MACS immunoaffinity column purification from kidney single cell preparation as above, using positive selection by anti-PDGFRβ antibodies as described (8). Purified cells were cultured in DMEM/F12 containing 10% FBS and ITS (8) on gelatin coated plates. The function and purity of these cells has been previously well characterized (8). All pericytes were studied between P3 and P6. Primary kidney epithelial cells were purified and cultured as previously described and used during P0 (8).

In vitro cell culture assays. a) Proliferation of pericytes was studied using PDGF-BB (Peprotech) at 10 ng/ml or 100 ng/ml. Fifty percent confluent pericytes seeded on coverslips in 12-well plates were cultured O/N in serum free medium, then stimulated with PDGF-BB. After 16 h they were treated with BrdU (10 μM) and analyzed at 24 h. Proliferation of myofibroblasts was performed similarly except that PDGF-BB was replaced with 3% serum. In some experiments DKK1 or vehicle was added (500 ng/ml or conditioned medium at 1:1 or 1:2 dilution). Soluble inhibitors were applied in vehicle vs vehicle alone at the following concentrations: U0157, 10 μM; SP600125, 10 μM; SB431542, 10 μM; XAV939, 2.5 μM (Tocris); IWP-2, 0.1-5 μM (Calbiochem).

Cell proliferation was assessed by FACS analysis (below) or by detecting BrdU in cell nuclei on coverslips (9, 10). b) Migration of pericytes was studied using modifications of a protocol described (11). Briefly, confluent pericytes in 6 well plates were cultured O/N in serum free medium. Cells were washed again and a scratch placed across the culture with a pipette tip. Cytokines or vehicles were added to the medium. At T0 the scratches were imaged at marked places and at timepoints after this the same areas were imaged. Migration is expressed as a percentage of the area of culture denuded of cells at T0 that has been recovered. Each timepoint is an average of 6 separate experiments, and migration assessed at 8, 16 and 24 h. Mouse TGFβ$_1$ (Peprotech) was used at 2.5 or 10 ng/ml, mouse CTGF (Peprotech) at 25 ng/ml or conditioned supernatants from pCAGGS-CTGF-IRES-GFP in 293 cells (see below). DKK1 was from R&D systems or from conditioned supernatants from pCAGGS-DKK1-IRES-GFP vs empty vector supernatants (48 h), or supernatants from AdDKK1 vs Adcontrol transduced 293T cells (48 h). CCN1 (R&D systems) was used at 100 ng/ml. WNT3a was from conditioned supernatants as previously described (12) and used at 1:2 dilution with appropriate control. In some experiments recombinant WNT3a was used at 100 ng/ml (Peprotech) c) Activation of pericytes was assessed at 48 h by Q-PCR of cDNA from cultured pericytes, and regulation of WNT genes in pericytes was quantified in cDNA 8 h after stimulation. d) Cytoskeletal reorganization was assessed in cells cultured on gelatin coated glass coverslips at 24 h after stimulation. e) Cell signaling of pericytes was assessed by application of cytokine combinations to primary cultures and lysis of cells on ice at 10 min, 1 h, and 16 h. f) Overexpression of human LRP6, LRP6-5m and LRP6-ΔC in 3T3 fibroblasts was achieved using lipofectamine with a reagent to DNA ratio of 1:4.

Positive control transfection was performed using CAGGS-TdTomato to achieve >75% transfected cells. Experiments with transfected cells were performed from 48 h-72 h. g) Genomic recombination at loxP sites in primary pericyte cultures using Cre-recombinase expressed by lentiviral transduction using Lenti-GFP (control) or Lenti-Cre, provided by the Diabetes Research Center, University of Washington. 70-80% confluent pericytes in 6-well plates were treated with 105IU of virus/104 cells and 10 μg/ml polybrene (Sigma). 24 h later medium changed and GFP expression confirmed in 100% of cells at 48 h. Experiments were performed from 48 h-72 h after transduction.

Western blot and immunoprecipitation analysis. Kidneys were homogenized in ice-cold lysis buffer (50 mM Tris/HCl, pH 7.4, 150 mM NaCl, 10% glycerol, 1% Triton X100, 2 mM EDTA, 2 mM EGTA, 40 mM β-glycerophosphate, 50 mM sodium fluoride, 10 ug/ml leupeptin, 10 ug/ml aprotinin, 1 uM pepstatin A, 1 mM phenyl-methyl-sulphonyl fluoride) and homogenized by 10 passes through an 18 G-needle fitted to a 1 ml syringe. Samples were centrifuged for 10 min at 13000 rpm and the supernatant was taken for protein determination. Cell cultures were lysed in a similar lysis buffer as described for whole kidney lysis. Cell extracts containing 20-50 μg of protein were prepared in SDS-sample buffer and subjected to SDS-PAGE. Proteins were transferred to nitrocellulose paper. After transfer, immunodetection was performed as described (13). Antibodies were diluted at 1:1000 in blocking buffer. Bands were detected by the enhanced chemiluminescence (ECL) method (Pierce) as recommended by the manufacturer and luminescence captured by FluorChem-Q (Alpha Innotech). Primary antibodies against the following antigens were used: DKK1 (R&D Systems), GFP (Molecular Probes), p-P42/44, p-JNK, p-P38, p-LRP6, p-PDGFRβ, p-FAK (Cell Signaling), p-Smad2/3 (Santa Cruz), LRP6 (Abcam), PDGFRβ (Cell signaling), β-catenin, αSMA (Sigma), CyclinD1 (Fitzgerald), WNTless (14). Immunoprecipitations were performed as described (13). In brief, cell extracts containing 100 mg of protein and 5% of fetal bovine serum in lysis buffer were incubated with either anti-PDGFRβ (Cell Signaling) or TGFβRI (Santa Cruz) antibody or isotype control at 1:1000 dilution (4° C. O/N). Thereafter, 25 μl of ProteinA-Sepharose 4B CL slurry (Invitrogen) was added and incubated (2 h RT). After precipitation, sepharose was washed with 0.2M Tris (pH 8.5) then heated (5 min, 95° C.) in Laemmli buffer prior to SDS-PAGE and western blotting as described above. In some experiments membrane-bound β-catenin was separated from cytosolic and nuclear β-catenin by ConA-Sepharose 4B (GE Healthcare) precipitation of cadherin-bound β-catenin in whole cell lysates prior to immunodetection of β-catenin using methods as described (12). Density analysis of immunodetected protein bands was performed as described (15).

Real Time-PCR. Total RNA was extracted using Trizol. Purity was determined by A260 to A280. cDNA was synthesized using oligo(dT) and random primers (iScript, Biorad). Quantitative PCR was performed using ABI machine, iTaq SYBR Green supermix with ROX (Biorad) using methods described in instruction. The specific primer pairs used in Q-PCR were tested for specificity and are listed in Table S1.

TABLE S1

Primers for Q-PCR

| Gene | Forward primer | Reverse primers |
| --- | --- | --- |
| Acta2 | CTGACAGAGGCACCACTGAA (SEQ ID NO. 20) | CATCTCCAGAGTCCAGCACA (SEQ ID NO. 21) |
| Axin2 | TAGGCGGAATGAAGATGGAC (SEQ ID NO. 22) | CTGGTCACCCAACAAGGAGT (SEQ ID NO. 23) |
| Col1a1 | GAGCGGAGAGTACTGGATCG (SEQ ID NO. 24) | GTTCGGGCTGATGTACCAGT (SEQ ID NO. 25) |
| Cspg4 | AGCTGATGCTGGAGGTGTCT (SEQ ID NO. 26) | GAAGATGATGCGAGGTGGAT (SEQ ID NO. 27) |
| Ctgf | AGCAGCTGGGAGAACTGTGT (SEQ ID NO. 28) | GCTGCTTTGGAAGGACTCAC (SEQ ID NO. 29) |
| Dkk1 | GAGGGGAAATTGAGGAAAGC (SEQ ID NO. 30) | ACGGAGCCTTCTTGTCCTTT (SEQ ID NO. 31) |
| Dkk2 | CAGGGGGAAGTCTGTACCAA (SEQ ID NO. 32) | GGTGGCATCTTTCCACACTT (SEQ ID NO. 33) |
| Dkk3 | ACCAGAGTGGACAGGTGGTC (SEQ ID NO. 34) | GGCGGAGACTCTTCATCAAT (SEQ ID NO. 35) |
| Fgf2 | CACCAACTGCACCAATGAAC (SEQ ID NO. 36) | GGCTGGGTGAGATCCAAGTA (SEQ ID NO. 37) |
| Fgf23 | TGCTAGGGACCTGCCTTAGA (SEQ ID NO. 38) | GTACAGGTGGGTCAGGCTTC (SEQ ID NO. 39) |
| Kim1 | AGGAAGACCCACGGCTATTT (SEQ ID NO. 40) | TGTCACAGTGCCATTCCAGT (SEQ ID NO. 41) |
| Lngfr | CAAGGAGACATGTTCCACA (SEQ ID NO. 42) | ACCACGTCAGAGAACGTAAC (SEQ ID NO. 43) |
| Pdgfrb | CACCTTCTCCAGTGTGCTGA (SEQ ID NO. 44) | GGAGTCCATAGGGAGGAAGC (SEQ ID NO. 45) |
| sFrp4 | CACCACAGCACTCAGGAGAA (SEQ ID NO. 46) | ACAGACTTGCAGGGCTTGAT (SEQ ID NO. 47) |
| sFlt1 | ATGCGCTGCAGAGCCAGGAAC (SEQ ID NO. 48) | GGTACAATCATTCCTCCTGC (SEQ ID NO. 49) |
| Tgfb1 | GAAGGACCTGGGTTGGAAGTGG (SEQ ID NO. 50) | CGTAGTAGACGATGGGCAGTGG (SEQ ID NO. 51) |
| Wisp1 | CCCCTACAAGTCCAAGACCA (SEQ ID NO. 52) | CGTTAGGATTCCTGCAGCTC (SEQ ID NO. 53) |

Tissue preparation and histology. Mouse tissues were prepared and stained as previously described (2). Briefly, tissues for cryosectioning (7 mm) were fixed in PLP solution for 2 h, then washed in 18% sucrose solution overnight prior to cryo-preservation. Tissues for paraffin sectioning (3 mm) were fixed 12 h, in 10% formalin solution prior to 70% ethanol solution. For fluorescence detection or antigens in cryosections, primary antibodies or lectins against the following proteins or carbohydrates were used for labeling: αSMA-Cy3 (1:200, clone 1A4, Sigma), F4/80, CD31, (1:300, EBioscience), ECadherin (1:200, R&D), Aquaporin 2 (1:200, Abcam), Ki67 (1:200, Vector), PDGFRβ (1:200, eBioscience), Lotus lectin-fluorescein, DBA-rhodamine (VectorLabs). Fluorescent conjugated affinity purified secondary antibody labeling (1:400-1:800, Jackson lmmunoresearch) was performed where indicated. Sections were co-labeled with DAPI, and mounted with Vectashield. Image capture and processing were carried out as previously described using confocal microscopy (2). Quantification of specific cells in tissue sections was carried out as previously described (2). In brief, sections were co-labeled with DAPI, cells were identified by nuclear co-localization; αSMA+ were identified by greater than 75% of the cell area immediately surrounding nuclei (detected by DAPI) staining positive with Cy3 fluorescence indicative of the antigen expression; Ki-67+ cells were identified by positive nuclear staining for Cy3 fluorescence. Specific cells were counted in 10 cortical interstitial fields randomly selected at 400× magnification per mouse. Vessel fluorescence was analyzed in images at 400× magnification captured from CD31-stained sections of 10 different fields from 6 different animals. Based on fluorescence intensities ranging from 0 to 255, peritubular capillaries were distinguished from background by empirically determining threshold values that marked only blood vessels in specimens from control kidney in sham-operated mice. The threshold was constant for all measurement (8). Interstitial fibrosis was quantified in picrosirius red-stained paraffin sections. The morphometry of CD31+ peritubular capillary and picrosirius red+ collagen was quantified using Photoshop (Adobe) as described previously (8).

Flow cytometric analysis. Cell proliferation, cell cycle kinetics were measured by BrdU and Propidium Iodide (PI) incorporation which were subjected to Becton Dickinson flow cytometer for analysis or counted by fluorescence microscopy. In Brief, myofibroblasts were incubated with 10 mM Brdu for 30 min at 37° C. Afterwards cells were trypsinized, harvested, and single cells (2×10$^5$) resuspended in PBS, then fixed in 70% Ethanol at −20° C. (30 min on ice) with vortexing. After centrifugation (1000 rpm 5 min), cells were further incubated with 2N HCl/0.5% Triton X-100 (30 min RT), neutralized in 0.1M Na$_2$B$_4$O$_7$, washed with 0.5% Tween 20/1% BSA/PBS 2×. then labeled with FITC-coupled anti-BrdU antibodies (eBioscience) (1:100, 30 min). After washing (X2), cells were resuspended in 300 ml PBS containing 5 µg/ml PI and analyzed for DNA content with Becton Dickinson flow cytometer. Results were analyzed by FlowJo software.

Generation of Vectors, Cloning of DKK1, production of recombinant proteins and receptors in vitro and in vivo.

DKK1 was cloned from cDNA of whole C57BL6 mouse kidney from using the specific primers into pGEM®-T Easy Vector (Promega, Madison, Wis., USA), subcloned and expressed in PMX-puro. After sequencing, DKK1 was fused to GFP in EGFP-N1. Both DKK1 and DKK1 fusion proteins were subcloned into pCAGGS-IRES-GFP neo, pENTR-IRES-GFP generated from pCAG (16) and pENTR 2B (Invitrogen). pENTR-IRES-GFP or pENTR-DKK1-IRES-GFP underwent site-specific Gateway recombination with pAd/CMV/V5-DESTTm vector (Invitrogen). Linearized vector was then transfected into 293A cells (Invitrogen) which were used to generate and expand the viruses, Adcontrol or AdDKK1, in serum free growth medium. Viruses were purified freeze-thaw of cell, followed by filtration, followed by CsCl gradient ultracentrifugation as described (17), and MOI was calculated using an established assay (17). Mouse CTGF ORF was synthesized and expressed in pCAGGS-CTGF-IRES-GFP, transfected into 293 cells and serum free medium supernatants collected after 48 h. Control supernatants were from 293 cells transfected with pCAGGS-IRES-GFP. Control or WNT3a conditioned medium were from L and L-WNT3A cells (ATCC) respectively, as described (12). Secreted protein production was confirmed by precipitating proteins in conditioned supernatants and after denaturing in Laemmli buffer testing specificity by SDS-PAGE and Western blotting. Wild type human LRP6 or LRP6 lacking the cytoplasmic domain (DC), or LRP6 with tyrosine to methionine mutations at the five tyrosine sites (5 m) on the intracellular domain were expressed in pCS2+ vector as previously characterized and described (18) and were purchased from Addgene.

Mouse Models. Col1a1-GFP$^{Tr}$ (Coll-GFP) mice were generated, maintained and genotyping was performed as previously described (33). Axin2$^{+/lacz}$ mice were generated as previously and genotyped as described (16). TCF/Lef:H2B-GFP$^{Tr}$ mice were generated at the Sloan-Kettering Institute, New York as previously described (34) and genotyping was performed with the following primer pairs: 5'-AAGT-TCATCTGCACCACCG-3' (SEQ ID NO. 54), 5'-TGCTCA-GGTAGTGGTTGTCG-3' (SEQ ID NO. 55). Ctnn1$^{fl/fl}$ mice were from Jackson Labs (35). All studies were carried out under approved IACUC protocols held at University of Washington.

Statistical analysis. Error bars are SE of mean. Statistical analyses were carried out using Graph Pad Prizm (GraphPad Software). The statistical significance was evaluated by one-way ANOVA.

Results and Discussion

The WNT/β-catenin pathway is upregulated in myofibroblasts in kidney disease. To explore the extent of activation of canonical WNT pathway in cells of the normal kidney two distinct lines of mice that are transgenic for reporters of WNT/β-catenin signaling were studied. Axin2$^{+/lacz}$ generates β-gal in cells expressing the endogenous WNT/β-catenin target gene, Axin2. (FIG. 10A) (33). TCF/LEF-H2B-GFP$^{Tr}$, is a novel and recently validated transgenic line of mice reporting β-catenin activity by nuclear GFP expression. It exhibits enhanced sensitivity and specificity over previous reporters of β-catenin nuclear activity (FIG. 10A) (34). In normal kidney of Axin2$^{+/lacz}$ mice there is extensive WNT/β-catenin signaling in the papilla, and more restricted responses in the normal medulla and kidney cortex (FIG. 10B).

Figure 10:
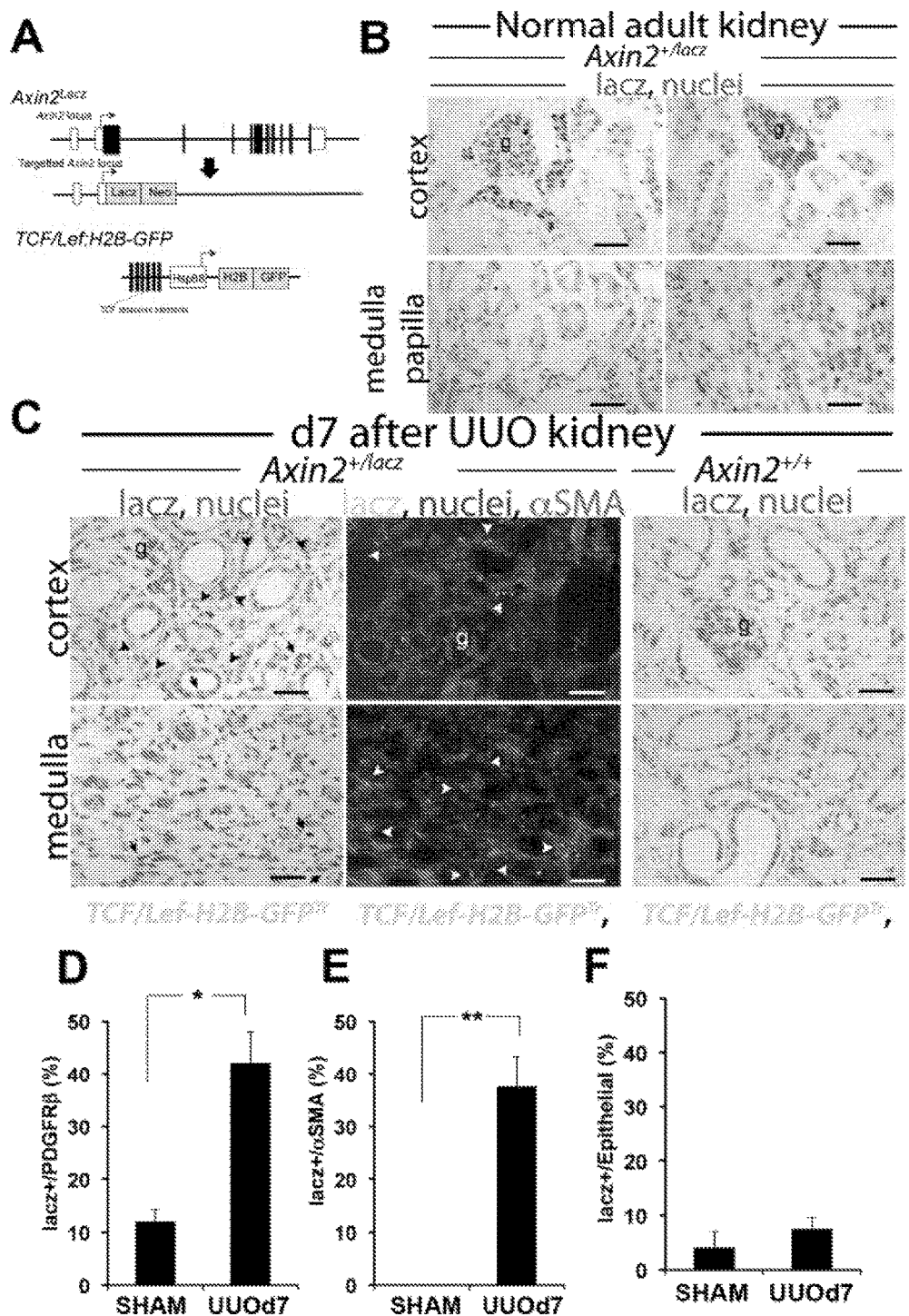
FIG. 10. WNT/β-catenin signaling is activated during kidney injury in the pericyte/myofibroblast cell compartment. (A) Schema showing the Axin2$^{LacZ}$ allele and the TCF/Lef:H2B-GFP transgene, which report WNT/β-catenin signaling. (B-C) WNT responses identified by fluorescence in cells of normal kidney (B) and cells during kidney injury induced by UUO (C) in Axin2+$^{/lacz}$ reporter mice is seen predominantly in myofibroblasts (arrowheads) and epithelial cells (arrows) (g=glomerulus), but no stain is seen in Axin2$^{+/+}$ kidneys. Note signal in normal kidney distal tubule, occasional podocytes and marked signal in the papilla. (D-F) Graphs showing proportion of cells with positive signal for Axin2 activity. (G) WNT/β-catenin responses identified by nuclear GFP in confocal images of normal kidneys or after UUO from TCF/Lef:H2B-GFP$^{Tr}$ reporter mice, highlighting PDGFRβ+ cells which are predominantly pericytes in normal kidney and are myofibroblasts in diseased kidney. (H) Canonical WNT responses seen (arrowheads) in myofibroblasts (αSMA+). Active signal in pericytes and myofibroblasts (arrowheads). Note that many epithelial cells have signal (J-M) Timecourse of signaling activity in different cell populations in response to UUO injury. Lotus lectin (LTL) detected proximal epithelium, anti-aquaporin2 (AQP2) detects distal epithelium and loop of Henle. ($*P<0.05$, $**P<0.01$. Experiments are from n=4/group).

Among the cells expressing lacz were podocytes, vascular smooth muscle of arterioles and some pericytes (FIG. 10B-F) In response to injury, initiated by obstructing urine flow from the kidney (unilateral ureteral obstruction [UUO] model), there was marked increase in lacz staining in the scar forming cells known as myofibroblasts that derive from pericytes (FIG. 10B-D). Although collecting duct and cells of the loop of Henle showed Axin2-lacz staining, there was little lacz detected in distal and proximal tubule in either normal or diseased kidneys.

Figure 2:
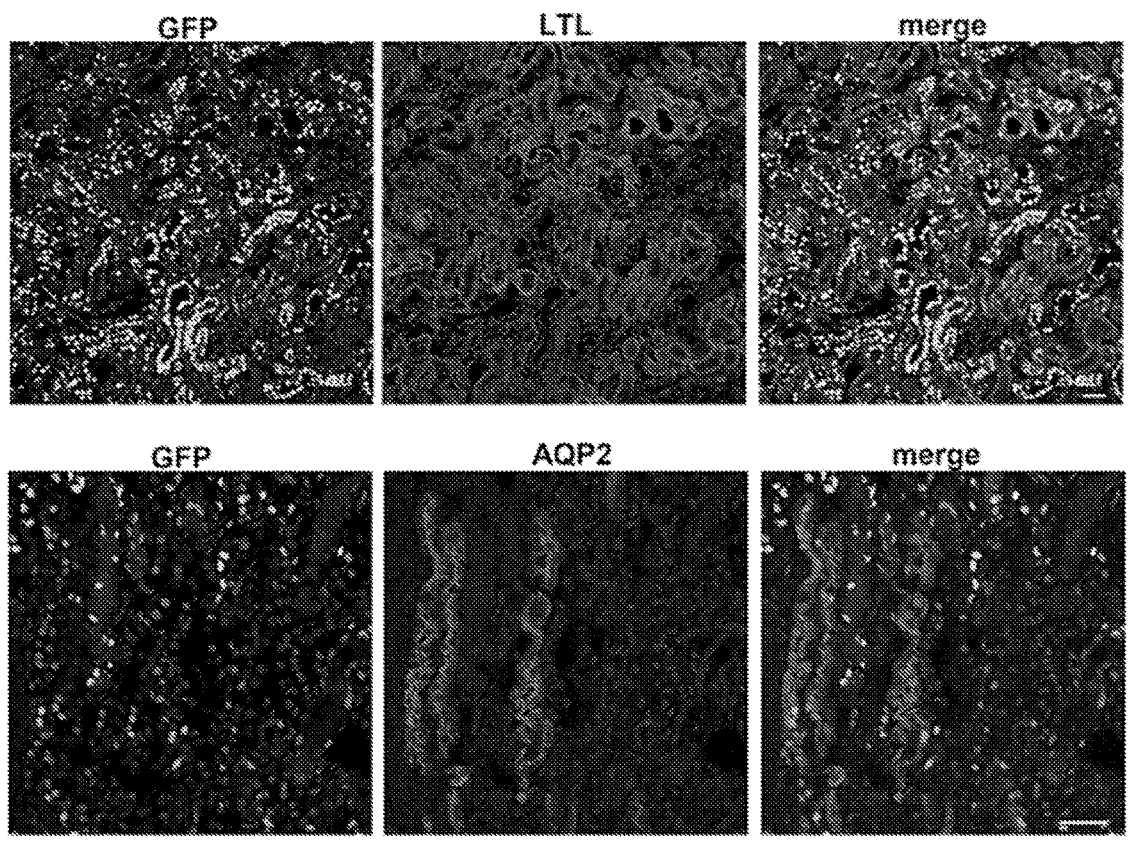
FIG. 2. Split panel fluorescence confocal images showing the co-localization of nuclear GFP in collecting duct cells (AQP2+) and proximal tubules cells (LTL+) in the unilateral ureteric obstruction (UUO) model of kidney injury (Bar=50 μm).

To visualize this WNT response in greater detail WNT reporter activity in TCF/LEF-H2B-GFPTr mice was localized. In normal kidney, β-catenin responses were more extensive than previously appreciated. In normal kidney, proximal and distal epithelium exhibits little endogenous WNT/β-catenin reporter activity (31). In contrast there was evidence in TCF/LEF-H2B-GFP$^{Tr}$ mice of WNT reporter activity in many of these cells (FIG. 10G-L, FIG. 2). However, similarly to the Axin2$^{+/lacz}$ reporter, a minority of pericytes showed active signaling in normal kidney. Following kidney injury, WNT/β-catenin reporter activity increased in epithelial cell compartments, but there was a much greater increase in the pericyte/myofibroblast population of cells (FIG. 10G, H, J, K, FIG. 2).

Figure 3:
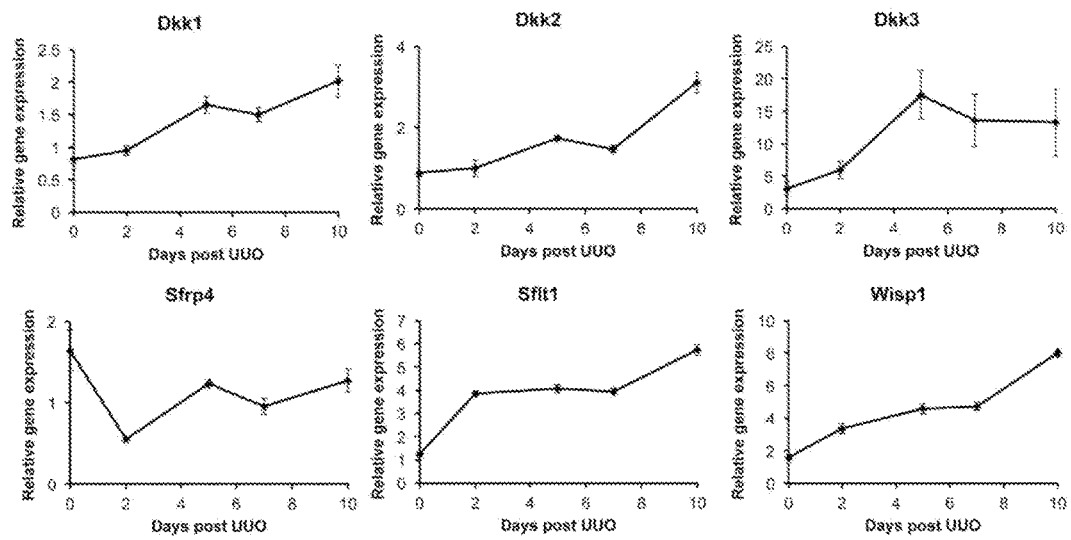
FIG. 3. Characterization of WNT signaling activation in different cell types during kidney injury. (A) Q-PCR data showing changes in expression of pro-fibrotic and cell activation gene transcripts in purified non-glomerular cells from Coll-GFP reporter mice from normal kidney and timepoints after UUO kidney injury. (B) DNA gel showing 30 cycle PCR for WNT ligands and receptors using cDNA from Coll-GFP cells purified from normal kidney and d4 after UUO kidney injury. Upregulated gene transcripts are indicated (arrowheads). (C) Q-PCR data showing changes in expression of regulators of the canonical WNT pathway and downstream reporters of non-canonical and canonical WNT responses. (*P<0.05, **P<0.01. Experiments are from n=4/group). (D) Q-PCR time course showing normalized levels of PDGFR6 and Cspg4 (NG2) transcripts in pericytes/myofibroblasts purified from normal kidneys and in days after UUO surgery. (E) Western blot showing total cell (including membrane associated) β-catenin levels in myofibroblasts in response to cytokines at 1 h and 16 h.

Kidney myofibroblasts upregulate WNT pathway genes and WNT reporter activity. To explore WNT pathway activation in kidney myofibroblasts further, non-activated pericytes (normal kidney), activated pericytes, (from d2 after UUO) and myofibroblasts transitioned from pericytes (from d5, d7 and d10 after UUO) were purified by flow cytometric sorting of single cell digests from kidneys of the Col1-GFP$^{Tr}$ reporter mouse, which specifically expresses GFP in these cells (35). Purified cells showed marked upregulation of pericyte genes including P75 NGFR (Ngfr) (FIG. 3A), and at baseline expressed detectable levels of NG2 (Cspg4) and PDGFRβ (Pdgfrb) that were modestly upregulated over time post-injury (FIG. 3D). Prototypical profibrotic genes expressed in normal kidney and upregulated over time post-injury in our disease model, including Collet Tgfb1, Ctgf and Fgf2 were found. Upregulation of the phosphatonin, Fgf23, which has been implicated in the pathogenesis of cardiovascular disease (36) (FIG. 3A) was also observed. WNT ligands, including WNT2, 3, 7b, 8a, 8b, 10a were upregulated. WNT11 was down-regulated. Pericytes also express cell surface receptors (Fzd) and co-receptors (Lrp) for WNT responsiveness (FIG. 3B). As the course of kidney disease progressed there was a modest upregulation of DKK family of mRNAs that are known to inhibit canonical WNT signaling via direct binding to the LRP5, and LRP6 co-receptors (FIG. 3C). Other WNT downstream target genes including sFlt1, and WISP1, which play important roles in non-canonical, and canonical WNT signaling pathways respectively, were also upregulated. This trend is consistent with activated WNT/β-catenin and also non-canonical WNT pathways (FIG. 3C).

Figure 11:
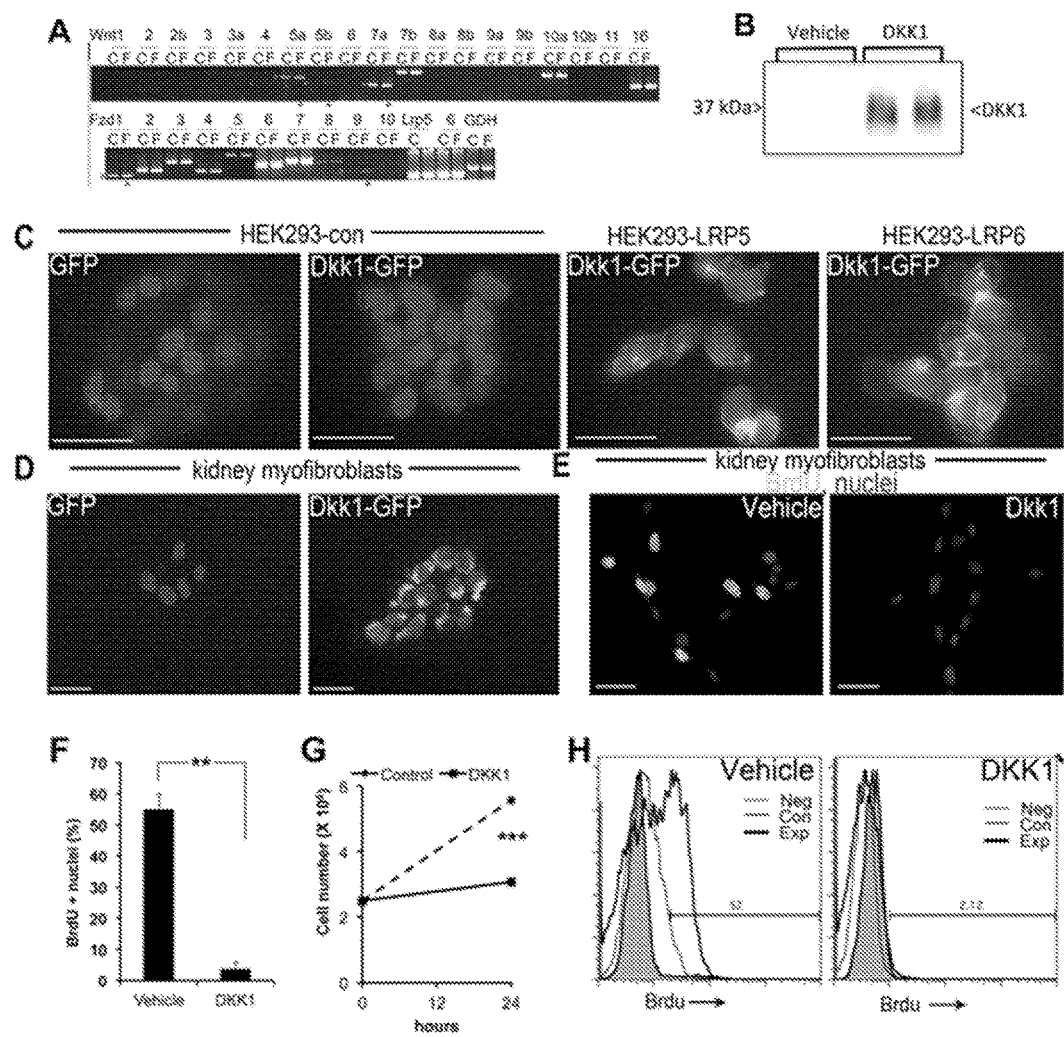
FIG. 11. DKK1 binds to myofibroblasts and blocks proliferation by G1/S cell-cycle arrest in vitro. (A) RT-PCR and Q-PCR results showing expression of WNT ligands, receptors in kidney myofibroblasts established from d7 UUO in control conditions (C) or in response to FCS (F). (B) Western blot of recombinant DKK1 protein synthesized in HEK293 cells transduced with control or DKK1-generating retroviral vectors. (C) Transfer of medium (4° C.) containing soluble DKK1-GFP fusion protein or control medium (from cell synthesizing intracellular GFP) to HEK293 cells results in weak cell surface binding of the green fusion protein, but this is markedly enhanced by transfer to HEK293 cells transgenically expressing the WNT co-receptors LRP5 or LRP6. (D) By contrast DKK1-GFP readily binds to primary kidney myofibroblasts. (E-F) Images and graph showing BrdU nuclear incorporation in quiescent myofibroblasts stimulated for 3 h with medium containing 3% FCS in the presence of 30% DKK1 medium or control. (G) Coulter-counted kidney quiescent myofibroblasts stimulated for 24 h with 3% FCS in the presence of 30% DKK1 medium or control. (H and J) Flow cytometric plots and graph showing BrdU uptake in myofibroblasts stimulated for 3 h with 3% FCS in the presence of 30% DKK1 medium or control. (K-L) Propidium iodide DNA content plots and graph showing quiescent myofibroblasts stimulated for 24 h with 3% FCS in the presence of 30% DKK1 medium or control. (M) The effect of DKK1 on cytoplasmic and nuclear β-catenin protein. Serum increases β-catenin, an effect, not modulated by DKK1 at 1 h but at later timepoints DKK1 markedly reduces β-catenin levels. (N) Q-PCR data showing myofibroblast expression of Acta2 after treatment with FCS or FCS+DKK1. ($*P<0.05$, $**P<0.01$. Experiments are from n=4/group).
Figure 11:
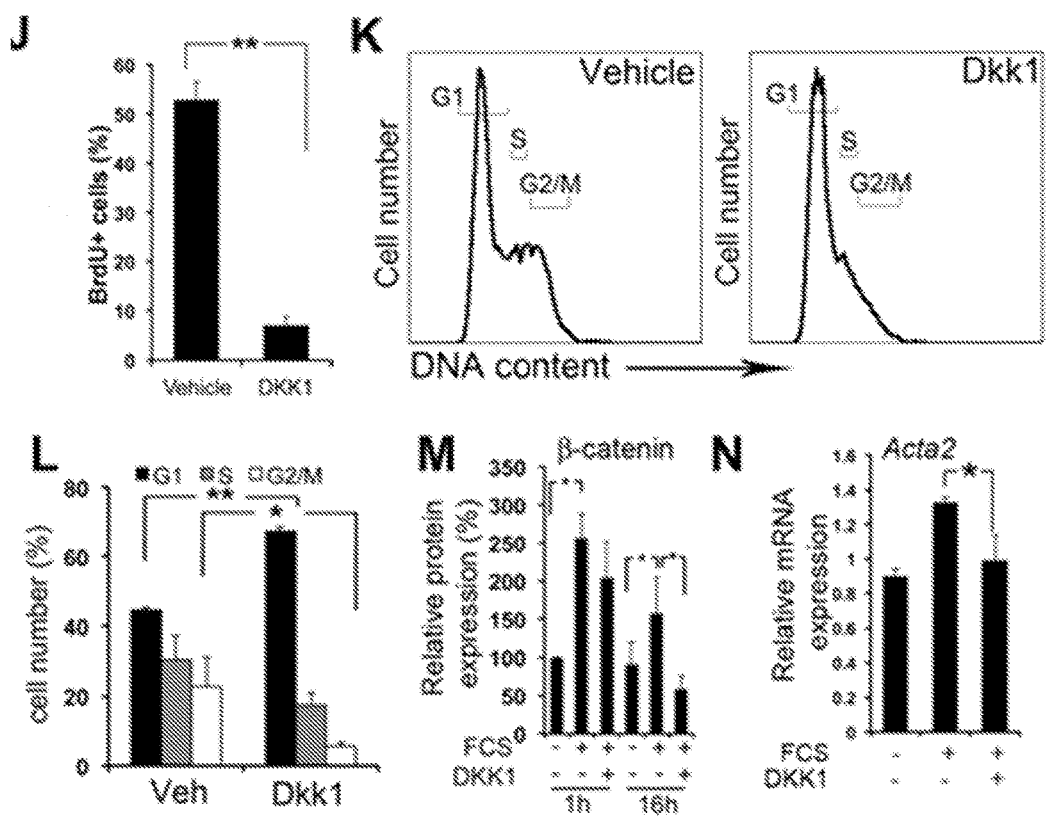

DKK1 triggers G1 cell cycle arrest and down-regulates activation in myofibroblasts. To test the function of WNT/β-catenin pathway activation in myofibroblasts primary myofibroblast cultures from Coll-GFP$^{Tr}$ mice that had kidney fibrosis (35) were generated. Myofibroblasts also expressed WNT ligands and receptors (FIG. 11A). DKK1 has been reported to inhibit the WNT/β-catenin pathway by binding to LRP5 or LRP6. DKK1 was cloned and expressed soluble DKK1 protein (FIG. 11B) in HEK293 cells. A stable cell line expressing soluble DKK1-GFP fusion protein was also generated. Soluble DKK1-GFP binding to unlabeled cell lines was markedly enhanced by overexpression with LRP5 or LRP6 (FIG. 11C) and DKK1-GFP readily bound to the surface of cultured myofibroblasts without the requirement for receptor over-expression (FIG. 11D), indicating high receptor density for DKK1 on myofibroblasts. DKK1 protein specifically blocked entry of myofibroblasts into cell cycle induced by serum (FIG. 11E-F, H-J), resulting in an inability to proliferate (FIG. 11G). Proliferation was specifically blocked at G1 cell-cycle checkpoint (FIG. 11K-L) without apoptosis (hypodiploid cells) (FIG. 11K).

To better understand the mechanisms, the effect of DKK1 on steady state level of β-catenin protein was tested. Cytosolic and nuclear β-catenin increased 1 h after serum activation, which was not decreased by DKK1 (FIG. 11M, FIG. 3E). After 16 h of serum activation, β-catenin was still elevated, but now DKK1 markedly inhibited this increase. These results confirm DKK1 can inhibit WNT/β-catenin signaling and suggest early DKK1 responses may occur independent of regulation of β-catenin protein (FIG. 11M, FIG. 3E). Transcripts for αSMA (Acta2), a marker of myofibroblast activation were increased by serum at 24 h and DKK1 significantly reduced this activation (FIG. 11N) suggesting DKK1 may also regulate activation.

Systemic delivery of DKK1 inhibits myofibroblast expansion and fibrosis. Next whether DKK1 inhibited pericytes and myofibroblasts in vivo was tested. DKK1 was delivered systemically using an adenoviral delivery system that generates high-level expression of circulating DKK1 protein (FIG. 12A). The capacity of circulating DKK1 on both development and progression of kidney fibrosis using three different experimental designs was tested (FIG. 12B). In preventative studies using the UUO model of kidney fibrosis, circulating DKK1 profoundly inhibited pericyte expansion, proliferation and transition to myofibroblasts (FIG. 12C-J), resulting in reduced fibrosis (FIG. 4). This inhibition on d4 after UUO was associated with a marked reduction in inflammation (FIG. 12K) and epithelial injury, as assessed by chronic proliferation and expression of the epithelial injury marker KIM-1 (FIG. 4). Moreover, expression of the WNT/β-catenin reporters in the kidney myofibroblasts was reduced, particularly at the earlier timepoints (FIG. 12L). These studies were extended to d10 after UUO injury and there was a substantial reduction in organ fibrosis and collagen transcripts (FIG. 12M-P).

To study this effect in more detail a reversal study whereby DKK1 was delivered after disease onset and fibrosis extent was assessed d10 after UUO was performed (FIG. 12Q-R). DKK1 again inhibited myofibroblast accumulation, proliferation, deposition of interstitial fibrosis and limited rarefaction of the capillaries. Furthermore, as in the preventative studies, DKK1 inhibited inflammation and epithelial injury (FIG. 4). Because recent evidence indicates myofibroblasts in kidney arise from pericyte precursors which detach from peritubular capillaries in response to injury before the become myofibroblasts (22), the effect of DKK1 on pericyte precursor detachment, spreading and migration in Coll-GFP$^{Tr}$ reporter mice was examined. DKK1 inhibited pericyte detachment from capillaries at early timepoints in this model (FIG. 12S-T).

Figure 5:
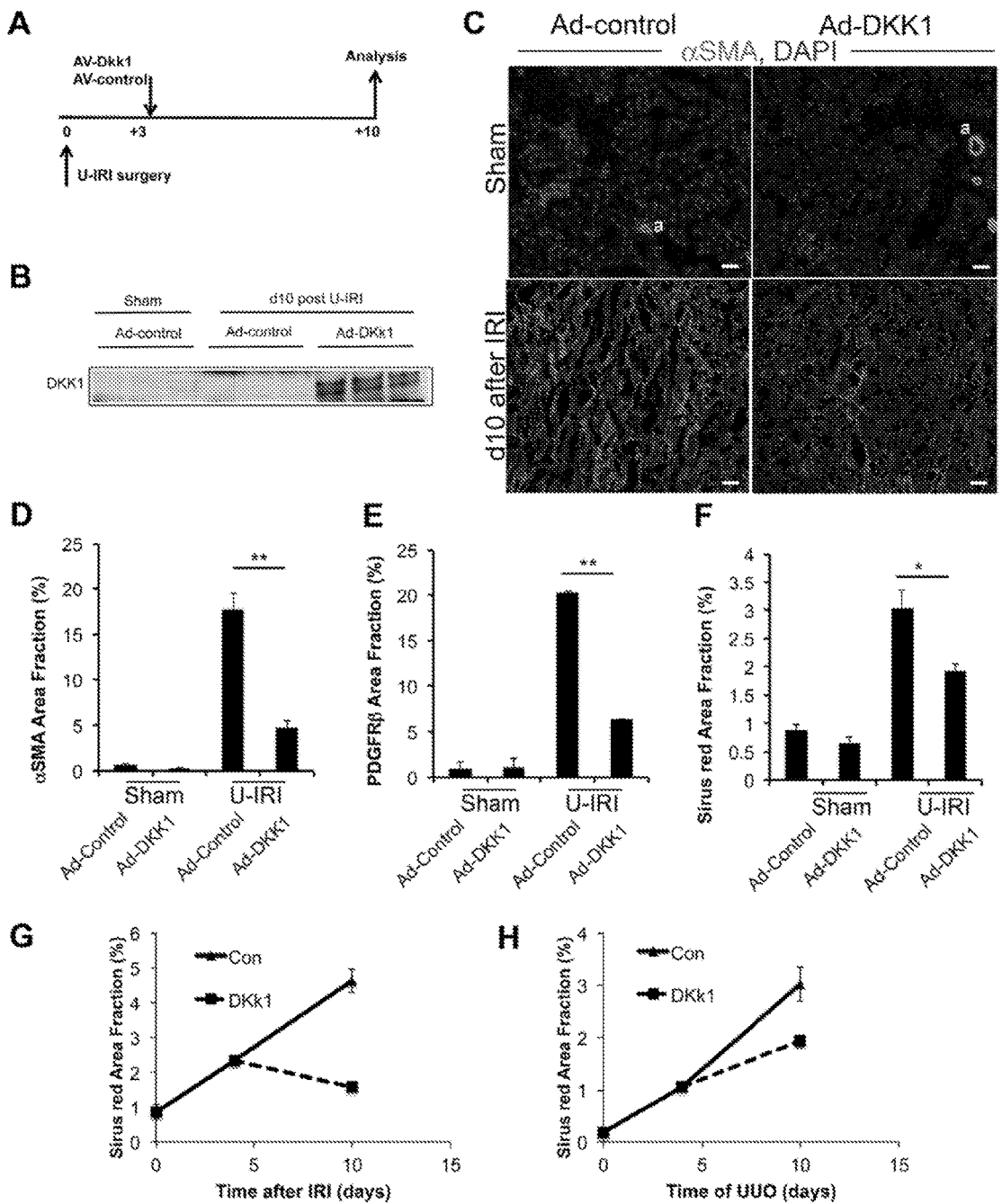
FIG. 5. DKK1 inhibits fibrogenesis following unilateral kidney ischemia reperfusion injury. (A) Schema showing experimental approach. (B) Western blot of 2μl of plasma from mice d10 after U-IRI or after sham surgery in mice that received AdDKK1 or Adcontrol. (C) Immunofluorescence images of outer medulla, and (D) morphometric quantification of kidneys d10 after IRI showing immune-reactivity for the myofibroblast marker αSMA. (E) Morphometric quantification of PDGFRβ immunoreactivity and (F) morphometric quantification of sirius red stained fibrosis. ($*P<0.05$, $**P<0.01$, Experiments are from n=6/group). (G) Time course accumulation of sirius red stained fibrotic matrix in the kidney after U-IRI in the presence of Adcontrol or AdDKK1 given on d3. Note that accumulated matrix regresses in kidneys exposed to circulating DKK1 but not in controls. (H) Time course accumulation of sirius red stained fibrotic matrix in the kidney after UUO in the presence of Adcontrol or AdDKK1 given on d3. Note that accumulated matrix increases further in DKK1 treated mice but this is markedly reduced compared to control-treated mice.

Whether DKK1 could inhibit disease in a second model of inflammation and fibrosis, acute ischemia reperfusion injury (IRI) in a single kidney, a recognized model of CKD following acute kidney injury (31) was tested. A reversal study in this model and characterized the extent of scarring in the kidney 10 d after the initial IRI. DKK1, delivered in the circulation, inhibited myofibroblast accumulation, inflammation and interstitial fibrosis (FIG. 5) and reduced epithelial injury (FIG. 4) was performed. Importantly in this model, delivery of DKK1 was sufficient to reverse existent fibrosis (FIG. 5G-H).

Figure 13:
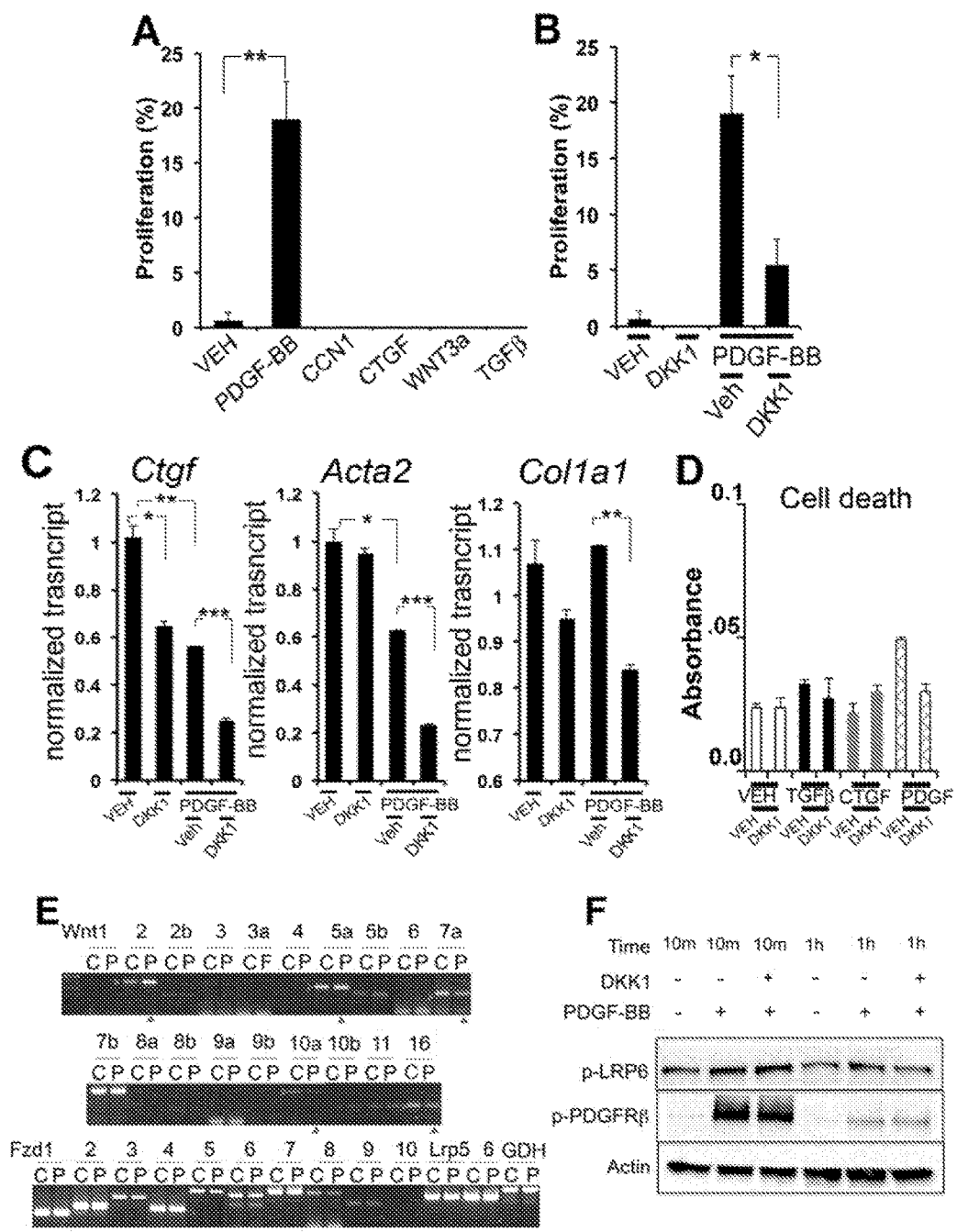
FIG. 13. DKK1 inhibits PDGF-BB mediated proliferation of pericytes in vitro by a noncanonical, LRP6 dependent, P42/44 MAPK dependent mechanism. (A) Graph of BrdU incorporation into quiescent kidney pericytes 6 h after stimulation with cytokines. (B) The effect of DKK1 on PDGF-BB stimulated proliferation. (C) Q-PCR of genes associated with cell activation in pericytes, 48 h after stimulation. (D) Quantification of cell viability in pericytes stimulated with cytokines and DKK1 for 24 h. (E) RT-PCR results showing the effect of PDGF-BB on WNT ligands and receptors in pericytes 12 h after stimulation. (C, control; P, PDGF; arrowheads=regulated genes). (F) Western blot time course showing phospho-PDGFRβ and phospho-LRP6 levels in pericytes. DKK1 does not affect p-LRP6 at early timepoints, but inhibits at later timepoints. (G) Fluorescence images and data quantifying nuclear GFP+(green) in TCF/Lef:H2B-GFP$^{Tr}$ canonical WNT reporter pericytes, 16 h after PDGF-BB or PDGF-BB+DKK1. (H) Western blot timecourse of phosphorylated forms of P42/P44, JNK and P38, PDGFRβ and total CyclinD1 in pericytes activated by PDGF-BB or PDGF-BB+DKK1. (J) Graph showing the effect DKK1 or canonical WNT inhibitor XAV939, P42/P44 inhibitor U0126 or JNK inhibitor SP600125 on PDGF-BB stimulated BrdU incorporation into quiescent pericytes. (K) Graph showing the effect of PDGF-BB on proliferation of Ctnnb1$^{fl/fl}$ pericytes that underwent in vitro recombination by expressing Cre recombinase vs Ctnnb1$^{fl/fl}$ pericytes that expressed control protein GFP. (L) Western blot of pericyte proteins immunoprecipitated by anti-PDGFRβ antibodies or control antibodies, detecting p-LRP6 or PDGFRβ (M) Graph showing the effect of expression of LRP6 (wild type), or dominant negative forms of LRP6, 5 m or ΔC on 3T3 fibroblast proliferation in response to PDGFBB and DKK1. (*P<0.05, P<0.01, *P<0.01. Experiments are from n=4-7/group. All blots representative of 3 expts, Bar=25 µm).
Figure 13:
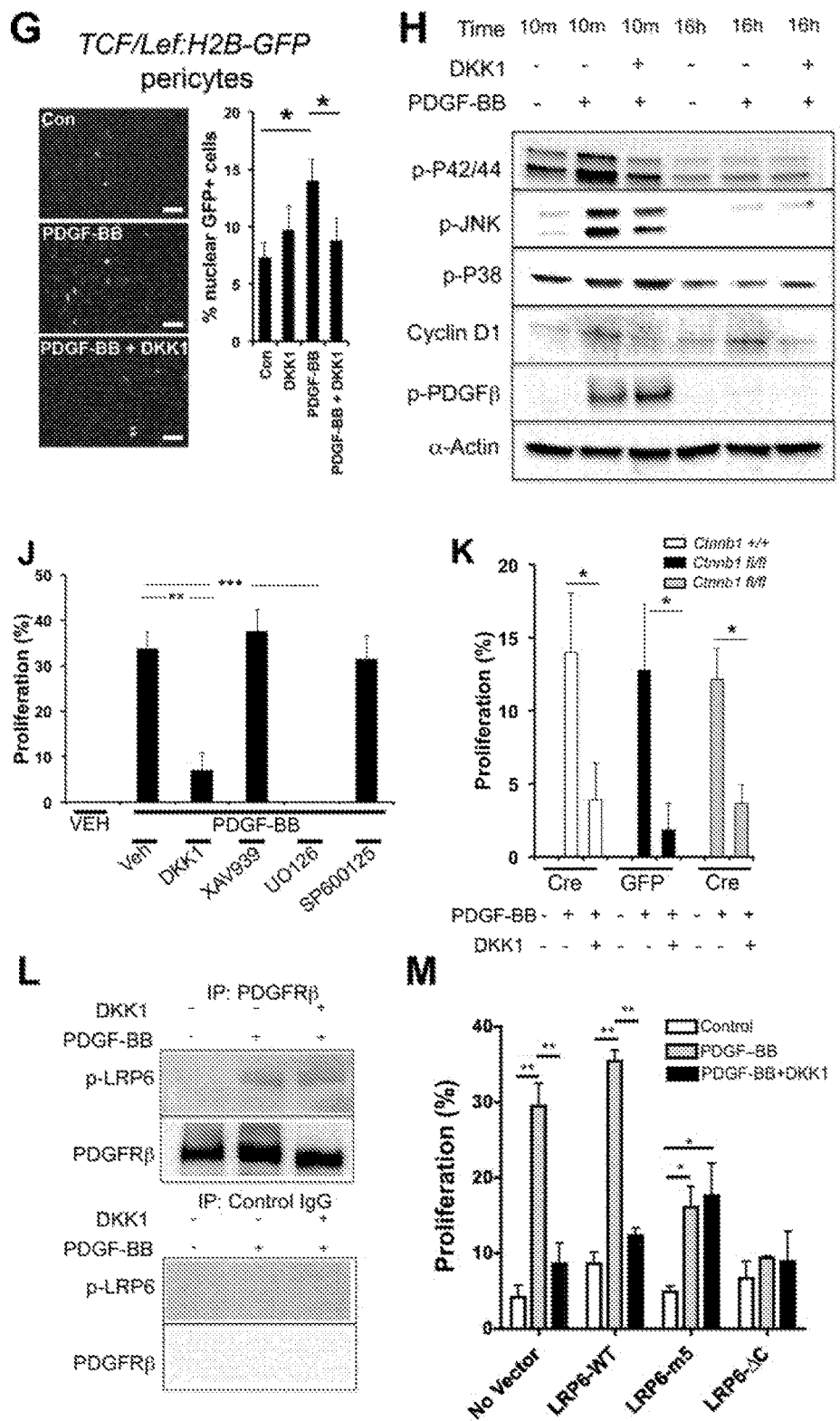

DKK1 blocks PDGF stimulated proliferation of kidney pericytes by an LRP6, P42/P44 MAP kinase dependent mechanism. To study the mechanism of action of DKK1, its effects on primary kidney pericyte cultures, the precursors of myofibroblasts (22, 35) was tested. PDGF and TGFβ signaling in pericytes are important factors in detachment from capillaries and transition to myofibroblasts (23, 37) and as such are important factors in driving fibrosis. CTGF and its homologue CCN1 (Cyr61) have also been implicated in fibrosis and wound healing (38, 39). Kidney pericytes were markedly stimulated by PDGF-BB to enter cell-cycle (FIG. 13A), but the other pro-fibrogenic growth factors had no effect. Unexpectedly, exogenous addition of WNT3a did not stimulate proliferation. DKK1 markedly attenuated PDGF-BB stimulated proliferation (FIG. 13B). PDGF stimulation down-regulated transcripts for activation markers CTGF, αSMA or CollagenIα (1), and DKK1 further down-regulated those transcripts (FIG. 13C) suggesting DKK1 may therefore enhance certain PDGF-mediated transcriptional events. None of the factors applied to pericytes affected viability (FIG. 13D).

In keeping with a link between PDGF signaling and WNT pathway in pericyte proliferation, PDGF regulates a number of WNT ligands, including WNT2, 5a (up) and WNT7a, 10a, 16 (down) (FIG. 13E) at 24 h. But out of keeping with such a link, exogenous WNT3a had no stimulatory effect on proliferation (FIG. 13A). Because DKK1 acts via LRP5 and LRP6 and because PDGF regulates WNT transcripts (FIG. 13E) it was hypothesized that DKK1 blocks the endogenous WNT/β-catenin pathway. Binding of WNT ligands to Frizzled receptors and LRP6 co-receptors leads to activation and phosphorylation of LRP6 (p-LRP6). Surprisingly therefore, PDGF-BB alone stimulates p-LRP6 (FIG. 13F), and DKK1 initially modestly augments p-LRP6 and only inhibits at later timepoints (FIG. 13F, FIG. 6A-C), indicating PDGF may co-activate the WNT/β-catenin pathway, and that DKK1 regulates this co-activation. To test this whether PDGF-BB regulates the WNT/β-catenin pathway in pericytes cultured from the β-catenin reporter mouse (TCF/Lef: H2B-GFP$^{Tr}$) (FIG. 13G) was assessed. After 16 hr of stimulation with PDGF, nuclear β-catenin activity was significantly increased. This increase was inhibited by DKK1 (FIG. 13G), although the extent of β-catenin activation was much lower than the extent of cells triggered into cell-cycle (FIG. 13A), consistent with the possibility that DKK1 inhibits proliferation by a β-catenin-independent pathway. Signaling pathways activated by PDGF-BB but inhibited by DKK1 were therefore explored (FIG. 13H, FIG. 6D). PDGF-BB stimulates the P42/P44 (mitogen activated protein kinase) MAPK signaling pathway and the JNK (c-Jun N-terminal kinase) pathway. DKK1 inhibits both of these responses. PDGF-BB also activates the P38 MAPK pathway, and DKK1 enhances this response, and may explain why DKK1 can enhance PDGF-mediated transcription (FIG. 13C). PDGF-BB enhances CyclinD1 expression (FIG. 13H, FIG. 6D), an effect inhibited by DKK1. Although WNT3a alone had no apparent impact on cell proliferation (FIG. 13A), it nevertheless stimulated activation of LRP6 and accumulation of CyclinD1 (FIG. 6E), providing evidence that LRP6 activation by PDGF-BB results in distinct signaling versus activation by WNT3a.

Figure 7:
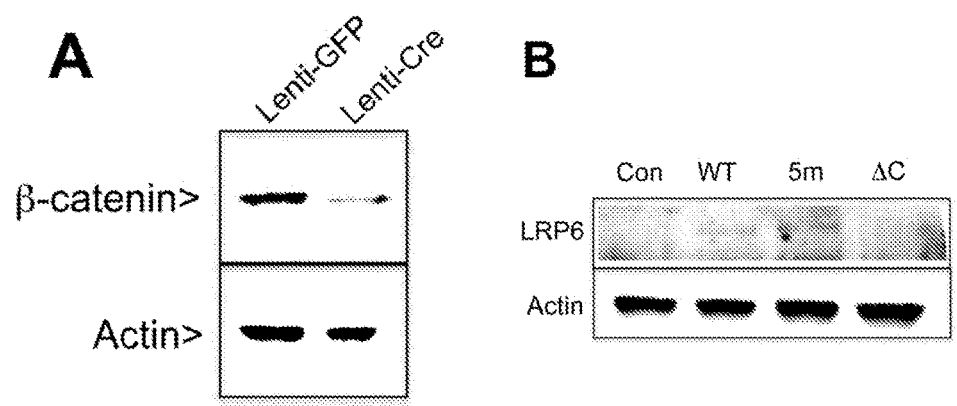
FIG. 7. Silencing genes in pericytes and expressing genes in fibroblasts. (A) Western blot for β-catenin showing the effect 48 h after transduction of primary pericytes from Ctnnb1fl/fl mice with Lentivirus coding for GFP or Lentivirus coding for Cre recombinase. (B) Western blot showing expression of human LRP6 (detecting cytoplasmic domain) in 3T3 fibroblasts 24 h after transfection with vectors for human LRP6 vectors: WT, 5 m or ΔC. Note ΔC does not have a cytoplasmic tail so is not detected.

Because DKK1 specifically inhibits PDGF-stimulated P42/P44 MAPK and JNK activation (FIG. 13H) the relative importance of these pathways was tested using specific inhibitors. The P42/P44 inhibitor U0126 completely replaces DKK1 function in PDGFBB-stimulated pericyte proliferation (FIG. 13J), whereas the JNK inhibitor SP600125 had no impact. Because there was no apparent linkage between the PDGF-BB-mediated activation of the WNT/β-catenin signaling pathway and its capacity to stimulate proliferation, whether the WNT/β-catenin pathway was necessary for PDGF-mediated proliferation using a small molecule inhibitor of β-catenin XAV939 (a Tankyrase inhibitor that antagonizes WNT/β-catenin signaling by stabilizing steady-state levels of Axin, a negative regulator of β-catenin) was tested. Strikingly, XAV939 had no effect on PDGF-BB stimulated proliferation (FIG. 13J). To confirm this finding cultured pericytes from kidneys homozygous for the floxed alleles of β-catenin (Ctnnb1$^{fl/fl}$) underwent recombination in vitro by transduction with Lenti-Cre virus, and Lenti-GFP virus was used as a control that does not catalyze recombination. 100% of pericytes were transduced by GFP expression and β-catenin protein was lost 48 h after transduction with Lenti-Cre (FIG. 7). Pericytes lacking β-catenin responded similarly to pericytes with β-catenin to PDGF and its inhibition by DKK1 (FIG. 13K) confirming PDGF stimulates, and DKK1 inhibits proliferation independently of canonical WNT pathway, even though LRP6 is activated. To study whether DKK1 mediates its effects through an alternative cell surface signaling mechanism or whether LRP6 is necessary for the PDGF signaling pathway in this context, PDGFRβ was immunoprecipitated from pericytes and pulled down active pLRP6 only when the receptor was engaged with ligand (FIG. 13L) indicating a close relationship between the two receptors at the time of signaling. Second, dominant negative mutated forms of LRP6 in a mouse embryonic fibroblast cell line (3T3) which endogenously expresses PDGFRβ was overexpressed (FIG. 13M, FIG. 7).

Expression of two different dominant negative forms of LRP6, but not the WT form, was sufficient to inhibit proliferation of 3T3 cells in response to PDGF-BB and prevent DKK1 effects (FIG. 13M), indicating DKK1 inhibits proliferation through signaling via LRP6, and revealing that LRP6 can be detected in a complex containing PDGFRβ.

Figure 8:
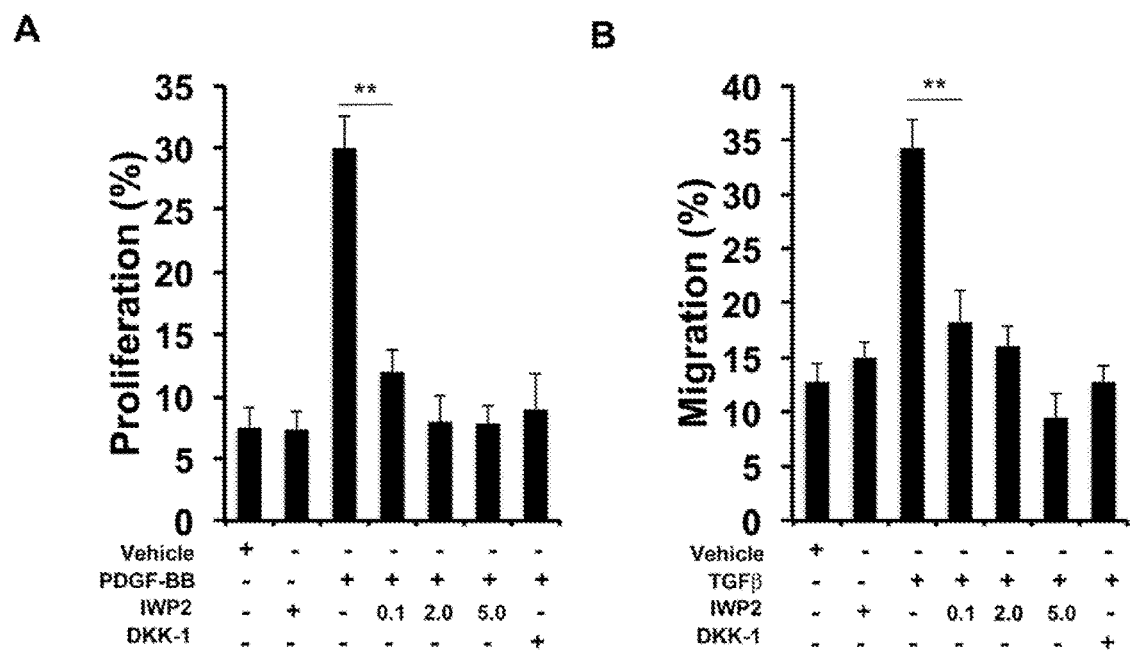
FIG. 8. Inhibition of Porcupine Homologue by IWP2 prevents proliferation or migration of pericytes in response to PDGF-BB or TGFβ respectively. (A) Graph showing proliferation of primary pericytes in response to PDGF-BB in the presence of concentrations of IWP2. (B) Graph showing migration of primary pericytes in response to TGFβ in the presence of concentrations of IWP2 (n=5/group. $**P<0.01$).

Finally since LRP6 is required for PDGF-induced proliferation whether WNT ligands were necessary for PDGF responses blocking endogenous WNT secretion in primary pericyte cultures using the Porcupine homologue inhibitor, IWP2 was assessed (FIG. 8). Porcupine homologue is required for palmitoylation and secretion of all WNTs from cells (40). IWP2, blocked PDGF stimulated proliferation in a dose dependent manner, without affecting viability, suggesting that WNT engagement of LRP6 at the cell surface is necessary for PDGF responses in pericytes.

Figure 12:
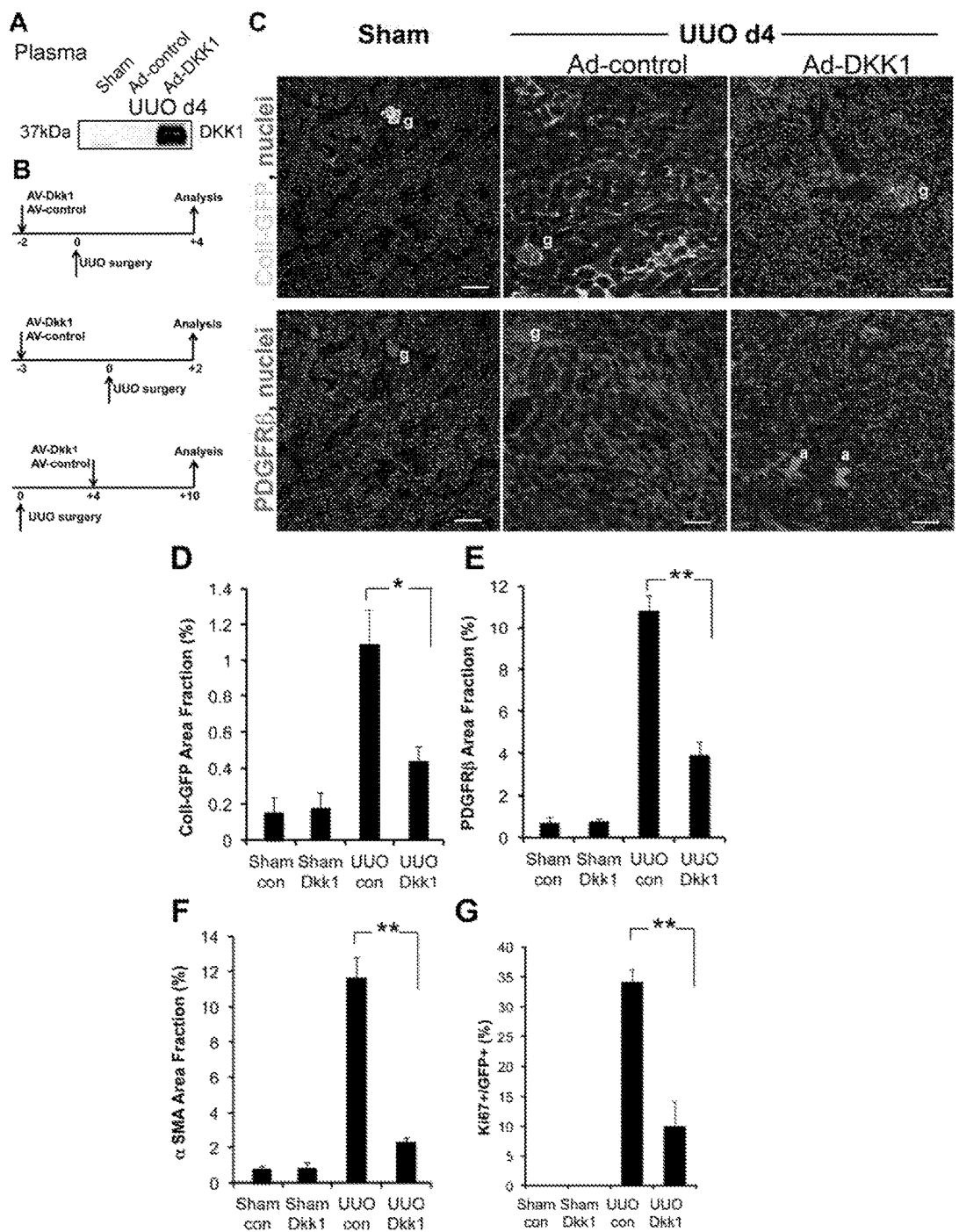
FIG. 12. DKK1 blocks pericyte activation, transition to myofibroblasts, and reverses myofibroblast activation in vivo, inhibiting fibrogenesis, capillary rarefaction and inflammation. (A) Western blot of 5μl of plasma from mice 5d after IV injection of Adcontrol or AdDKK1 or from sham surgery mice with control. (B) Experimental schemata for adenoviral administration, kidney injury and analysis in the UUO model. (C-N) Prevention Studies. (C) Low magnification confocal images of kidney cortex from Sham operated or d4 after UUO kidneys from Coll-GFP$^{Tr}$ mice that received Adcontrol or AdDKK1, 6 days previously, showing Coll-GFP cells or PDGFRβ cells (g=glomerulus, a=arteriole) (D-F) Graphs showing quantification of Coll-GFP cells, PDGFRβ cells or αSMA cells in kidney on d4 after UUO. (G) Proportion of Coll-GFP cells that express the proliferation marker Ki67. (H and J) Western blot of GFP (H) or αSMA/CTGF in whole Coll-GFP mouse kidney from d4 after UUO (K) Quantification of macrophage numbers in kidney sections detected by F4/80 staining. (L) Western blot quantifying canonical WNT signaling by detecting the H2B-GFP fusion protein after AdDKK1 vs Adcontrol treatment of TCF/Lef:H2B-GFP$^{Tr}$ reporter mice during UUO kidney injury. (M) Sirius red stained kidneys d10 after UUO (N) Morphometry of Sirius red stain collagen (upper) or Q-PCR for Col1a1 transcripts (lower panel) d10 after UUO in mice treated with Adcontrol vs AdDKK1 (P-R) Reversal studies. Confocal Images (P) and morphometric quantification (Q) of αSMA staining d10 after UUO in mice treated with Adcontrol or AdDKK1 from d+4. (R) Quantification of capillary density at d10 UUO. Note that rarefaction occurs in response to kidney disease but DKK1 partially reverses rarefaction. (S-T) Pericyte detachment. Images and quantification of pericyte area in Coll-GFP mice 2d after UUO in the presence of circulating DKK1 or control. Note injury to the kidney stimulated pericyte spreading and detachment from endothelium (arrowheads). (*P<0.05, **P<0.01. Experiments are n=4-6/group).
Figure 12:
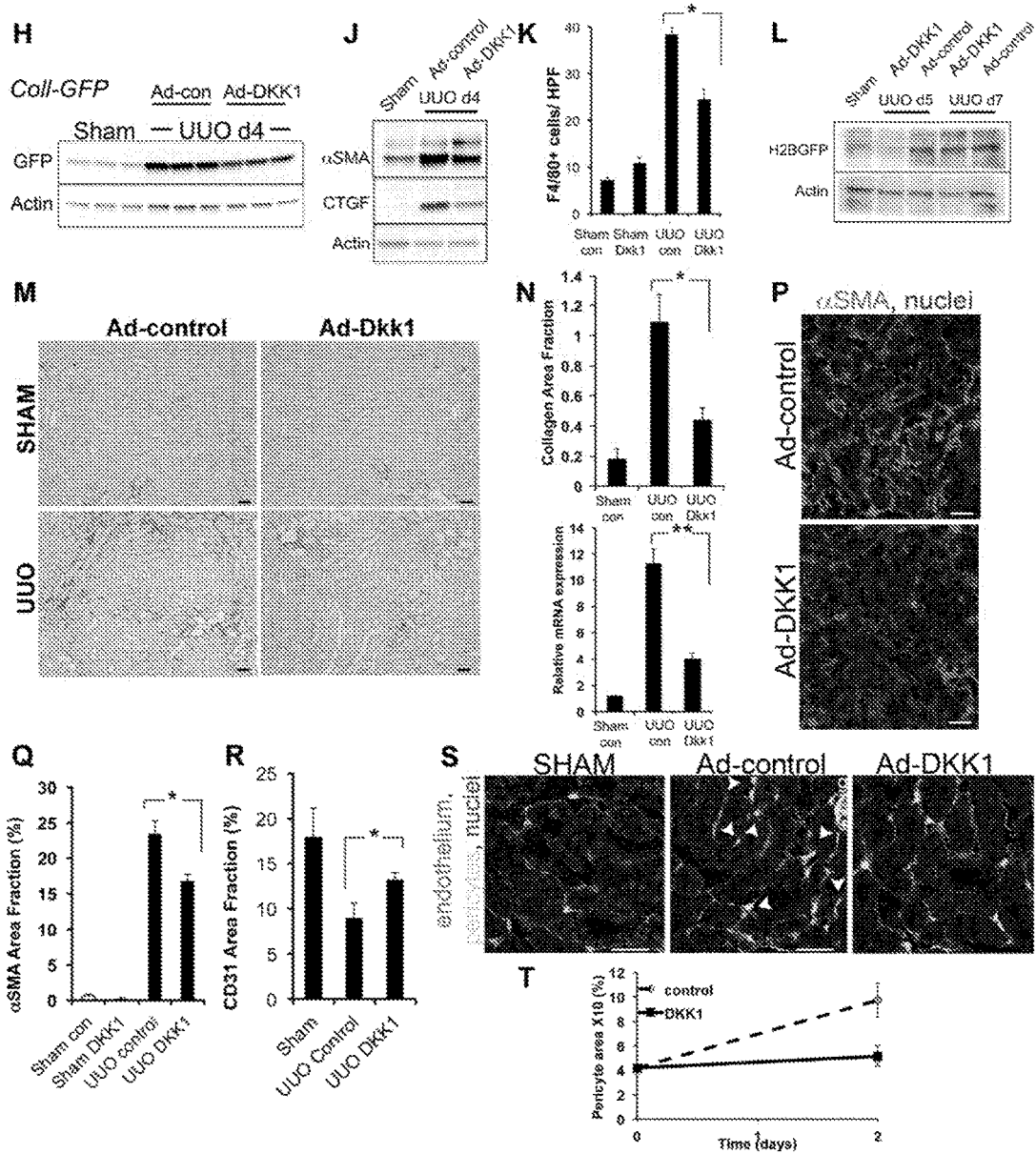
Figure 14:
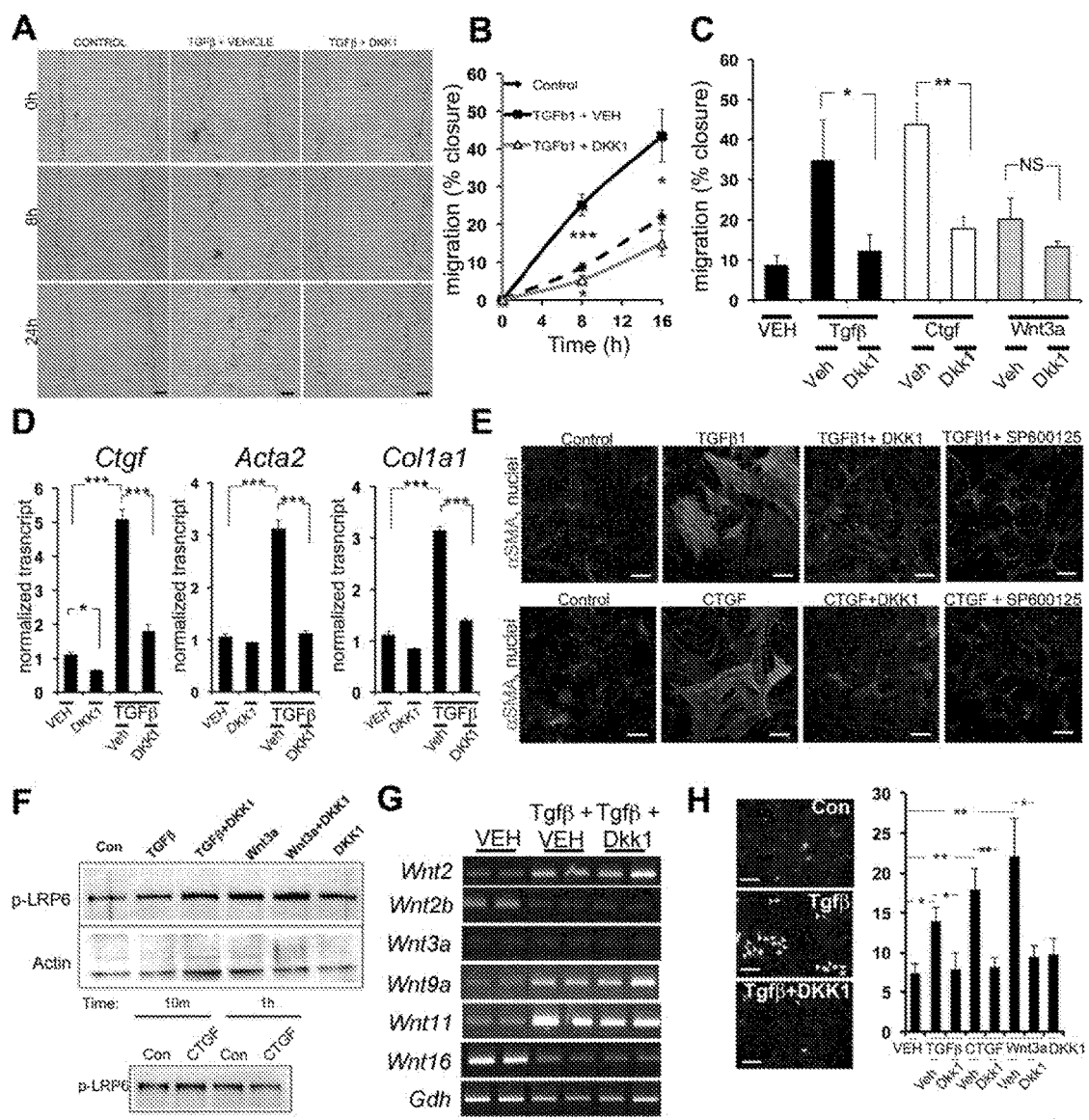
FIG. 14. DKK1 blocks TGFβ and CTGF mediated migration of pericytes in vitro predominantly by a non-canonical, LRP6 dependent, JNK dependent mechanism. (A-B) Images (A) and timecourse graph (B) showing migration of kidney pericytes induced by TGFβ and blocked by DKK1 (bar=50 µm). (C) Graph of migration at 16 h by pericytes stimulated by TGFβ, CTGF and also weakly by WNT3a. All are blocked by DKK1. (D) Q-PCR of genes associated with cell activation in pericytes. (E) Fluorescence images of αSMA showing the cytoskeleton of primary pericytes in control conditions, or under stimulated conditions for 24 h (bar=25 µm). (F) Western blots showing phosphorylated LRP6 levels in pericytes 10 mins after activation with TGFβ, or WNT3a in the presence of vehicle or DKK1 (upper), and after activation with CTGF (lower) (G) 30 cycle RT-PCR showing the effect of TGFβ or TGFβ+DKK1 on WNT ligand expression at 8 h (H) Fluorescence images and data quantifying nuclear GFP+(green) in TCF/Lef:H2B-GFP$^{Tr}$ canonical WNT reporter pericytes, 16 h after stimulation with cytokines in the presence or absence of DKK1. (J) Western blot timecourse of phosphorylated forms of P42/P44, JNK and P38, LRP6 and FAK in pericytes activated by TGFβ or TGFβ+DKK1. (K) Western blots of phosphorylated forms of P42/P44, JNK and P38, and FAK in pericytes activated by CTGF or CTGF+DKK1. (L) Graph showing the effect DKK1 or canonical WNT inhibitor XAV939, TGFβ R1 kinase inhibitor SB431542, P42/P44 inhibitor U0126, or JNK inhibitor SP600125 on TGFβ stimulated (upper) or CTGF stimulated (lower) migration in quiescent pericytes. (M) Graph showing the effect of TGFβ on migration of Ctnnb1$^{fl/fl}$ pericytes that underwent in vitro recombination by expressing Cre recombinase vs Ctnnb1$^{fl/fl}$ pericytes that expressed control protein GFP. (N) Western blot of pericyte proteins immunoprecipitated by anti-TGFβR1 antibodies or control antibodies, detecting p-LRP6 or TGFβ R1 (P) Graph showing the effect of expression of LRP6 (wild type), or dominant negative forms of LRP6, 5 m or ΔC on 3T3 fibroblast migration in response to TGFβ and DKK1. (*P<0.05, P<0.01, *P<0.01. Experiments are from n=4-7/group. All blots representative of 3 expts).
Figure 14:
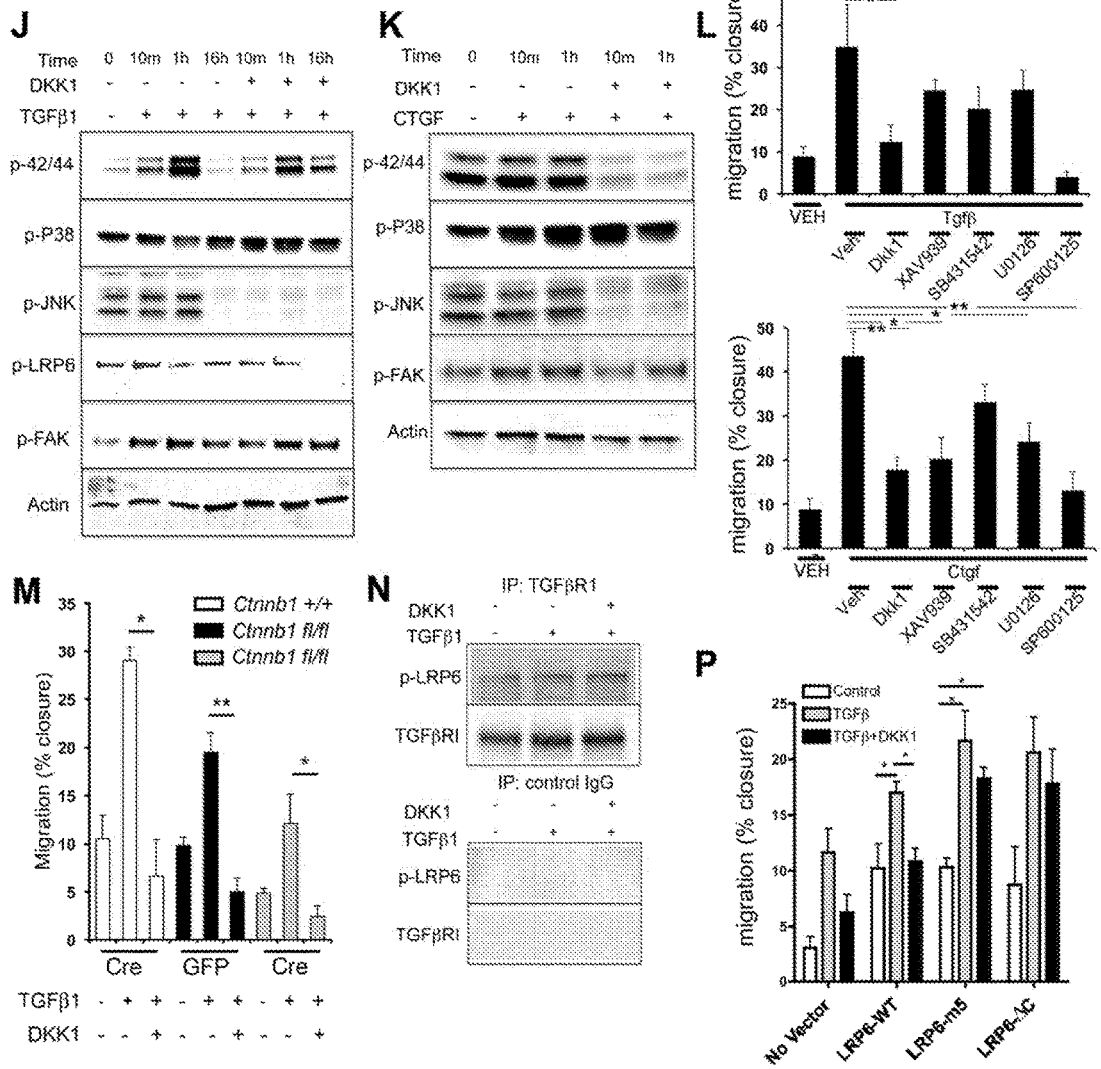

DKK1 inhibits TGFβ and CTGF stimulated activation of kidney pericytes via an LRP6, JNK dependent mechanism. The described in vivo studies showed DKK1 prevents pericyte activation, detachment from capillaries, migration and expression of the myofibroblast marker αSMA (FIG. 12). Previous and current studies (22, 37) suggest that PDGFR signaling does not impact these pericyte changes directly. The effect of DKK1 on activation and migration of pericytes in response to other cytokines implicated in these processes was therefore tested (41, 42). By contrast to PDGF, treatment with TGFβ markedly and rapidly stimulates pericyte migration (FIG. 14A-C), and over 48 h-72 h up-regulates Collagen genes and the intermediate filament αSMA (FIG. 14D). Similar observations on migration were made by treatment of pericytes with CTGF (FIG. 14C-D), an extracellular protein that may signal via β1-integrins, LRP1 and possibly LRP6 (43-45), and with CCN1 (FIG. 9A). TGFβ and CTGF promote marked cytoskeletal reorganization of contractile filaments in pericytes after 24 h of cytokine treatment (FIG. 14E). DKK1 inhibits all migratory, activatory and cytoskeletal changes in pericytes in response to TGFβ or CTGF (FIG. 14A-E), but has no impact on migration in response to CCN1 (FIG. 9A). Strikingly, primary cultures of kidney epithelial cells have high endogenous migration that is weakly responsive to these cytokines. DKK1 has nonsignificant effect on these (FIG. 43), suggesting DKK1 has a major effect on pericytes, not epithelium.

Figure 9:
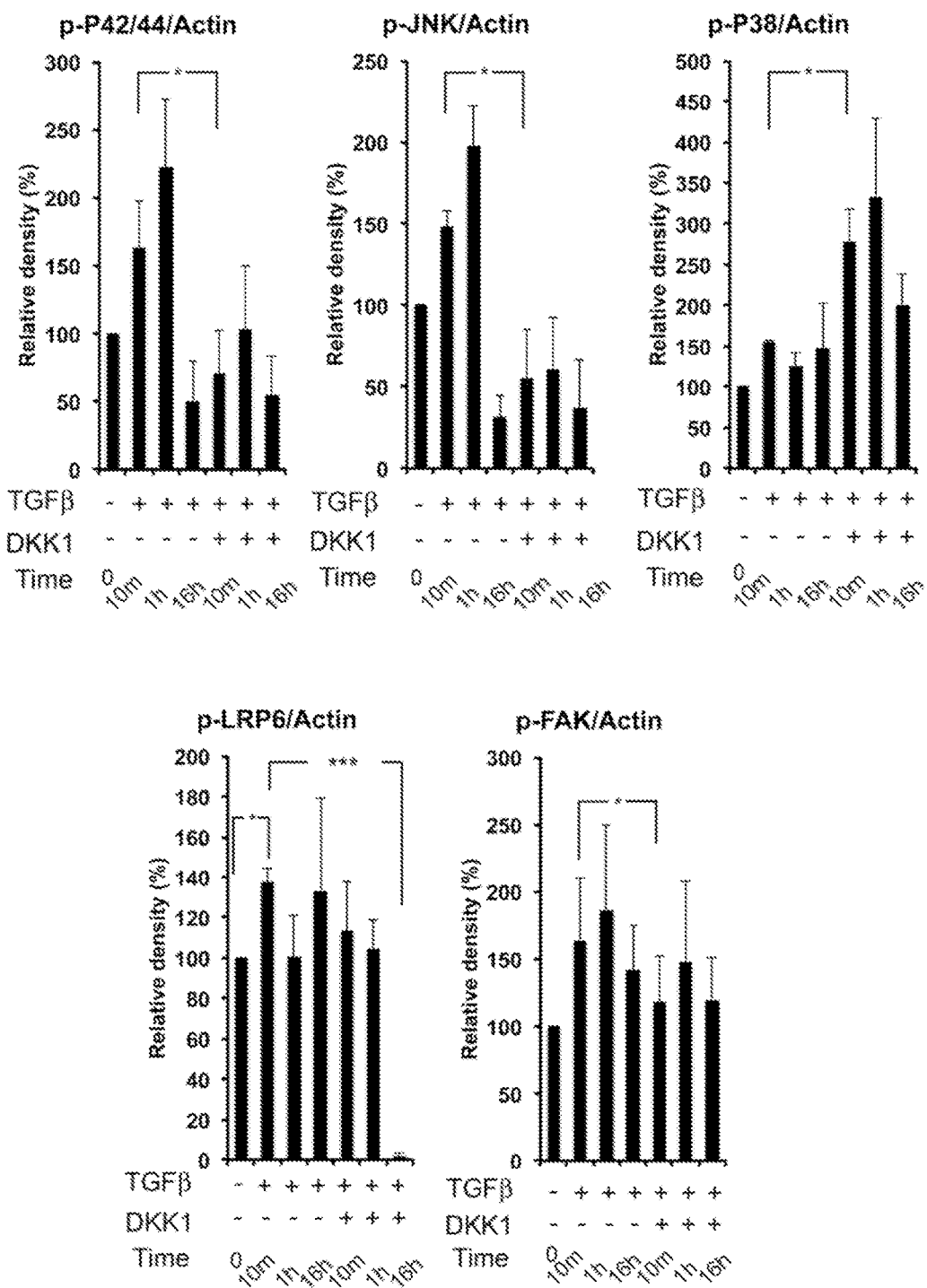
FIG. 9. Factors affecting migration and gene activation in primary pericyte cultures. (A) Graph showing the effect, 24 h after application of CCN1 or CCN1 in combination with other factors, on migration of primary pericyte cultures. CTGF was used as a positive control. (B) Graphs showing relative density of bands from 3 separate experiments performed as shown in FIG. 14F. (C) Western blot showing the effect of TGFβ and DKK1 on the phosphorylation of the SMAD2/3 protein. Note DKK1 does not diminish p-SMAD in the presence of DKK1. (D) Graphs showing relative density of bands from 3 separate experiments performed as shown in FIG. 14J. ($*P<0.05$, $**P<0.01$, Experiments are from n=3-4/group).

The impact of DKK1 on activation of LRP6 in the context of the activating ligands was next tested. TGFβ, and CTGF both activate LRP6 within minutes of cytokine exposure and WNT3a also stimulates LRP6 activation (FIG. 14F, FIG. 9B, FIG. 6E). Within 10 minutes of initiation of signaling, DKK1 weakly activates LRP6 (FIG. 6C) and does not block the activation triggered by TGFβ or WNT3a (FIG. 9, FIG. 14F). In all activation pathways, however, LRP6 was deactivated by DKK1 after 16 h (FIG. 6) indicating LRP6 is rapidly activated by non-WNT ligands and that DKK1 initially either weakly augments that signal, or does not affect it, but at later time points strongly silences it. Because DKK1 blocks TGFβ-mediated changes to pericytes, whether TGFβ signals via the WNT/β-catenin pathway directly or indirectly was tested.

TGFβ regulates WNT ligands in pericytes at 24 h (WNT2, 9a, 11 up and WNT2b, 16 down) (FIG. 14G) but DKK1 had no impact on these changes. Both TGFβ and CTGF triggered nuclear β-catenin activity in pericytes (FIG. 14H) which was inhibited by DKK1, but, similarly to PDGF effects, it occurred in a minority of cells, suggesting TGFβ and CTGF may regulate pericyte activation via WNT/β-catenin pathway and that DKK1 may inhibit via the same pathway.

Because DKK1 inhibits PDGFR signaling in pericytes via the MAPK pathways, not β-catenin, the effect of DKK1 on TGFβ and CTGF-mediated signaling was tested. Both TGFβ and CTGF stimulate the P42/P44, P38 and JNK pathways. DKK1 blocks activation of P42/44 and JNK pathways and augments activation of P38 pathway (FIG. 14J-K). FAK is activated by both TGFβ and CTGF and inhibited by DKK1 (FIG. 14J-K). To test whether components of these DKK1-regulated signaling cascades are responsible for the impact on migration, the effect of DKK1 on TGFβ activation of the canonical pathway by measuring SMAD activation was measured (FIG. 9C), but SMAD activation was unaffected.

Next small molecule inhibitors of TGFβR1 (SB431542), JNK-activation (SP600125), P42/P44-activation (U0126) or β-catenin-activation (XAV939) were used in TGFβ-stimulated or CTGF-stimulated migration assays. Whereas P42/P44, TGFβ R1 and β-catenin inhibitors had no significant effect on TGFβ-stimulated migration, JNK inhibitors completely blocked migration (FIG. 14L, FIG. 9D) to TGFβ, suggesting DKK1-mediated silencing of JNK signaling pathway is central to its ability to block TGFβ-stimulated migration. Inhibition of CTGF-mediated migration was independent of TGFβ R1 activation, was partially dependent on β-catenin and P42/P44 activation and, was most dependent on JNK activation (FIG. 14L), highlighting similarities and differences from TGFβ-mediated migration. CCN1-mediated migration occurred independently of P42/44 and JNK pathways (FIG. 9A). Because XAV939 showed little effect in TGFβ-mediated migration, pericytes lacking β-catenin as described above were generated (FIG. 13K). Compared with controls, in the absence of β-catenin DKK1 completely blocked TGFβ-stimulated migration. However, overall (non-stimulated) migration was reduced in the absence of β-catenin.

These studies indicate that DKK1 can also function independently of WNT/β-catenin signaling, but that the WNT/β-catenin pathway plays a role in the underlying tendency to migrate. To test whether LRP6 also associated with the TGFβ R complex, TGFβ R1 was immunoprecipitated and p-LRP6 was co-precipitated in resting cells. This association was increased upon active signaling (FIG. 14N). To determine the role of LRP6 in TGFβ-stimulated migration expression of the dominant negative LRP6 mutants in fibroblasts as described above were studied (FIG. 13M). Strikingly, although TGFβ-mediated migration occurred in the presence of mutant LRP6, DKK1 was now ineffective (FIG. 14P). Therefore DKK1 inhibits TGFβ migration by an LRP6-dependent mechanism, and active LRP6 can be detected in a signaling complex with TGFβ R1. The fact that TGFβ stimulates migration in the presence of dominant negative LRP6 but DKK1 no longer functions suggests, that the endogenous LRP6 may still be able to interact with TGFβ whereas DKK1 binds equally to the mutant forms, but further studies will be required to understand LRP6 interactions with TGFβ R1. Finally to test the role of WNTs in TGFβ mediated migration and in DKK1 inhibition block endogenous WNT secretion using IWP2 as described above (FIG. 8). In this setting TGFβ-stimulated migration was completely blocked, suggesting that WNT engagement of LRP6 at the cell surface is necessary for TGFβ response in pericytes.

Figure 15:
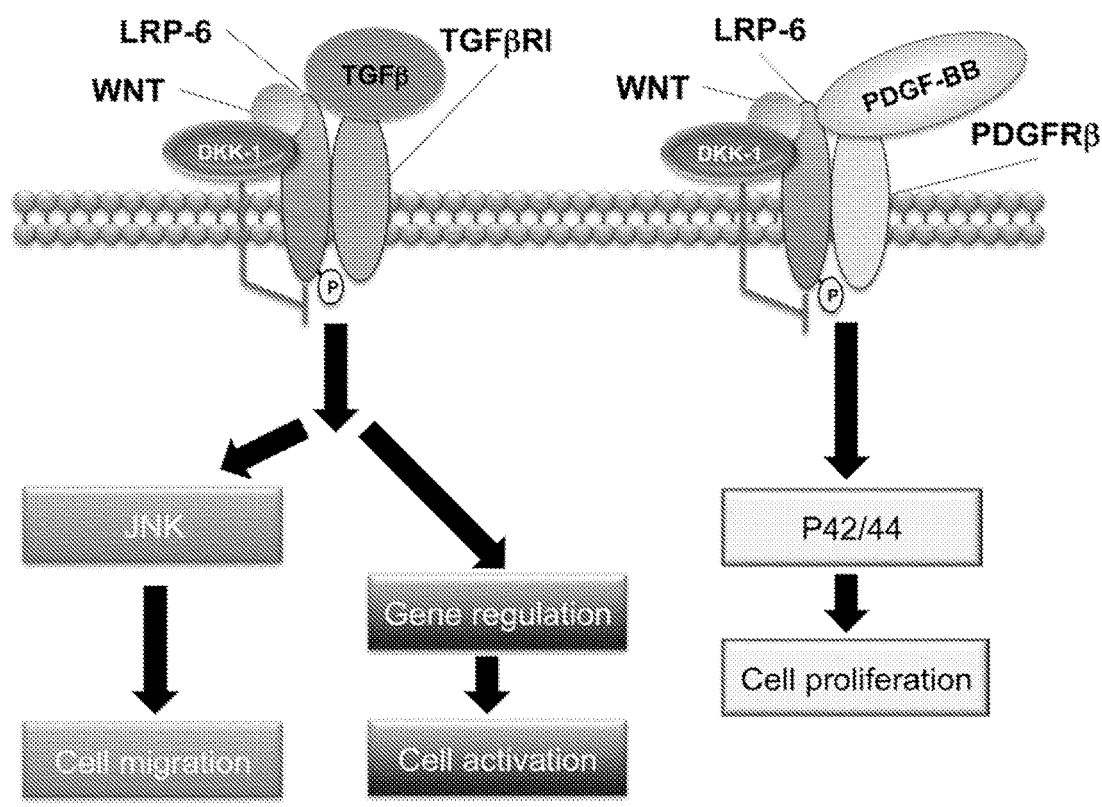
FIG. 15. Schema showing the effect of LRP6 and DKK1 on TGFβ and PDGFBB signaling in kidney pericytes. When LRP6 is bound by WNT ligands including (Wnt2,5a,7a,7b, 9a,11 or 16) and PDGF or TGFβ ligands bind to their cognate receptors, LRP6 interacts closely with PDGFRβ or TGFβR1 respectively resulting in activation of MAPK pathways that are critical to transducing proliferative, migratory and activating signals. Through binding to LRP6, DKK1 blocks all of these critical signals triggered by PDGFs, TGFβ and CTGF.

These studies identify LRP6 and signaling pathways downstream of LRP6 as novel therapeutic targets to intervene in fibrogenesis of the kidney. In addition, they identify the soluble protein DKK1 and its receptor LRP6 as important co-factors in multiple signaling pathways activated by TGFβ, CTGF and PDGF, as well as Frizzled in mesenchymal cells (FIG. 15). Since these multiple pathways are known to contribute to the development of fibrosis and its longer-term consequences on organ function, therapeutically-delivered DKK1 or therapeutic targeting of the LRP6 receptor are attractive novel strategies for treating fibrosis, microvascular inflammation, tubule injury and microvascular rarefaction. Recent studies indicate that mesenchyme-derived cells, either pericytes or resident fibroblasts, are present in all our organs and tissues and are the primary source of scar-forming myofibroblasts in multiple tissues (22, 46). It is likely, therefore, that the DKK1/LRP6 signaling pathway will regulate fibrogenesis in multiple organs and tissues.

The MAPK signaling pathways from TGFβR signaling, CTGF signaling and PDGFR signaling appear to be functionally critical in the mesenchyme-derived perivascular cells in kidney. These pathways have received relatively little attention, and earlier studies have assumed that the canonical pathways activated by these receptors have been dominant in the process of fibrogenesis (37, 47), but further studies should focus on these pathways in pericytes and fibroblasts. Since these pathological signaling receptors are also important in normal embryogenesis, one possibility is that MAPK pathways play a more pathological role whereas the canonical pathways are more important in development and homeostasis. Our studies show that LRP6 (and potentially LRP5) interact physically with PDGFRβ and TGFβ R1 upon receptor ligation (FIG. 15). It is possible, therefore, that LRP6 is responsible for transducing the signal that activates the MAPK pathways. Further studies should address this question. The fact that LRP6 can function as a co-receptor for multiple pathways raises the question whether it requires an extracellular ligand to effect this interaction distinct from WNT ligands. It is likely that soluble ligands such as TGFβ and PDGF are presented at the cell surface bound to extracellular modulators, and that these modulators may be responsible for recruitment of LRP6. The studies also indicate that in pericytes and myofibroblasts, CTGF activates cells independently of TGFβ, whereas previous studies have suggested that CTGF augments TGFβ responses in fibrogenesis (48). These studies suggest that CTGF has a distinct receptor on pericytes and myofibroblasts, which has not been fully appreciated. Further studies should define the CTGF receptor in these cells, and the interaction of LRP6 with that receptor.

Genetic studies of LRP6 and LRP5 function in mice point to their major role in WNT pathway signal transduction in early and later embryogenesis (25). However, the initial studies suggested that LRP5; LRP6 mutations interfered with other signaling pathways, including FGFR1 and Notch Delta (49, 50). Recently, LRP6 mutations have been found not only in humans with reduced bone mineral density, but also in patients with premature cardiovascular disease (51). These studies have also suggested a potential link between LRP6 and PDGFR signaling. Put in the context of our current findings, it suggests that LRP6 may regulate multiple signaling pathways in mesenchyme-derived cells that play critical roles in bone mineralization, arterial wall functions, and microvascular wall functions.

Our studies identify DKK1 as a soluble protein that can inhibit fibrogenesis. DKK1 has been shown to potently inhibit canonical WNT signaling, findings supported by our studies. However, DKK1 weakly activates LRP6 early during its interaction, and only later blocks activity at this receptor. Previous studies of cell lines suggest this blockade occurs without receptor internalization (52). This raises the question as to why DKK1 inhibits downstream signaling. This may be due to a sustained signal rather than an on-off signaling, or it is possible that DKK1 triggers a distinct phosphorylation pattern at LRP6 that is, in fact, inhibitory.

DKK1, is anti-fibrotic and anti-inflammatory by inhibiting multiple signaling pathways in pericytes and myofibroblasts through binding to the cell surface receptors LRP5/-6, which in turn act as co-receptors for multiple signaling pathways.

Recombinant DKK1 protein variants for the inhibition of WNT signaling and the treatment of fibrogenesis and CKD. The preceding studies provide strong evidence for the efficacy of DKK1 or inhibitors of LRP5/6 receptors in the treatment of kidney disease. Next recombinant human and mouse proteins that can be used as protein therapeutic in the treatment of organ scarring and CKD, among other organs and diseases, were generated. The in vivo efficacy studies were based on adenoviral delivery of DKK1 via hepatocellular production of the molecule endogenously. Our goal, however was to evaluate whether recombinant proteins could be generated that have efficacy as a purified delivered therapy, and whether the efficacy could be enhanced by protein engineering. Four recombinant DKK1 protein variants were designed to maximize bioactivity, against the LRP6 receptor binding sites, and to include sequences to optimize expression, secretion and purification and expressed in a high expression plasmid (FIG. 20).

Human DKK1 and mouse DKK1 have signal peptide for secretion (residues 1-31; underlined in the sequences in FIG. 21 below). In the design of the recombinant MGN1004 and MGN1006 this signal sequence has been replaced by the rat serum albumin secretion leader sequence MKWVTFLLLL-FISGSAFS (SEQ ID NO. 56) to optimize the secretion of the recombinant protein when overexpressed in eukaryotic species. Following the signal sequence is an 8xHis-tag to permit affinity purification on a Ni-NTA column. A Glutamine residue is included after the His-tag to permit cleavage of the signal sequence and the affinity tag using DAPzyme such that no extraneous residues are left behind following protease treatment.

MGN1006 corresponds to residues 178-266 of human DKK1 with a rat serum albumin signal peptide, 8xHis-tag and a Glutamine at the N-terminus included for efficient cleavage by DAPzyme. Upon purification with Ni-NTA and cleavage by DAPzyme the resultant protein hDKK1 (178-266) corresponds to the previously identified protease resistant fragment when DKK1 is bound to LRP6 (124). Based on this information hDKK1 (178-266) was predicted to be a stable, folded domain that was sufficient for LRP6 interaction.

MGN1007 corresponds to the minimal Cys-rich domain of mouse DKK1 (residues 195-272) with a signal peptide, 8xHis tag and a Q residue at the N-terminus as in the other constructs described above. That the Cys-domain proteins may have equal or greater efficacy with potentially enhanced drug like properties was evaluated.

Proteins were generated in 293 cells and purified on a Nickel column from the supernatants, the His-tag removed by enzyme reaction and stored in PBS buffer at concentrations of 2 mg/ml. Purity was assessed at >90%, by gel evaluation endotoxin tested at <1000 Eu/mg. Proteins showed stability over freeze thaw recovery was assessed and confirmed to be at high levels (>90%) (FIG. 23). Evaluation of proteins in vitro for efficacy. Next proteins were evaluated for inhibition of canonical WNT pathway activation in the SuperTop Flash (STF) cell line (FIG. 24) in response to WNT 3a. As a positive control mouse DKK1 conditioned media supernatants were used. All recombinant proteins effectively inhibited canonical WNT signaling. The C-domain variants also exhibited strong inhibitory capacity in this assay, but MGN1007 was not generated in sufficient quantity to include comprehensive data in time for this submission.

Figure 24:
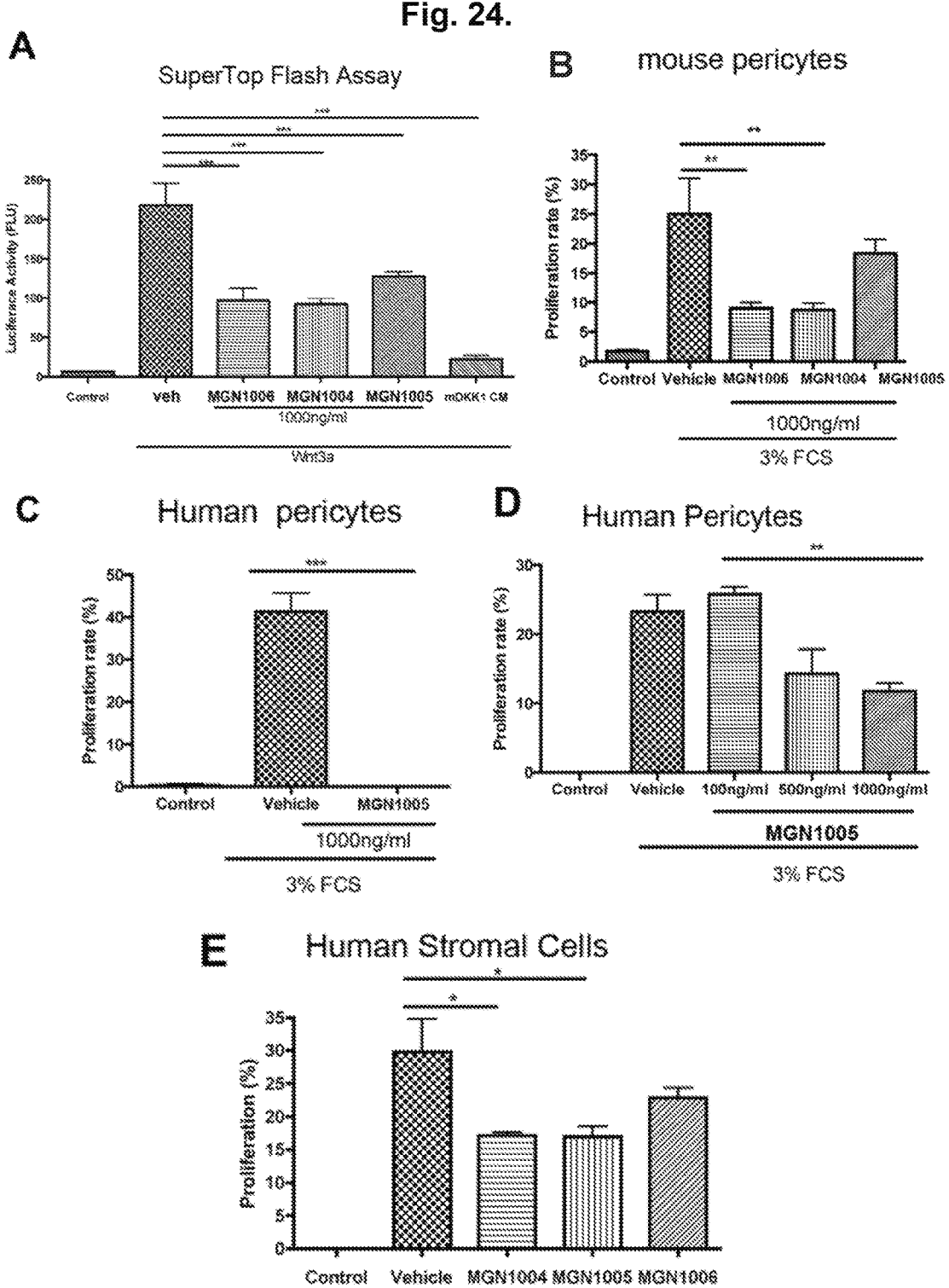
FIG. 24. Effect of recombinant proteins on inhibiting Canonical WNT signaling pathway in a human reporter cell line on inhibiting proliferation of mouse and human myofibroblast progenitor cells. Supertopflash (STF) cell line reports canonical WNT signaling by luciferase activity. In response to WNT3a there is marked increase in signaling which is strongly inhibited by the recombinant proteins. As a positive control mouse DKK1 CM was generated as a conditioned medium from transfected cells as described previously and in (66), incorporated by reference herein for its teachings regarding the same. (B) Mouse primary kidney pericyte cultures were evaluated for proliferation in response to Fetal calf serum (FCS). Proliferation was markedly enhanced and was significantly reduced by MGN1004 and MGN1006. At this concentration MGN1005 reduced proliferation but not as significantly. (C) Human pericytes, precursors for myofibroblasts were evaluated in a similar proliferation assay with MGN1005, which potently inhibited proliferation. (D) In a follow up experiment a dose response experiment was performed showing dose responsiveness. (E) Human fetal kidney stromal cells which include pericytes and fibroblasts (myofibroblast progenitors) were evaluated for efficacy of the recombinant proteins to inhibit proliferation (n=3-5/group, P<0.01, *P<0.001).

Next proteins were tested for their capacity to inhibit pericyte proliferation in a proliferation assay stimulated by serum (FIG. 24). Serum is a highly potent stimulator of proliferation. Mouse kidney pericyte proliferation were markedly inhibited by human or mouse variants (FIG. 24B). Next human pericytes were evaluated. The human variant MGN1005 was highly effective at blocking proliferation of human pericytes and in a repeat experiment this showed dose responsiveness (FIG. 24C-D). MGN1005 is a Cdomain variant and exhibits higher level of potency in limiting proliferation of human brain pericytes. Next the variants were evaluated in human fetal kidney stromal cells which become adult kidney pericytes and fibroblasts (both myofibroblast precursors (FIG. 24E). In these experiments MGN1004 and MGN1005 were effective at reducing stromal cell proliferation.

These studies provide evidence for efficacy of the materials developed as therapeutics for kidney disease. Evaluation of MGN1006 in a short-term mouse model of progressive kidney disease. Next MGN1006 in the mouse model of kidney disease with fibrogenesis was evaluated: MGN1006 was administered to C57BL6) mice 24 h after they underwent surgery to induce unilateral ureteral obstruction (UUO) to the kidney. Compositions were delivered daily by IP injection at one of two different doses (FIG. 25A) vs vehicle (n=5/group).

Figure 25:
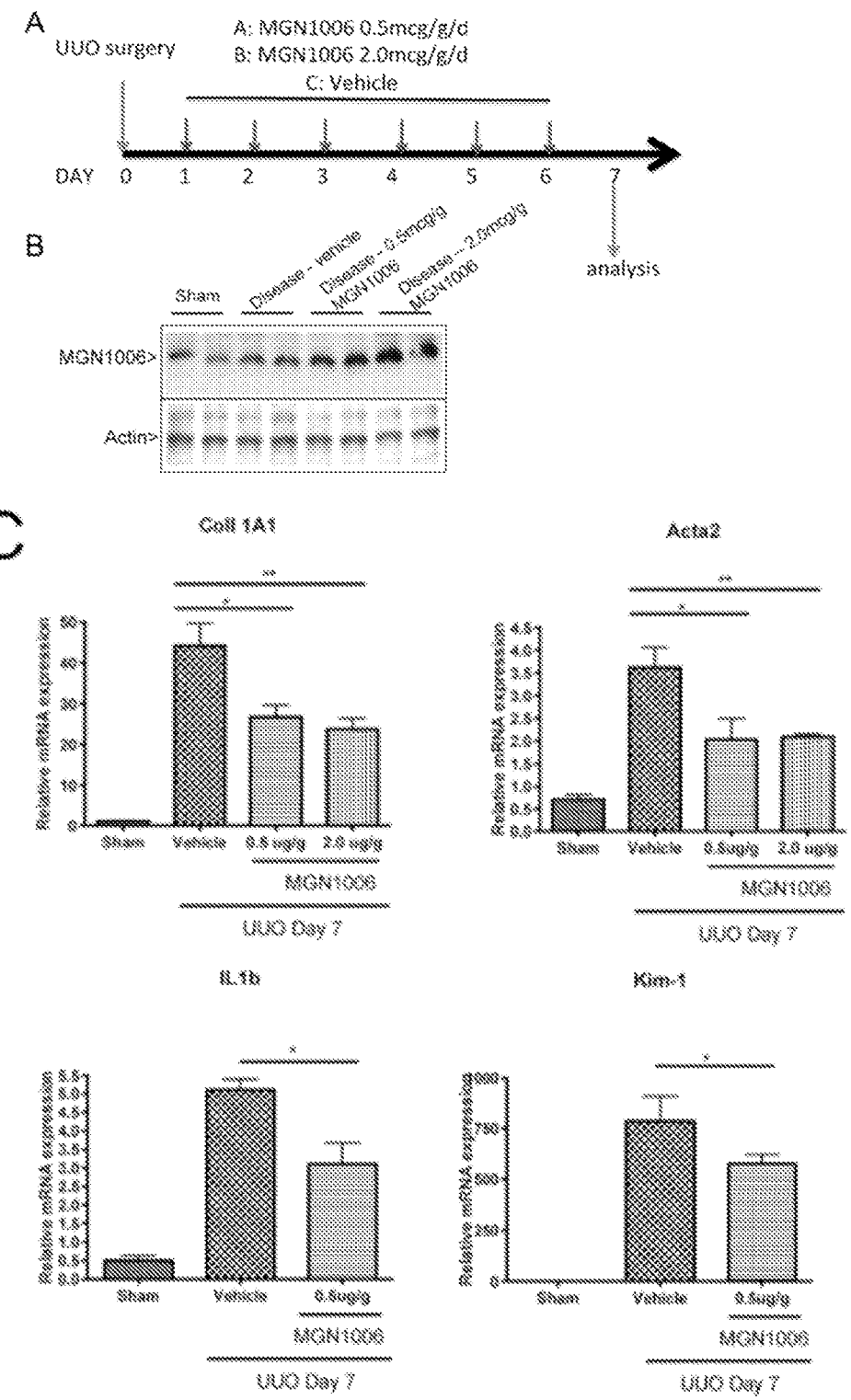
FIG. 25. Treatment of kidney disease in the UUO model of disease with tubular injury, inflammation and fibrosis. (A) Schema showing dosing and frequency of delivery of MGN1006 by IP injection. (B) Western blot of whole kidney showing the level of DKK1 in the kidney. Note that MGN1006 resulted in enhanced levels of DKK1 in the kidney tissue. (C) Q - - - PCR transcript levels of Col1a1, Acta2 (αSMA) involved in fibrogenesis, the inflammatory marker Il1b, and the tubular injury marker Kim1 at d7. Note that MGN1006 was highly effective at reducing fibrogenic genes, the inflammatory marker Il1b and the tubule injury marker Kim1. (D - - - E) Images and quantification showing Myofibroblast appearance as detected by αSMA protein expression was markedly decreased (D) and Fibrosis as assessed by picrosirius red stain of tissue sections (E) was also markedly decreased in this model of kidney disease. (n=5/group, *P<0.05, **P<0.01).

Mice were all healthy and had equal weight at d7 and kidneys were harvested for analysis. Transcript levels showed marked reduction in fibrogenic gene activation (FIG. 25B) with a tendency toward dose responsiveness. In addition a marker of inflammation, Il1b was reduced at the transcript level and the production of Kim1, a highly sensitive marker of tubular injury was also reduced by the actions of MGN1006. Tissue sections of whole kidney showed that expression of the myofibroblast marker αSMA was substantially reduced (FIG. 25D) and Fibrosis, quantified by staining kidney sections with Sirius red stain was also substantially reduced (FIG. 25E). These studies independently verify the efficacy of DKK1 and show that the newly engineered recombinant protein(s) are well tolerated and have efficacy in treating the manifestations of CKD.

Future studies further demonstrate the beneficial uses of the present disclosure. Future studies demonstrate that DKK-1 reduces kidney disease in one or more complementary longer term preclinical models of CKD either the Alport Nephropathy model and/or the diabetic nephropathy model and show that dose/response are linked following subcutaneous or intraperitoneal dosing.

Future studies will include patients with diabetic nephropathy, the largest disease group with CKD, but may also include patients with ischemic CKD because the mechanisms of disease are broadly similar and this is the second largest group of patients. The study will demonstrate that DKK-1 (and modified versions thereof) are effective as adjunct therapies to renin angiotensin system blockade in the treatment of patients with type 2 diabetes mellitus with CKD stage 3b and persistent microalbuminuria or frank albuminuria and/or patients without type 2 diabetes mellitus with CKD stage 3b persistent microalbuminuria or frank albuminuria. All patients will have a 6 month run in period to determine kidney function (estimated glomerular filtration rate (eGFR)), eGFR decline, albuminuria levels, blood pressure control and requirements. This demonstration will be based on "therapeutic success" at 6 months, where therapeutic success is defined as one or more of: (a) conversion from albuminuria to microalbuminuria or normoalbuminuria, as measured by an albumin/creatinine ratio (ACR), with at least a 25% reduction in ACR relative to baseline ACR; (b) a 50% reduction in ACR relative to baseline ACR in a single Phase 3 study; (c) improvement in eGFR; (d) a reduction in the rate of decline of eGFR compared with the 6 month run in period or (e) improvement in blood pressure control.

Evidence may also be collected that DKK-1 blocks progression of all of the features of CKD caused by disorders including ischemia, diabetes, and chronic glomerulonephritis. In addition to fibrosis, these features include, inflammation, epithelial disease and capillary destruction.

As indicated, the practice of the present disclosure can employ, unless otherwise indicated, conventional methods of virology, microbiology, molecular biology and recombinant DNA techniques within the ordinary skill of the art. Such techniques are explained fully in the literature; see, e.g., (117-123) each of which is incorporated by reference herein for its teachings regarding the same.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would result in a statistically significant reduction in the effectiveness of a scarring treatment disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES

1. Yu H M, et al. (2005) The role of Axin2 in calvarial morphogenesis and craniosynostosis Development 132: 1995-2005.
2. Lin S L, et al. (2010) Macrophage WNT7b is critical for kidney repair and regeneration Proc Natl Acad Sci USA 107:4194-4199.
3. Humphreys B D, et al. (2009) Fate tracing reveals the pericyte and not epithelial origin of myofibroblasts in kidney fibrosis Am J Pathol 176:85-97.
4. Castano A P, et al. (2009) Serum amyloid P inhibits fibrosis through Fc gamma Rdependent monocyte-macrophage regulation in vivo Sci Transl Med 1:5ra13.
5. Chau B N, et al. (2012) MicroRNA-21 promotes fibrosis of the kidney by silencing metabolic pathways Sci Transl Med 4:121ra118.
6. Lin S L, et al. (2011) Targeting endothelium-pericyte cross talk by inhibiting VEGF receptor signaling attenuates kidney microvascular rarefaction and fibrosis Am J Pathol 178:911-923.
7. Lin S L, Kisseleva T, Brenner D A, & Duffield J S (2008) Pericytes and perivascular fibroblasts are the primary source of collagen-producing cells in obstructive fibrosis of the kidney Am J Pathol 173:1617-1627.

8. Schrimpf C, et al. (2012) Pericyte TIMP3 and ADAMTS1 modulate vascular stability after kidney injury J Am Soc Nephrol 23:868-883.
9. Dolbeare F, Gratzner H, Pallavicini M G, & Gray J W (1983) Flow cytometric measurement of total DNA content and incorporated bromodeoxyuridine Proc Natl Acad Sci USA 80:5573-5577.
10. Limsirichaikul S, et al. (2009) A rapid non-radioactive technique for measurement of repair synthesis in primary human fibroblasts by incorporation of ethynyl deoxyuridine (EdU) Nucleic Acids Res 37:e31.
11. Ashton A W, et al. (1999) Inhibition of endothelial cell migration, intercellular communication, and vascular tube formation by thromboxane A(2) J Biol Chem 274:35562-35570.
12. Davidson K C, et al. (2012) WNT/beta-catenin signaling promotes differentiation, not self-renewal, of human embryonic stem cells and is repressed by Oct4 Proc Natl Acad Sci USA 109:4485-4490.
13. Ren S, et al. (2005) PPARalpha activation upregulates nephrin expression in human embryonic kidney epithelial cells and podocytes by a dual mechanism Biochem Biophys Res Commun 338:1818-1824.
14. Carpenter A C, Rao S, Wells J M, Campbell K, & Lang R A (2010) Generation of mice with a conditional null allele for WNTless Genesis 48:554-558.
15. Ren S, et al. (2009) Transforming growth factor-beta2 upregulates sphingosine kinase-1 activity, which in turn attenuates the fibrotic response to TGF-beta2 by impeding CTGF expression Kidney Int 76:857-867.
16. Niwa H, Yamamura K, & Miyazaki J (1991) Efficient selection for high-expression transfectants with a novel eukaryotic vector Gene 108:193-199.
17. Chartier C, et al. (1996) Efficient generation of recombinant adenovirus vectors by homologous recombination in *Escherichia coli* J Virol 70:4805-4810.
18. Tamai K, et al. (2004) A mechanism for WNT coreceptor activation Mol Cell 13:149-156.
19. Lupher M L, Jr. & Gallatin W M (2006) Regulation of fibrosis by the immune system Adv Immunol 89:245-288.
20. Hernandez-Gea V & Friedman S L (2010) Pathogenesis of liver fibrosis Annu Rev Pathol 6:425-456.
21. Racusen L C & Regele H (2010) The pathology of chronic allograft dysfunction Kidney Int Suppl:S27-32.
22. Humphreys B D, et al. (2009) Fate tracing reveals the pericyte and not epithelia origin of myofibroblasts in kidney fibrosis Am J Pathol 176:85-97.
23. Lin S L, et al. (2011) Targeting endothelium-pericyte cross talk by inhibiting VEGF receptor signaling attenuates kidney microvascular rarefaction and fibrosis Am J Pathol 178:911-923.
24. Keramati A R, et al. (2011) Wild-type LRP6 inhibits, whereas atherosclerosis linked LRP6R611C increases PDGF-dependent vascular smooth muscle cell proliferation Proc Natl Acad Sci USA 108:1914-1918.
25. Tamai K, et al. (2000) LDL-receptor-related proteins in WNT signal transduction Nature 407:530-535.
26. Clevers H & Nusse R (2012) WNT/beta-Catenin Signaling and Disease Cell 149:1192-1205.
27. Poss K D (2010) Advances in understanding tissue regenerative capacity and mechanisms in animals Nat Rev Genet 11:710-722.
28. Shin K, et al. (2011) Hedgehog/WNT feedback supports regenerative proliferation of epithelial stem cells in bladder Nature 472:110-114.
29. Rodilla V, et al. (2009) Jagged1 is the pathological link between WNT and Notch pathways in colorectal cancer Proc Natl Acad Sci USA 106:6315-6320.
30. Dong Y, et al. (2005) WNT-mediated regulation of chondrocyte maturation: modulation by TGF-beta J Cell Biochem 95:1057-1068.
31. Lin S L, et al. (2010) Macrophage WNT7b is critical for kidney repair and regeneration Proc Natl Acad Sci USA 107:4194-4199.
32. Cheng J H, et al. (2008) WNT antagonism inhibits hepatic stellate cell activation and liver fibrosis Am J Physiol Gastrointest Liver Physiol 294:G39-49.
33. Yu H M, et al. (2005) The role of Axin2 in calvarial morphogenesis and craniosynostosis Development 132:1995-2005.
34. Ferrer-Vaquer A, et al. (2010) A sensitive and bright single-cell resolution live imaging reporter of WNT/ss-catenin signaling in the mouse BMC Dev Biol 10:121.
35. Lin S L, Kisseleva T, Brenner D A, & Duffield J S (2008) Pericytes and perivascular fibroblasts are the primary source of collagen-producing cells in obstructive fibrosis of the kidney Am J Pathol 173:1617-1627.
36. Hsu H J & Wu M S (2009) Fibroblast growth factor 23: a possible cause of left ventricular hypertrophy in hemodialysis patients Am J Med Sci 337:116-122.
37. Chen Y T, et al. (2011) Platelet-derived growth factor receptor signaling activates pericyte-myofibroblast transition in obstructive and post-ischemic kidney fibrosis Kidney Int 80:1170-1181.
38. Wang S, Denichilo M, Brubaker C, & Hirschberg R (2001) Connective tissue growth factor in tubulointerstitial injury of diabetic nephropathy Kidney Int 60:96-105.
39. Rittie L, et al. (2011) Spatial-temporal modulation of CCN proteins during wound healing in human skin in vivo J Cell Commun Signal 5:69-80.
40. ten Berge D, et al. (2011) Embryonic stem cells require WNT proteins to prevent differentiation to epiblast stem cells Nat Cell Biol 13:1070-1075.
41. Sieczkiewicz G J & Herman I M (2003) TGF-beta 1 signaling controls retinal pericyte contractile protein expression Microvasc Res 66:190-196.
42. Hall-Glenn F, et al. (2012) CCN2/connective tissue growth factor is essential for pericyte adhesion and endothelial basement membrane formation during angiogenesis PLoS One 7:e30562.
43. Kawata K, et al. (2012) Role of low-density lipoprotein receptor related protein 1 (LRP1) in CCN2/connective tissue growth factor (CTGF) protein transport inchondrocytes J Cell Sci.
44. Gao R & Brigstock D R (2005) Connective tissue growth factor (CCN2) in rat pancreatic stellate cell function: integrin alpha5beta1 as a novel CCN2 receptor Gastroenterology 129:1019-1030.
45. Rooney B, et al. (2011) CTGF/CCN2 activates canonical WNT signaling in mesangial cells through LRP6: implications for the pathogenesis of diabetic nephropathy FEBS Lett 585:531-538.
46. Walker N, et al. (2011) Resident tissue-specific mesenchymal progenitor cells contribute to fibrogenesis in human lung allografts Am J Pathol 178:2461-2469.
47. Leask A (2008) Targeting the TGFbeta, endothelin-1 and CCN2 axis to combat fibrosis in scleroderma Cell Signal 20:1409-1414.
48. Yokoi H, et al. (2001) Role of connective tissue growth factor in profibrotic action of transforming growth factor-beta: a potential target for preventing renal fibrosis Am J Kidney Dis 38:S134-138.

49. Kelly O G, Pinson K I, & Skarnes W C (2004) The WNT co-receptors Lrp5 and Lrp6 are essential for gastrulation in mice Development 131:2803-2815.
50. Kokubu C, et al. (2004) Skeletal defects in ringelschwanz mutant mice reveal that Lrp6 is required for proper somitogenesis and osteogenesis Development 131: 5469-5480.
51. Kubota T, et al. (2008) Lrp6 hypomorphic mutation affects bone mass through bone resorption in mice and impairs interaction with Mesd J Bone Miner Res 23:1661-1671.
52. Semenov M V, Zhang X, & He X (2008) DKK1 antagonizes WNT signaling without promotion of LRP6 internalization and degradation J Biol Chem 283:21427-21432.
53. Brault V, et al. (2001) Inactivation of the beta-catenin gene by WNT1-Cremediated deletion results in dramatic brain malformation and failure of craniofacial development Development 128:1253-1264.
54. Duffield, The elusive source of myofibroblasts: problem solved?" Nat Med 2012 8:1178 55. Friedman, et al. Therapy for fibrotic diseases: nearing the starting line. Sci Trans Med 2013 5:167sr1
56. Humphreys, et al. Fate tracing reveals the pericyte and not epithelial origin of myofibroblasts in kidney fibrosis. Am J Path 175(1):85-97 2010.
57. Sponehim, et al. Inflammatory bowel disease-associated interleukin-33 is preferentially expressed in ulceration-associated myofibroblasts. Am J Path 2010 177:2804-15.
58. Hung, et al. Role of lung pericytes and resident fibroblasts in the pathogenesis of pulmonary fibrosis. AJRCCM 2013 188:820
59. Goritz, et al. A pericyte origin of spinal cord scar tissue. Science 2011 333:238
60. Acharya, et al. The bHLH transcription factor Tcf21 is required for lineage-specific EMT of cardiac fibroblast progenitors. Development 2012 139:2139
61. Kisseleva, et al. Myofibroblasts revert to an inactive phenotype during regression of liver fibrosis. PNAS 2012 109:9448
62. Cheng, et al. Crystal structures of the extracellular domain of LRP6 and its complex with DKK1. Nature Structural & Molecular Biology, Vol. 18, No. 11 2011
63. Nakai et al., A limited number of transducible hepatocytes restricts a wide-range linear vector dose response in recombinant adeno-associated virus-mediated liver transduction. J. Virol. 76: 11343-349, 2002
64. Kay et al., Looking into the safety of AAV vectors. Nature 424: 251, 2003
65. Thomas et al., Progress and problems with the use of viral vectors for gene therapy. Nature Reviews, Genetics 4: 346-58, 2003
66. Ren, et al. LRP-6 is a coreceptor for multiple fibrogenic signaling pathways in pericytes and myofibroblasts that are inhibited by DKK-1. PNAS 110: 1440-1445, 2013.
67. Computational Molecular Biology (Lesk, A. M., ed.) Oxford University Press, NY (1988)
68. Biocomputing: Informatics and Genome Projects (Smith, D. W., ed.) Academic Press, NY (1994)
69. Computer Analysis of Sequence Data, Part I (Griffin, A. M., and Griffin, H. G., eds.) Humana Press, NJ (1994)
70. Sequence Analysis in Molecular Biology (Von Heijne, G., ed.) Academic Press (1987)
71. Sequence Analysis Primer (Gribskov, M. and Devereux, J., eds.) Oxford University Press, NY (1992)
72. Altschul, et al., J. Mol. Biol. 215:403-410, 1990
73. Higgins and Sharp (1989) CABIOS. 5:151-153
74. Pearson, Comput. Methods Genome Res., [Proc. Int. Symp.] (1994), Meeting Date 1992, 111-20. Editor(s): Suhai, Sandor. Publisher: Plenum, New York, N.Y.
75. Bundgard, Design of Prodrugs, pp. 7-9, 21-24, Elsevier, Amsterdam (1985)
76. Silverman, The Organic Chemistry of Drug Design and Drag Action, pp. 352-401, Academic Press, San Diego, Calif. (1992)
77. BERNARD N. FIELDS et al., VIROLOGY, volume 2, chapter 69 (4th ed., Lippincott-Raven Publishers).
78. Gao et al., (2004) J. Virology 78:6381-6388
79. Moris et al., (2004) Virology 33:375-383
80. Srivistava et al., (1983) J. Virology 45:555
81. Chiorini et al., (1998) J. Virology 71:6823
82. Chiorini et al., (1999) J. Virology 73:1309
83. Bantel-Schaal et al., (1999) J. Virology 73:939
84. Xiao et al., (1999) J. Virology 73:3994
85. Muramatsu et al., (1996) Virology 221:208
86. Shade et al., (1986) J. Virol. 58:921
87. Gao et al., (2002) Proc. Nat. Acad. Sci. USA 99:11854
88. Moris et al., (2004) Virology 33:375-383
89. International patent publication WO 00/28061
90. International patent publication WO 99/61601
91. International patent publication WO 98/11244
92. U.S. Pat. No. 6,156,303
93. U.S. Pat. No. 6,218,181
94. Sambrook et al., Molecular Cloning: A Laboratory Manual, 3rd ed., Cold Spring Harbor Laboratory Press, Cold Spring Harbor, N.Y., 2001
95. Mullis et al. (1987) U.S. Pat. No. 4,683,202
96. PCR Protocols: A Guide to Methods and Applications (Innis et al., eds.) Academic Press Inc. San Diego, Calif. (1990)
97. Kwoh et al. (1989) Proc Natl Acad Sci USA 86:1173-1177
98. Guatelli et al. (1990) Proc Natl Acad Sci USA 87:1874-1878
99. Lomeli et al. (1989) J Clin Chem 35:1826-1831
100. Landegren et al. (1988) Science 241:1077-1080
101. Van Brunt (1990) Biotechnology 8:291-294
102. Wu and Wallace (1989) Gene 4:560-569
103. Barringer et al. (1990) Gene 89:117-122
104. Sooknanan and Malek (1995) Biotechnology 13:563-564.
105. Wallace et al., U.S. Pat. No. 5,426,039
106. Cheng et al. (1994) Nature 369:684-685
107. Sandana (1997) Bioseparation of Proteins, Academic Press, Inc.
108. Bollag et al. (1996) Protein Methods, 2nd Edition Wiley-Liss, New York
109. Walker (1996) The Protein Protocols Handbook Humana Press, New Jersey
110. Harris and Angal (1990) Protein Purification Applications: A Practical Approach IRL Press at Oxford, Oxford, England
111. Harris and Angal Protein Purification Methods: A Practical Approach IRL Press at Oxford, Oxford, England
112. Scopes (1993) Protein Purification: Principles and Practice 3rd Edition Springer Verlag, New York
113. Janson and Ryden (1998) Protein Purification: Principles, High Resolution Methods and Applications, Second Edition Wiley-VCH, New York
114. Walker (1998) Protein Protocols on CD-ROM Humana Press, New Jersey
115. Sambrook, J., Fritsch, E. F. and Maniatis, T. Molecular Cloning: A Laboratory Manual, Second Ed., Cold Spring Harbor Laboratory Press, Cold Spring Harbor (1989)

116. Remington: The Science and Practice of Pharmacy, 21st Ed. Lippincott Williams & Wilkins, 2006.
117. Sambrook, et al. Molecular Cloning: A Laboratory Manual (Current Edition)
118. DNA Cloning: A Practical Approach, vol. I & II (D. Glover, ed.)
119. Oligonucleotide Synthesis (N. Gait, ed., Current Edition)
120. Nucleic Acid Hybridization (B. Hames & S. Higgins, eds., Current Edition)
121. Transcription and Translation (B. Hames & S. Higgins, eds., Current Edition)
122. CRC Handbook of Parvoviruses, vol. I & II (P. Tijessen, ed.)
123. Fundamental Virology, 2nd Edition, vol. I & II (B. N. Fields and D. M. Knipe, eds.)
124. Ahn et al Dev. Cell 2011

What is claimed is:

1. A method of treating scarring of an organ in a subject in need thereof comprising: administering an effective amount of a molecule that down-regulates the WNT signaling pathways to the subject in need thereof, wherein the molecule comprises:

modified SEQ ID NO:5, wherein amino acid residues 28 to 173 of modified SEQ ID NO:5 are at least 90% identical to amino acid residues 28 to 173 of SEQ ID NO:5, and wherein modified SEQ ID NO:5 comprises at least one amino acid modification independently selected from a substitution, a deletion, or an addition, and wherein amino acid residues 174 to 262 of modified SEQ ID NO:5 are identical to amino acid residues 174 to 262 of SEQ ID NO:5;

modified SEQ ID NO:6, wherein amino acid residues 28 to 53, 62 to 70, and 87 to 116 of modified SEQ ID NO:6 are at least 90% identical to amino acid residues 28 to 53, 62 to 70, and 87 to 116 of SEQ ID NO:6, and wherein modified SEQ ID NO:6 comprises at least one amino acid modification independently selected from a substitution, a deletion, or an addition, and wherein amino acid residues 54 to 61 and 71 to 86 of modified SEQ ID NO:6 are identical to amino acid residues 54 to 61 and 71 to 86 of SEQ ID NO:6;

modified SEQ ID NO:7, wherein amino acid residues 28 to 179 of modified SEQ ID NO:7 are at least 90% identical to amino acid residues 28 to 179 of SEQ ID NO:7, and wherein modified SEQ ID NO:7 comprises at least one amino acid modification independently selected from a substitution, a deletion, or an addition, and wherein amino acid residues 180 to 268 of modified SEQ ID NO:7 are identical to amino acid residues 180 to 268 of SEQ ID NO:7; or modified SEQ ID NO:8, wherein amino acid residues 28 to 53, 62 to 70, and 87 to 116 of modified SEQ ID NO:8 are at least 90% identical to amino acid residues 28 to 53, 62 to 70, and 87 to 116 of SEQ ID NO:8, and wherein modified SEQ ID NO:8 comprises at least one amino acid modification independently selected from a substitution, a deletion, or an addition, and wherein amino acid residues 54 to 61 and 71 to 86 of modified SEQ ID NO:8 are identical to amino acid residues 54 to 61 and 71 to 86 of SEQ ID NO:8;

thereby treating scarring of the organ in the subject.

2. The method of claim 1, wherein the down-regulation occurs based on binding of the molecule to a LRP5 receptor or LRP6 receptor.

3. The method of claim 1, wherein the organ in the subject is a kidney, liver, lung, heart, skin, pancreas, muscle, brain, intestine, eye, or bone marrow.

4. The method of claim 1, wherein the treatment of scarring further treats chronic kidney disease (CKD), diabetes mellitus, hypertension, arteriosclerosis, atherosclerosis, autoimmune disease, lupus, antineutrophil cytoplasmic antibody (ANCA)-associated vasculitis, anti-glomerular basement membrane (GBM) disease, focal segmental glomerular sclerosis (FSGS), IgA nephropathy, membranous nephropathy, Alport Syndrome, polycystic kidney disease, kidney infections, urinary track infections (UTIs), viral kidney disease, bacterial kidney disease, parasite-related kidney disease, CKD following xenobiotic exposure, CKD following sepsis, CKD following ischemic injuries, idiopathic pulmonary fibrosis (IPF), chronic obstructive pulmonary disease (COPD), asthma, scleroderma, ischemic cardomyopathy, post myocardial infraction cardiac failure, fibrosing muscle diseases, fibrosing gut diseases, Crohn's disease, colitis, gut diseases with strictures, scarring of the peritoneum following surgical laparotomies, or pancreatitis.

5. A modified DKK1 protein comprising:

modified SEQ ID NO:5, wherein amino acid residues 28 to 173 of modified SEQ ID NO:5 are at least 90% identical to amino acid residues 28 to 173 of SEQ ID NO:5, and wherein modified SEQ ID NO:5 comprises at least one amino acid modification independently selected from a substitution, a deletion, or an addition, and wherein amino acid residues 174 to 262 of modified SEQ ID NO:5 are identical to amino acid residues 174 to 262 of SEQ ID NO:5;

modified SEQ ID NO:6, wherein amino acid residues 28 to 53, 62 to 70, and 87 to 116 of modified SEQ ID NO:6 are at least 90% identical to amino acid residues 28 to 53, 62 to 70, and 87 to 116 of SEQ ID NO:6, and wherein modified SEQ ID NO:6 comprises at least one amino acid modification independently selected from a substitution, a deletion, or an addition, and wherein amino acid residues 54 to 61 and 71 to 86 of modified SEQ ID NO:6 are identical to amino acid residues 54 to 61 and 71 to 86 of SEQ ID NO:6;

modified SEQ ID NO:7, wherein amino acid residues 28 to 179 of modified SEQ ID NO:7 are at least 90% identical to amino acid residues 28 to 179 of SEQ ID NO:7, and wherein modified SEQ ID NO:7 comprises at least one amino acid modification independently selected from a substitution, a deletion, or an addition, and wherein amino acid residues 180 to 268 of modified SEQ ID NO:7 are identical to amino acid residues 180 to 268 of SEQ ID NO:7; or modified SEQ ID NO:8, wherein amino acid residues 28 to 53, 62 to 70, and 87 to 116 of modified SEQ ID NO:8 are at least 90% identical to amino acid residues 28 to 53, 62 to 70, and 87 to 116 of SEQ ID NO:8, and wherein modified SEQ ID NO:8 comprises at least one amino acid modification independently selected from a substitution, a deletion, or an addition, and wherein amino acid residues 54 to 61 and 71 to 86 of modified SEQ ID NO:8 are identical to amino acid residues 54 to 61 and 71 to 86 of SEQ ID NO:8.

6. The modified DKK1 protein of claim 5, wherein the modified DKK1 protein consists of:

modified SEQ ID NO:5, wherein amino acid residues 28 to 173 of modified SEQ ID NO:5 are at least 90% identical to amino acid residues 28 to 173 of SEQ ID NO:5, and wherein modified SEQ ID NO:5 comprises at least one amino acid modification independently selected from a substitution, a deletion, or an addition, and wherein amino acid residues 174 to 262 of modified SEQ ID NO:5 are identical to amino acid residues 174 to 262 of SEQ ID NO:5;

modified SEQ ID NO:6, wherein amino acid residues 28 to 53, 62 to 70, and 87 to 116 of modified SEQ ID NO:6 are at least 90% identical to amino acid residues 28 to 53, 62 to 70, and 87 to 116 of SEQ ID NO:6, and wherein modified SEQ ID NO:6 comprises at least one amino acid modification independently selected from a substitution, a deletion, or an addition, and wherein amino acid residues 54 to 61 and 71 to 86 of modified SEQ ID NO:6 are identical to amino acid residues 54 to 61 and 71 to 86 of SEQ ID NO:6;

modified SEQ ID NO:7, wherein amino acid residues 28 to 179 of modified SEQ ID NO:7 are at least 90% identical to amino acid residues 28 to 179 of SEQ ID NO:7, and wherein modified SEQ ID NO:7 comprises at least one amino acid modification independently selected from a substitution, a deletion, or an addition, and wherein amino acid residues 180 to 268 of modified SEQ ID NO:7 are identical to amino acid residues 180 to 268 of SEQ ID NO:7; or modified SEQ ID NO:8, wherein amino acid residues 28 to 53, 62 to 70, and 87 to 116 of modified SEQ ID NO:8 are at least 90% identical to amino acid residues 28 to 53, 62 to 70, and 87 to 116 of SEQ ID NO:8, and wherein modified SEQ ID NO:8 comprises at least one amino acid modification independently selected from a substitution, a deletion, or an addition, and wherein amino acid residues 54 to 61 and 71 to 86 of modified SEQ ID NO:8 are identical to amino acid residues 54 to 61 and 71 to 86 of SEQ ID NO:8.

7. A method of treating scarring of a peritoneum, a joint, or a large vessel in a subject in need thereof comprising: administering an effective amount of a molecule that down-regulates the WNT signaling pathways to the subject in need thereof, wherein the molecule comprises:

modified SEQ ID NO:5, wherein amino acid residues 28 to 173 of modified SEQ ID NO:5 are at least 90% identical to amino acid residues 28 to 173 of SEQ ID NO:5, and wherein modified SEQ ID NO:5 comprises at least one amino acid modification independently selected from a substitution, a deletion, or an addition, and wherein amino acid residues 174 to 262 of modified SEQ ID NO:5 are identical to amino acid residues 174 to 262 of SEQ ID NO:5;

modified SEQ ID NO:6, wherein amino acid residues 28 to 53, 62 to 70, and 87 to 116 of modified SEQ ID NO:6 are at least 90% identical to amino acid residues 28 to 53, 62 to 70, and 87 to 116 of SEQ ID NO:6, and wherein modified SEQ ID NO:6 comprises at least one amino acid modification independently selected from a substitution, a deletion, or an addition, and wherein amino acid residues 54 to 61 and 71 to 86 of modified SEQ ID NO:6 are identical to amino acid residues 54 to 61 and 71 to 86 of SEQ ID NO:6;

modified SEQ ID NO:7, wherein amino acid residues 28 to 179 of modified SEQ ID NO:7 are at least 90% identical to amino acid residues 28 to 179 of SEQ ID NO:7, and wherein modified SEQ ID NO:7 comprises at least one amino acid modification independently selected from a substitution, a deletion, or an addition, and wherein amino acid residues 180 to 268 of modified SEQ ID NO:7 are identical to amino acid residues 180 to 268 of SEQ ID NO:7; or modified SEQ ID NO:8, wherein amino acid residues 28 to 53, 62 to 70, and 87 to 116 of modified SEQ ID NO:8 are at least 90% identical to amino acid residues 28 to 53, 62 to 70, and 87 to 116 of SEQ ID NO:8, and wherein modified SEQ ID NO:8 comprises at least one amino acid modification independently selected from a substitution, a deletion, or an addition, and wherein amino acid residues 54 to 61 and 71 to 86 of modified SEQ ID NO:8 are identical to amino acid residues 54 to 61 and 71 to 86 of SEQ ID NO:8;

thereby treating scarring of the peritoneum, the joint, or the large vessel in the subject.

8. The method of claim 1, wherein the modification is a substitutions, and the substitution is independently a substitution of one amino acid of a group for another amino acid of the same group found in one of the following substitution groups:

1) Ala, Gly, Ser, and Thr;
2) Asp and Glu;
3) Asn and Gln;
4) Arg, Lys, and His;
5) Ile, Leu, Met, and Val;
6) Phe, Tyr, and Trp;
7) Gly, Ala, Val, Leu, and Ile;
8) Met and Cys;
9) Asp, Glu, Asn, and Gln;
10) Ala, Ser, Thr, Pro, and Gly;
11) Asp, Asn, Glu, and Gln;
12) His, Arg, and Lys;
13) Met, Leu, Ile, Val, and Cys; or
14) Phe, Tyr, and Trp.

9. The modified DKK1 protein of claim 5, wherein the modification is a substitutions, and the substitution is independently a substitution of one amino acid of a group for another amino acid of the same group found in one of the following substitution groups:
1) Ala, Gly, Ser, and Thr;
2) Asp and Glu;
3) Asn and Gln;
4) Arg, Lys, and His;
5) Ile, Leu, Met, and Val;
6) Phe, Tyr, and Trp;
7) Gly, Ala, Val, Leu, and Ile;
8) Met and Cys;
9) Asp, Glu, Asn, and Gln;
10) Ala, Ser, Thr, Pro, and Gly;
11) Asp, Asn, Glu, and Gln;
12) His, Arg, and Lys;
13) Met, Leu, Ile, Val, and Cys; or
14) Phe, Tyr, and Trp.

\* \* \* \* \*